US009216978B2

(12) United States Patent
Follmann et al.

(10) Patent No.: US 9,216,978 B2
(45) Date of Patent: Dec. 22, 2015

(54) RING-FUSED PYRIMIDINES AND TRIAZINES AND USE THEREOF FOR THE TREATMENT AND/OR PROPHYLAXIS OF CARDIOVASCULAR DISEASES

(75) Inventors: Markus Follmann, Köln (DE); Johannes-Peter Stasch, Solingen (DE); Gorden Redlich, Bochum (DE); Jens Ackerstaff, Berlin (DE); Nils Griebenow, Dormagen (DE); Andreas Knorr, Erkrath (DE); Frank Wunder, Wuppertal (DE); Volkhart Min-Jian Li, Velbert (DE); Walter Kroh, Wuppertal (DE); Lars Bärfacker, Oberhausen (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 74 days.

(21) Appl. No.: 13/806,425

(22) PCT Filed: Jul. 5, 2011

(86) PCT No.: PCT/EP2011/061305
§ 371 (c)(1),
(2), (4) Date: Mar. 7, 2013

(87) PCT Pub. No.: WO2012/004258
PCT Pub. Date: Jan. 12, 2012

(65) Prior Publication Data
US 2014/0350020 A1    Nov. 27, 2014

(30) Foreign Application Priority Data

Jul. 9, 2010   (DE) .......................... 10 2010 031 149
Jan. 28, 2011  (DE) .......................... 10 2011 003 315

(51) Int. Cl.
C07D 471/04    (2006.01)
A61K 31/53     (2006.01)
A61P 9/12      (2006.01)
A61K 45/06     (2006.01)
C07D 487/04    (2006.01)
A61K 31/519    (2006.01)
A61K 31/527    (2006.01)
C07D 491/107   (2006.01)

(52) U.S. Cl.
CPC ............ *C07D 471/04* (2013.01); *A61K 31/519* (2013.01); *A61K 31/527* (2013.01); *A61K 31/53* (2013.01); *A61K 45/06* (2013.01); *C07D 487/04* (2013.01); *C07D 491/107* (2013.01)

(58) Field of Classification Search
CPC ............................. C07D 471/04; A61K 31/53
USPC ................... 544/184, 183; 514/243
See application file for complete search history.

(56) References Cited

U.S. PATENT DOCUMENTS

| 4,833,246 | A  | 5/1989  | Adachi et al. |
| 5,976,523 | A  | 11/1999 | Awaya et al. |
| 6,180,656 | B1 | 1/2001  | Fürstner et al. |
| 6,451,805 | B1 | 9/2002  | Straub et al. |
| 6,743,798 | B1 | 6/2004  | Straub et al. |
| 6,833,364 | B1 | 12/2004 | Straub et al. |
| 6,903,089 | B1 | 6/2005  | Stasch et al. |
| 7,173,037 | B2 | 2/2007  | Alonso-Alija et al. |
| 7,410,973 | B2 | 8/2008  | Feurer et al. |
| 7,414,136 | B2 | 8/2008  | Matsumura et al. |
| 7,541,367 | B2 | 6/2009  | Chiu et al. |
| 8,058,282 | B2 | 11/2011 | Adams et al. |
| 8,242,272 | B2 | 8/2012  | Jimenez et al. |
| 8,309,551 | B2 | 11/2012 | Schirok et al. |
| 8,420,656 | B2 | 4/2013  | Follmann et al. |
| 8,765,769 | B2 | 7/2014  | Follmann et al. |
| 8,859,569 | B2 | 10/2014 | Follmann et al. |
| 2004/0235863 | A1 | 11/2004 | Feurer et al. |
| 2008/0004257 | A1 | 1/2008  | Chan et al. |
| 2011/0218202 | A1 | 9/2011  | Brockunier et al. |
| 2013/0072492 | A1 | 3/2013  | Raghavan et al. |
| 2013/0172372 | A1 | 7/2013  | Follmann et al. |
| 2013/0178475 | A1 | 7/2013  | Moore et al. |
| 2013/0210824 | A1 | 8/2013  | Follmann et al. |
| 2013/0338137 | A1 | 12/2013 | Follmann et al. |
| 2014/0100229 | A1 | 4/2014  | Follmann et al. |
| 2014/0148433 | A1 | 5/2014  | Follmann et al. |
| 2014/0171434 | A1 | 6/2014  | Follmann et al. |
| 2014/0228366 | A1 | 8/2014  | Follmann et al. |
| 2014/0249168 | A1 | 9/2014  | Follmann et al. |
| 2014/0357637 | A1 | 12/2014 | Follmann et al. |

(Continued)

FOREIGN PATENT DOCUMENTS

| CA | 2834901 A1 | 11/2012 |
| CA | 2840886 A1 | 1/2013 |
| CN | 1613849 A  | 5/2005 |

(Continued)

OTHER PUBLICATIONS

Ghofrani et al. Eur Respir Rev 2009; 18: 111, 35-41.*

(Continued)

*Primary Examiner* — Venkataraman Balasubramanian
(74) *Attorney, Agent, or Firm* — Buchanan Ingersoll & Rooney PC

(57) ABSTRACT

The present application relates to novel fused pyrimidines and triazines, to processes for their preparation, to their use alone or in combinations for the treatment and/or prophylaxis of diseases and to their use for preparing medicaments for the treatment and/or prophylaxis of diseases, in particular for the treatment and/or prophylaxis of cardiovascular disorders.

10 Claims, No Drawings

(56) References Cited

U.S. PATENT DOCUMENTS

| | | |
|---|---|---|
| 2015/0025090 A1 | 1/2015 | Follmann et al. |
| 2015/0065533 A1 | 3/2015 | Follmann et al. |

FOREIGN PATENT DOCUMENTS

| | | |
|---|---|---|
| EP | 0634413 A1 | 1/1995 |
| WO | 0006569 A1 | 2/2000 |
| WO | 0183490 A1 | 11/2001 |
| WO | 02059083 A2 | 8/2002 |
| WO | 2010065275 A1 | 6/2010 |
| WO | 2011161099 A1 | 12/2011 |
| WO | 2013030138 A1 | 3/2013 |

OTHER PUBLICATIONS

Freshney, Culture of Animal Cells, A Manual of Basic Technique, Alan R. Liss, Inc., 1983, New York, p. 4.*

Dermer Bio/Technology, 1994, 12:320.*

Dumitrascu et al., "Activation of Soluble Guanylate Cyclase Reverses Experimental Pulmonary Hypertension and Vascular Remodeling," 113(2) Circulation 286, 286-95 (Jan. 2006).

Hobbs, "Soluble guanylate cyclase: an old therapeutic target revisited," 136 British J. Pharmacology 637, 637-40 (2002).

T.A. Michel, "Treatment of Myocardial Ischemia," in Goodman & Gilman's: The Pharmacological Basis of Therapeutics, 823-844 (L.L. Brunton et al., eds. 11th ed., 2006).

Poulos, "Soluble Guanylate Cyclase," Current Opinion in Structural Biology, 736-743 (2006).

Becker et al.,"NO-Independent Regulatory Site of Direct sGC Stimulators like YC-1 and BAY 41-2272," BMC Pharmacology, 2001, 1(13):1-12.

Cheng et al.,"Potential Purine Antagonists VII. Synthesis of 6-Alkylpyrazolo-[3,4-d]pyrimidines," J. Org. Chem., 1958, 23:191-200.

Evgenov et al.,"NO-independent stimulators and activators of soluble guanylate cyclase: discovery and therapeutic potential," Nature Rev. Drug Discovery, Sep. 2006, 5:755-768.

Glass et al., "Stimulation of Human Platelet Guanylate Cyclase by Fatty Acids," J. Biol. Chem., Feb. 25, 1977, 252 (4):1279-1285.

Hassan et al.,"Aryl-Aryl Bond Formation One Century after the Discovery of the Ullmann Reaction," Chem. Rev. 2002, 102: 1359-1469.

Ko et al., "YC-1, a Novel Activator of Platelet Guanylate Cyclase," Blood, Dec. 1994, 84(12): 4226-4233.

Mittendorf et al., "Discovery of Riociguat (BAY 63-2521): A Potent, Oral Stimulator of Soluble Guanylate Cyclase for the Treatment of Pulmonary Hypertension," Chem. Med. Chem., 2009, 4: 853-865.

Mülsch et al., "Effect of YC-1, an NO-independent, superoxide-sensitive stimulator of soluble guanylyl cyclase, on smooth muscle responsiveness to nitrovasodilators," Brit. J. Pharm., 1997, 120:681-689.

Pettibone et al., "A Structurally Novel Stimulator of Guanylate Cyclase with Long-Lasting Hypotensive Activity in the Dog," Euro. J. of Pharmacology, 1985, 116: 307-312.

Sharkovska et al.,"Nitric oxide-independent stimulation of soluble guanylate cyclase reduces organ damage in experimental low-renin and high-renin models," J. Hypertension, 2010, 28(8):1666-1675.

Stasch et al.,"Soluble Guanylate Cyclase as an Emerging Therapeutic Target in Cardiopulmonary Disease," Circulation, May 2011, 123: 2263-2273.

Straub et al., "NO-Independent Stimulators of Soluble Guanylate Cyclase," Bioorg. Med. Chem. Lett., 2001, 11:781-784.

Winn et al., "2-(Alkylamino)nicotinic Acid and Analogs. Potent Angiotensin II Antagonists," J. Med. Chem 1993, 36: 2676-2688.

Witte et al.,"Experimental heart failure in rats: effects on cardiovascular circadian rhythms and on myocardial β-adrenergic signaling," Cardiovascular Research, 2000, 47: 350-358.

Wu et al., "YC-1 inhibited human platelet aggregation through NO-independent activation of soluble guanylate cyclase," Brit. J. Pharmacology, Pharmacol. Oct. 1995, 116(3):1973-1978.

Wunder et al., "A cell-based cGMP assay useful for ultra-high-throughput screening and identification of modulators of the nitric oxide/cGMP pathway," Analytical Biochem., 2005, 339:104-112.

Yu et al., "Vasorelaxant Effect of Isoliquiritigenin, A novel soluble guanylate cyclase activator, in rat aorta," Brit. J. of Pharmacology, 1995, 114: 1587-1594.

Olah et al., "Synthesis and Investigation of Organic Fluorine Compounds. XXIII. Preparation of Aromatic Fluorinated Esters as Local Anesthetics." J. ORganic Chem. 1957, vol. 22, pp. 879-881.

Badesch et al., "Prostanoid Therapy for Pulmonary Arterial Hypertension," Journal of the American College of Cardiology, Jun. 16, 2004, 43:56S-61S.

Ghofrani et al., "Soluble guanylate cyclase stimulation: an emerging option in pulmonary hypertension therapy," Eur. Respir. Rev., 2009, 18(111):35-41.

Freshney, R. Ian., "Culture of animal cells," A Manual of Basic Technique, Alan R. Liss, Inc., 1983, New York, p. 4.

Dermer, G. B., "Another Anniversary for the War on Cancer," Bio/Technology, 1994, 12:320, 8 pages.

Oudot et al., "Combination of BAY 60-4552 and Vardenafil Exerts Proerectile Facilitator Effects in Rats With Cavernous Nerve Injury: A Proof of Concept Study for the Treatment of Phosphodiesterase Type 5 Inhibitor Failure," European Urology, 2011, 60:1020-1026.

U.S. Appl. No. 14/371,054, filed Jan. 8, 2013.

International Search Report issued on Oct. 13, 2011 by the European Patent Office as the International Searching Authority in corresponding Application No. PCT/EP2011/061305 (25 pages).

International Preliminary Report on Patentability (Form PCT/IB/373) and the Written Opinion of the International Searching Authority (Form PCT/ISA/237) issued on Jan. 15, 2013 for corresponding Application No. PCT/EP2011/061305 (16 pages).

* cited by examiner

RING-FUSED PYRIMIDINES AND TRIAZINES AND USE THEREOF FOR THE TREATMENT AND/OR PROPHYLAXIS OF CARDIOVASCULAR DISEASES

The present application relates to novel fused pyrimidines and triazines, to processes for their preparation, to their use alone or in combinations for the treatment and/or prophylaxis of diseases and to their use for preparing medicaments for the treatment and/or prophylaxis of diseases, in particular for the treatment and/or prophylaxis of cardiovascular disorders.

One of the most important cellular transmission systems in mammalian cells is cyclic guanosine monophosphate (cGMP). Together with nitric oxide (NO), which is released from the endothelium and transmits hormonal and mechanical signals, it forms the NO/cGMP system. Guanylate cyclases catalyse the biosynthesis of cGMP from guanosine triphosphate (GTP). The representatives of this family disclosed to date can be divided both according to structural features and according to the type of ligands into two groups: the particulate guanylate cyclases which can be stimulated by natriuretic peptides, and the soluble guanylate cyclases which can be stimulated by NO. The soluble guanylate cyclases consist of two subunits and very probably contain one haem per heterodimer, which is part of the regulatory site. The latter is of central importance for the mechanism of activation. NO is able to bind to the iron atom of haem and thus markedly increase the activity of the enzyme. Haem-free preparations cannot, by contrast, be stimulated by NO. Carbon monoxide (CO) is also able to attach to the central iron atom of haem, but the stimulation by CO is distinctly less than that by NO.

Through the production of cGMP and the regulation, resulting therefrom, of phosphodiesterases, ion channels and protein kinases, guanylate cyclase plays a crucial part in various physiological processes, in particular in the relaxation and proliferation of smooth muscle cells, in platelet aggregation and adhesion and in neuronal signal transmission, and in disorders caused by an impairment of the aforementioned processes. Under pathophysiological conditions, the NO/cGMP system may be suppressed, which may lead for example to high blood pressure, platelet activation, increased cellular proliferation, endothelial dysfunction, atherosclerosis, angina pectoris, heart failure, myocardial infarction, thromboses, stroke and sexual dysfunction.

A possible way of treating such disorders which is independent of NO and aims at influencing the cGMP signaling pathway in organisms is a promising approach because of the high efficiency and few side effects which are to be expected.

Compounds, such as organic nitrates, whose effect is based on NO have to date been exclusively used for the therapeutic stimulation of soluble guanylate cyclase. NO is produced by bioconversion and activates soluble guanylate cyclase by attaching to the central iron atom of haem. Besides the side effects, the development of tolerance is one of the crucial disadvantages of this mode of treatment.

Over the last years, a number of substances which stimulate soluble guanylate cyclase directly. i.e. without prior release of NO, have been described, for example 3-(5'-hydroxymethyl-2'-furyl)-1-benzylindazole [YC-1; Wu et al., Blood 84 (1994), 4226; Mülsch et al., Brit. J. Pharmacol. 120 (1997), 681], fatty acids [Goldberg et al., J. Biol. Chem. 252 (1977), 1279], diphenyliodonium hexafluorophosphate [Pettibone et al., Eur. J. Pharmacol. 116 (1985), 307], isoliquiritigenin [Yu et al., Brit. J. Pharmacol. 114 (1995), 1587], and also various substituted pyrazole derivatives (WO 98/16223).

WO 00/06569 and WO 03/095451 disclose fused pyrazole derivatives and carbamate-substituted 3-pyrimidinylpyrazolopyridines, respectively, as stimulators of soluble guanylate cyclase. WO 2010/065275 discloses substituted pyrrolo- and dihydropyridopyrimidines as sGC activators.

It was an object of the present invention to provide novel substances which act as stimulators of soluble guanylate cyclase and have a comparable or improved therapeutic profile compared to the compounds known from the prior art, for example with respect to their in vivo properties and/or their pharmakokinetic behaviour.

It is an object of the present invention to provide compounds of the general formula (I)

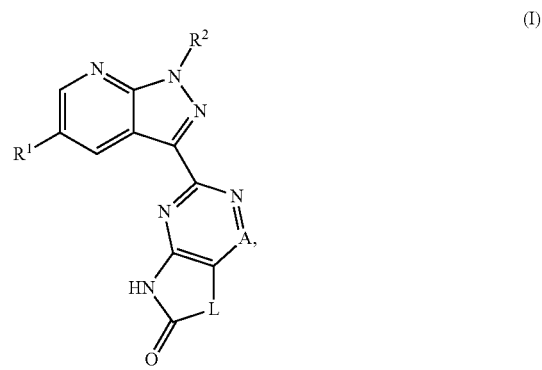

in which

A represents nitrogen or $CR^3$,
where
$R^3$ represents hydrogen, deuterium, fluorine, difluoromethyl, trifluoromethyl, $(C_1-C_4)$-alkyl, cyclopropyl or cyclobutyl, L represents a group *—$CR^{4A}R^{4B}$—$(CR^{5A}R^{5B})_p$-#,
where
* represents the point of attachment to the carbonyl group,
# represents the point of attachment to the pyrimidine or triazine ring,
p represents a number 0, 1 or 2,
$R^{4A}$ represents hydrogen, fluorine, $(C_1-C_4)$-alkyl or hydroxyl,
$R^{4B}$ represents hydrogen, fluorine, $(C_1-C_4)$-alkyl, trifluoromethyl, $(C_1-C_4)$-alkoxy-carbonylamino or phenyl,
where $(C_1-C_4)$-alkyl may be substituted by 1 or 2 substituents independently of one another selected from the group consisting of fluorine, trifluoromethyl, hydroxyl, hydroxycarbonyl and $(C_1-C_4)$-alkoxycarbonyl,
or
$R^{4A}$ and $R^{4B}$ together with the carbon atom to which they are attached form an oxo group, a 3- to 6-membered carbocycle or a 4- to 6-membered heterocycle,
where the 3- to 6-membered carbocycle and the 4- to 6-membered heterocycle may be substituted by 1 or 2 substituents independently of one another selected from the group consisting of fluorine and $(C_1-C_4)$-alkyl,
or
$R^{4A}$ and $R^{4B}$ together with the carbon atom to which they are attached form a $(C_2-C_4)$-alkenyl group,
$R^{5A}$ represents hydrogen, fluorine, $(C_1-C_4)$-alkyl or hydroxyl,
$R^{5B}$ represents hydrogen, fluorine, $(C_1-C_4)$-alkyl or trifluoromethyl, R¹ represents hydrogen or fluorine, R² represents benzyl, where benzyl is substituted by 1 to 3 fluorine substituents, and their N-oxides, salts, solvates, salts of the N-oxides and solvates of the N-oxides and salts.

Compounds according to the invention are the compounds of the formula (I) and their salts, solvates and solvates of the salts, the compounds included in the formula (I) of the formulae mentioned in the following and their salts, solvates and solvates of the salts, and the compounds included in the formula (I) and mentioned in the following as embodiment examples and their salts, solvates and solvates of the salts, where the compounds included in the formula (I) and mentioned in the following are not already salts, solvates and solvates of the salts.

Preferred salts in the context of the present invention are physiologically acceptable salts of the compounds according to the invention. Salts which are not themselves suitable for pharmaceutical uses but can be used, for example, for isolation or purification of the compounds according to the invention are also included.

Physiologically acceptable salts of the compounds according to the invention include acid addition salts of conventional mineral acids, carboxylic acids and sulphonic acids, e.g. salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, formic acid, acetic acid, trifluoroacetic acid, propionic acid, lactic acid, tartaric acid, malic acid, citric acid, fumaric acid, maleic acid, and benzoic acid.

Physiologically acceptable salts of the compounds according to the invention also include salts of conventional bases, such as, by way of example and preferably, alkali metal salts (e.g. sodium and potassium salts), alkaline earth metal salts (e.g. calcium and magnesium salts) and ammonium salts derived from ammonia or organic amines having 1 to 16 carbon atoms, such as, by way of example and preferably, ethylamine, diethylamine, triethylamine, ethyldiisopropylamine, monoethanol-amine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates in the context of the invention are designated as those forms of the compounds according to the invention which form a complex in the solid or liquid state by coordination with solvent molecules. Hydrates are a specific form of solvates, in which the coordination takes place with water. Hydrates are preferred solvates in the context of the present invention.

The compounds according to the invention can exist in different stereoisomeric forms depending on their structure, i.e. in the form of configuration isomers or optionally also as conformation isomers (enantiomers and/or diastereomers, including those in the case of atropisomers). The present invention therefore includes the enantiomers and diastereomers and their particular mixtures. The stereoisomerically uniform constituents can be isolated from such mixtures of enantiomers and/or diastereomers in a known manner; chromatography processes are preferably used for this, in particular HPLC chromatography on an achiral or chiral phase.

Where the compounds according to the invention can occur in tautomeric forms, the present invention includes all the tautomeric forms.

The present invention also encompasses all suitable isotopic variants of the compounds according to the invention. An isotopic variant of a compound according to the invention is understood here to mean a compound in which at least one atom within the compound according to the invention has been exchanged for another atom of the same atomic number, but with a different atomic mass than the atomic mass which usually or predominantly occurs in nature. Examples of isotopes which can be incorporated into a compound according to the invention are those of hydrogen, carbon, nitrogen, oxygen, phosphorus, sulphur, fluorine, chlorine, bromine and iodine, such as $^{2}H$ (deuterium), $^{3}H$ (tritium), $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$. Particular isotopic variants of a compound according to the invention, especially those in which one or more radioactive isotopes have been incorporated, may be beneficial, for example, for the examination of the mechanism of action or of the active compound distribution in the body; due to comparatively easy preparability and detectability, especially compounds labelled with $^{3}H$ or $^{14}C$ isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required; such modifications of the compounds according to the invention may therefore in some cases also constitute a preferred embodiment of the present invention. Isotopic variants of the compounds according to the invention can be prepared by generally used processes known to those skilled in the art, for example by the methods described below and the methods described in the working examples, by using corresponding isotopic modifications of the particular reagents and/or starting compounds therein.

The present invention moreover also includes prodrugs of the compounds according to the invention. The term "prodrugs" here designates compounds which themselves can be biologically active or inactive, but are converted (for example metabolically or hydrolytically) into compounds according to the invention during their dwell time in the body.

In the context of the present invention, the substituents have the following meaning, unless specified otherwise:

Alkyl in the context of the invention represents a straight-chain or branched alkyl radical having 1 to 4 carbon atoms. The following may be mentioned by way of example and by way of preference: methyl, ethyl, n-propyl, isopropyl, n-butyl, isobutyl, 1-methylpropyl, tert-butyl.

Carbocycle in the context of the invention represents a monocyclic saturated carbocycle having 3 to 6 ring carbon atoms. The following may be mentioned by way of example and by way of preference: cyclopropyl, cyclobutyl, cyclopentyl and cyclohexyl.

Alkenyl in the context of the invention represents a straight-chain or branched alkenyl radical having 2 to 4 carbon atoms and a double bond. The following may be mentioned by way of example and by way of preference: vinyl, allyl, isopropenyl and n-but-2-en-1-yl.

Alkoxycarbonyl in the context of the invention represents a straight-chain or branched alkoxy radical having 1 to 4 carbon atoms and a carbonyl group which is attached at the oxygen. The following may be mentioned by way of example and by way of preference: methoxycarbonyl, ethoxycarbonyl, n-propoxycarbonyl, isopropoxycarbonyl and tert-butoxycarbonyl.

Alkoxycarbonylamino in the context of the invention represents an amino group having a straight-chain or branched alkoxycarbonyl substituent which has 1 to 4 carbon atoms in the alkyl chain and is attached to the nitrogen atom via the carbonyl group. The following may be mentioned by way of example and by way of preference: methoxycarbonylamino, ethoxycarbonylamino, propoxy-carbonylamino, n-butoxycarbonylamino, isobutoxycarbonylamino and tert-butoxycarbonylamino.

Heterocycle in the context of the invention represents a saturated heterocycle having a total of 4 to 6 ring atoms which contains one or two ring heteroatoms from the group consisting of N, O, S, SO and/or $SO_2$ and is attached via a ring carbon atom. The following may be mentioned by way of example: azetidinyl, oxetanyl, pyrrolidinyl, pyrazolidinyl, tetrahydrofuranyl, piperidinyl, piperazinyl, tetrahydropyranyl, morpholinyl, thiomorpholinyl and dioxidothiomorpholinyl. Preference is given to azetidinyl, oxetanyl, pyrrolidinyl, tetrahydrofuranyl, piperidinyl and tetrahydropyranyl.

Halogen in the context of the invention represents fluorine, chlorine, bromine and iodine. Preference is given to bromine and iodine.

In the formula of the group which may represent L or $R^2$, the end point of the line at which the *, # or ## symbol is placed does not represent a carbon atom or a $CH_2$ group but forms part of the bond to the marked atom to which L or $R^2$ is attached.

If radicals in the compounds according to the invention are substituted, the radicals may be mono- or polysubstituted, unless specified otherwise. In the context of the present invention, all radicals which occur more than once are defined independently of one another. Substitution by one, two or three identical or different substituents is preferred.

In the context of the present invention, preference is given to compounds of the formula (I) in which
A represents nitrogen or $CR^3$,
  where
    $R^3$ represents hydrogen, deuterium, fluorine, difluoromethyl, trifluoromethyl, $(C_1$-$C_4)$-alkyl, cyclopropyl or cyclobutyl,
  L represents a group *—$CR^{4A}R^{4B}$—$(CR^{5A}R^{5B})_p$-#,
    where
      * represents the point of attachment to the carbonyl group,
      # represents the point of attachment to the pyrimidine or triazine ring,
      p represents a number 0, 1 or 2,
      $R^{4A}$ represents hydrogen, fluorine, $(C_1$-$C_4)$-alkyl, hydroxyl,
      $R^{4B}$ represents hydrogen, fluorine, $(C_1$-$C_4)$-alkyl or trifluoromethyl,
      or
      $R^{4A}$ and $R^{4B}$ together with the carbon atom to which they are attached form an oxo group, a 3- to 6-membered carbocycle or a 4- to 6-membered heterocycle,
      $R^{5A}$ represents hydrogen, fluorine, $(C_1$-$C_4)$-alkyl or hydroxyl,
      $R^{5B}$ represents hydrogen, fluorine, $(C_1$-$C_4)$-alkyl or trifluoromethyl,
  $R^1$ represents hydrogen or fluorine,
  $R^2$ represents benzyl,
    where benzyl is substituted by 1 to 3 fluorine substituents,
and their N-oxides, salts, solvates, salts of the N-oxides and solvates of the N-oxides and salts.

In the context of the present invention, preference is also given to compounds of the formula (I) in which
A represents nitrogen or $CR^3$,
  where
    $R^3$ represents hydrogen, fluorine, difluoromethyl, trifluoromethyl, methyl, ethyl or cyclopropyl,
  L represents a group *—$CR^{4A}R^{4B}$—$(CR^{5A}R^{5B})_p$-#,
    where
      * represents the point of attachment to the carbonyl group,
      # represents the point of attachment to the pyrimidine or triazine ring,
      p represents a number 0 or 1,
      $R^{4A}$ represents hydrogen, fluorine, methyl, ethyl or hydroxyl,
      $R^{4B}$ represents hydrogen, fluorine, methyl, ethyl, trifluoromethyl, methoxycarbonyl-amino or phenyl,
        where methyl and ethyl may be substituted by 1 or 2 substituents independently of one another selected from the group consisting of fluorine, trifluoromethyl and hydroxyl,
      or
      $R^{4A}$ and $R^{4B}$ together with the carbon atom to which they are attached form a cyclopropyl, cyclobutyl, cyclopentyl, azetidinyl, pyrrolidinyl, tetrahydrofuranyl, piperidinyl or tetrahydropyranyl ring,
        where the cyclopropyl, cyclobutyl, cyclopentyl, azetidinyl, pyrrolidinyl, tetrahydrofuranyl, piperidinyl or tetrahydropyranyl ring may be substituted by 1 or 2 substituents independently of one another selected from the group consisting of fluorine and methyl,
      $R^{5A}$ represents hydrogen, fluorine, methyl, ethyl or hydroxyl,
      $R^{5B}$ represents hydrogen, fluorine, methyl, ethyl or trifluoromethyl,
  $R^1$ represents hydrogen or fluorine,
  $R^2$ represents benzyl,
    where benzyl is substituted by 1 to 3 fluorine substituents,
and to their salts, solvates and solvates of the salts.

In the context of the present invention, preference is also given to compounds of the formula (I) in which
A represents nitrogen or $CR^3$,
  where
    $R^3$ represents hydrogen, difluoromethyl, trifluoromethyl, methyl, ethyl or cyclopropyl,
  L represents a group *—$CR^{4A}R^{4B}$—$(CR^{5A}R^{5B})_p$-#,
    where
      * represents the point of attachment to the carbonyl group,
      # represents the point of attachment to the pyrimidine or triazine ring,
      p represents a number 0, 1 or 2,
      $R^{4A}$ represents hydrogen, fluorine, methyl, ethyl or hydroxyl,
      $R^{4B}$ represents hydrogen, fluorine, methyl, ethyl or trifluoromethyl,
      or
      $R^{4A}$ and $R^{4B}$ together with the carbon atom to which they are attached form a cyclopropyl, cyclobutyl, cyclopentyl, azetidinyl, pyrrolidinyl, tetrahydrofuranyl, piperidinyl or tetrahydropyranyl ring,
      $R^{5A}$ represents hydrogen, fluorine, methyl, ethyl or hydroxyl,
      $R^{5B}$ represents hydrogen, fluorine, methyl, ethyl or trifluoromethyl,
  $R^1$ represents hydrogen or fluorine,
  $R^2$ represents benzyl,
    where benzyl is substituted by 1 or 2 fluorine substituents,
and to their salts, solvates and solvates of the salts.

In the context of the present invention, particular preference is also given to compounds of the formula (I) in which
A represents $CR^3$,
  where
    $R^3$ represents hydrogen,
  L represents a group *—$CR^{4A}R^{4B}$—$(CR^{5A}R^{5B})_p$-#,
    where
      * represents the point of attachment to the carbonyl group,
      # represents the point of attachment to the pyrimidine ring, p represents a number 0, $R^{4A}$ represents hydrogen, fluorine, methyl or hydroxyl, $R^{4B}$ represents hydrogen, fluorine, methyl or trifluoromethyl, or $R^{4A}$ and $R^{4B}$ together with the carbon atom to which they are attached form a cyclopropyl or cyclobutyl ring, where the cyclopropyl and the cyclobutyl ring may be substituted by 1 or 2 substituents independently of one another selected from the group consisting of fluorine and methyl, $R^1$ represents hydrogen or fluorine, $R^2$ represents benzyl, where benzyl is substituted by 1 or 2 fluorine substituents, and to their salts, solvates and solvates of the salts.

In the context of the present invention, particular preference is also given to compounds of the formula (I) in which A represents nitrogen, L represents a group *—$CR^{4A}R^{4B}$—$(CR^{5A}R^{5B})_p$-#, where

* represents the point of attachment to the carbonyl group, # represents the point of attachment to the triazine ring, p represents a number 0, $R^{4A}$ represents hydrogen, fluorine or methyl, $R^{4B}$ represents hydrogen, fluorine, methyl or trifluoromethyl, or $R^{4A}$ and $R^{4B}$ together with the carbon atom to which they are attached form a cyclopropyl or cyclobutyl ring, where the cyclopropyl and the cyclobutyl ring may be substituted by 1 or 2 substituents independently of one another selected from the group consisting of fluorine and methyl, $R^1$ represents hydrogen or fluorine, $R^2$ represents benzyl, where benzyl is substituted by 1 or 2 fluorine substituents, and to their salts, solvates and solvates of the salts.

In the context of the present invention, particular preference is also given to compounds of the formula (I) in which A represents nitrogen or $CR^3$, where $R^3$ represents hydrogen, L represents a group *—$CR^{4A}R^{4B}$—$(CR^{5A}R^{5B})_p$-#, where

* represents the point of attachment to the carbonyl group, # represents the point of attachment to the pyrimidine or triazine ring, p represents a number 0, $R^{4A}$ represents hydrogen, fluorine, methyl or hydroxyl, $R^{4B}$ represents hydrogen, fluorine, methyl or trifluoromethyl, or $R^{4A}$ and $R^{4B}$ together with the carbon atom to which they are attached form a cyclopropyl ring, $R^1$ represents hydrogen or fluorine, $R^2$ represents a group of the formula

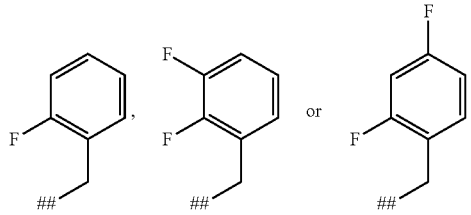

where ## represents the point of attachment to the pyrazolopyridine ring, and to their salts, solvates and solvates of the salts.

In the context of the present invention, preference is also given to compounds of the formula (I) in which $R^1$ represents H, and to their salts, solvates and solvates of the salts.

In the context of the present invention, preference is also given to compounds of the formula (I) in which $R^1$ represents fluorine, and to their salts, solvates and solvates of the salts.

In the context of the present invention, preference is also given to compounds of the formula (I) in which A represents N or CH, and to their salts, solvates and solvates of the salts.

In the context of the present invention, preference is also given to compounds of the formula (I) in which A represents CH, and to their salts, solvates and solvates of the salts.

In the context of the present invention, preference is also given to compounds of the formula (I) in which A represents N, and to their salts, solvates and solvates of the salts.

In the context of the present invention, preference is also given to compounds of the formula (I) in which L represents a group *—$CR^{4A}R^{4B}$—$(CR^{5A}R^{5B})_p$-#, where

* represents the point of attachment to the carbonyl group, # represents the point of attachment to the pyrimidine or triazine ring, p represents a number 0, $R^{4A}$ and $R^{4B}$ together with the carbon atom to which they are attached form a cyclopropyl, cyclobutyl, cyclopentyl, azetidinyl, pyrrolidinyl, tetrahydrofuranyl, piperidinyl or tetrahydropyranyl ring, and to their salts, solvates and solvates of the salts.

In the context of the present invention, preference is also given to compounds of the formula (I) in which L represents a group *—$CR^{4A}R^{4B}$—$(CR^{5A}R^{5B})_p$-#, where

* represents the point of attachment to the carbonyl group, # represents the point of attachment to the pyrimidine or triazine ring, p represents a number 0, $R^{4A}$ represents hydrogen, fluorine, methyl or hydroxyl, $R^{4B}$ represents hydrogen, fluorine, methyl or trifluoromethyl, and to their salts, solvates and solvates of the salts.

In the context of the present invention, preference is also given to compounds of the formula (I) in which L represents a group *—$CR^{4A}R^{4B}$—$(CR^{5A}R^{5B})_p$-#, where

* represents the point of attachment to the carbonyl group, # represents the point of attachment to the pyrimidine or triazine ring, p represents a number 0, $R^{4A}$ represents methyl, $R^{4B}$ represents methyl, and to their salts, solvates and solvates of the salts.

In the context of the present invention, preference is also given to compounds of the formula (I) in which
L represents a group *—$CR^{4A}R^{4B}$—$(CR^{5A}R^{5B})_p$-#,
where
* represents the point of attachment to the carbonyl group,
# represents the point of attachment to the pyrimidine or triazine ring,
p represents a number 0,
$R^{4A}$ and $R^{4B}$ together with the carbon atom to which they are attached form a cyclopropyl or cyclobutyl ring,
where the cyclopropyl and the cyclobutyl ring may be substituted by 1 or 2 substituents independently of one another selected from the group consisting of fluorine and methyl,
and to their salts, solvates and solvates of the salts.

In the context of the present invention, preference is also given to compounds of the formula (I) in which
$R^2$ represents benzyl,
where benzyl is substituted by 1 or 2 fluorine substituents,
and to their salts, solvates and solvates of the salts.

In the context of the present invention, preference is also given to compounds of the formula (I) in which
$R^2$ represents a group of the formula

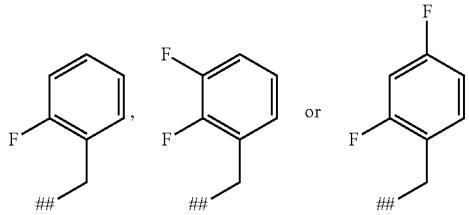

where
## represents the point of attachment to the pyrazolopyridine ring,
and to their salts, solvates and solvates of the salts.

The present invention furthermore provides compounds of the formula (XV)

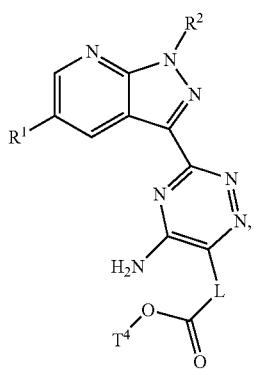

(XV)

in which
L represents a group *—$CR^{4A}R^{4B}$—$(CR^{5A}R^{5B})_p$-#,
where
* represents the point of attachment to the carbonyl group,
# represents the point of attachment to the triazine ring,
p represents a number 0, 1 or 2,
$R^{4A}$ represents hydrogen, fluorine, $(C_1-C_4)$-alkyl or hydroxyl,
$R^{4B}$ represents hydrogen, fluorine, $(C_1-C_4)$-alkyl, trifluoromethyl, $(C_1-C_4)$-alkoxy-carbonylamino or phenyl,
where $(C_1-C_4)$-alkyl may be substituted by 1 or 2 substituents independently of one another selected from the group consisting of fluorine, trifluoromethyl, hydroxyl, hydroxycarbonyl and $(C_1-C_4)$-alkoxycarbonyl,
or
$R^{4A}$ and $R^{4B}$ together with the carbon atom to which they are attached form a 3- to 6-membered carbocycle or a 4- to 6-membered heterocycle,
where the 3- to 6-membered carbocycle and the 4- to 6-membered heterocycle may be substituted by 1 or 2 substituents independently of one another selected from the group consisting of fluorine and $(C_1-C_4)$-alkyl,
$R^{5A}$ represents hydrogen, fluorine, $(C_1-C_4)$-alkyl or hydroxyl,
$R^{5B}$ represents hydrogen, fluorine, $(C_1-C_4)$-alkyl or trifluoromethyl,
$R^1$ represents hydrogen or fluorine,
$R^2$ represents benzyl,
where benzyl is substituted by 1 to 3 fluorine substituents,
$T^4$ represents $(C_1-C_4)$-alkyl,
and to their salts, solvates and solvates of the salts.

The present invention furthermore provides compounds of the formula (XIII)

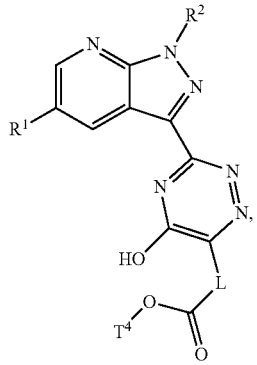

(XIII)

in which
L represents a group *—$CR^{4A}R^{4B}$—$(CR^{5A}R^{5B})_p$-#,
where
* represents the point of attachment to the carbonyl group,
# represents the point of attachment to the triazine ring,
p represents a number 0, 1 or 2,
$R^{4A}$ represents hydrogen, fluorine, $(C_1-C_4)$-alkyl or hydroxyl,
$R^{4B}$ represents hydrogen, fluorine, $(C_1-C_4)$-alkyl, trifluoromethyl, $(C_1-C_4)$-alkoxy-carbonylamino or phenyl,
where $(C_1-C_4)$-alkyl may be substituted by 1 or 2 substituents independently of one another selected from the group consisting of fluorine, trifluoromethyl, hydroxyl, hydroxycarbonyl and $(C_1-C_4)$-alkoxycarbonyl,
or
$R^{4A}$ and $R^{4B}$ together with the carbon atom to which they are attached form a 3- to 6-membered carbocycle or a 4- to 6-membered heterocycle,
where the 3- to 6-membered carbocycle and the 4- to 6-membered heterocycle may be substituted by 1 or 2 substituents independently of one another selected from the group consisting of fluorine and $(C_1\text{-}C_4)$-alkyl, $R^{5A}$ represents hydrogen, fluorine, $(C_1\text{-}C_4)$-alkyl or hydroxyl, $R^{5B}$ represents hydrogen, fluorine, $(C_1\text{-}C_4)$-alkyl or trifluoromethyl, $R^1$ represents hydrogen or fluorine, $R^2$ represents benzyl, where benzyl is substituted by 1 to 3 fluorine substituents, $T^4$ represents $(C_1\text{-}C_4)$-alkyl, and to their salts, solvates and solvates of the salts.

In the context of the present invention, preference is also given to compounds of the formulae (XII) and (XV) in which L represents a group *—$CR^{4A}R^{4B}$—$(CR^{5A}R^{5B})_p$-#, where

* represents the point of attachment to the carbonyl group, # represents the point of attachment to the triazine ring, p represents a number 0, 1 or 2, $R^{4A}$ represents hydrogen, fluorine, methyl, ethyl or hydroxyl, $R^{4B}$ represents hydrogen, fluorine, methyl, ethyl or trifluoromethyl, or $R^{4A}$ and $R^{4B}$ together with the carbon atom to which they are attached form a cyclopropyl, cyclobutyl, cyclopentyl, azetidinyl, pyrrolidinyl, tetrahydrofuranyl, piperidinyl or tetrahydropyranyl ring, $R^{5A}$ represents hydrogen, fluorine, methyl, ethyl or hydroxyl, $R^{5B}$ represents hydrogen, fluorine, methyl, ethyl or trifluoromethyl, $R^1$ represents hydrogen or fluorine, $R^2$ represents benzyl, where benzyl is substituted by 1 or 2 fluorine substituents, $T^4$ represents methyl or ethyl, and to their salts, solvates and solvates of the salts.

In the context of the present invention, preference is also given to compounds of the formulae (XIII) and (XV) in which L represents a group *—$CR^{4A}R^{4B}$—$(CR^{5A}R^{5B})_p$-#, where

* represents the point of attachment to the carbonyl group, # represents the point of attachment to the triazine ring, p represents a number 0, $R^{4A}$ represents methyl, $R^{4B}$ represents methyl, and to their salts, solvates and solvates of the salts.

In the context of the present invention, preference is also given to compounds of the formulae (XIII) and (XV) in which L represents a group *—$CR^{4A}R^{4B}$—$(CR^{5A}R^{5B})_p$-#, where

* represents the point of attachment to the carbonyl group, # represents the point of attachment to the triazine ring, p represents a number 0, $R^{4A}$ and $R^{4B}$ together with the carbon atom to which they are attached form a cyclopropyl or cyclobutyl ring, where the cyclopropyl and the cyclobutyl ring may be substituted by 1 or 2 substituents independently of one another selected from the group consisting of fluorine and methyl, and to their salts, solvates and solvates of the salts.

The definitions of radicals indicated specifically in the respective combinations or preferred combinations of radicals are replaced as desired irrespective of the particular combinations indicated for the radicals also by definitions of radicals of other combinations.

Combinations of two or more of the abovementioned preferred ranges are very particularly preferred.

The invention furthermore provides a process for preparing the compounds of the formula (I) according to the invention, characterized in that a compound of the formula (II)

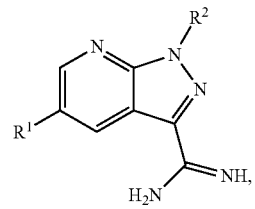

(II)

in which $R^1$ and $R^2$ each have the meanings given above,

[A] is reacted in an inert solvent in the presence of a suitable base with a compound of the formula (III)

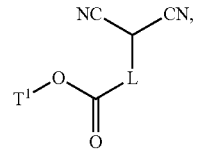

(III)

in which L has the meaning given above and $T^1$ represents $(C_1\text{-}C_4)$-alkyl, to give a compound of the formula (IV)

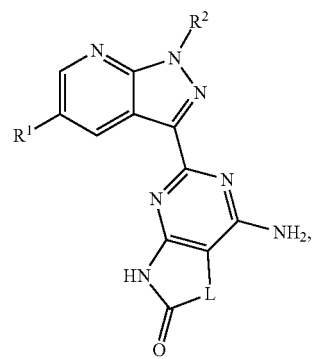

(IV)

in which L, $R^1$ and $R^2$ each have the meanings given above, this is then converted with isopentyl nitrite and an iodine equivalent into a compound of the formula (V)

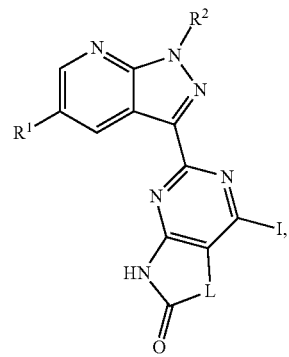

(V)

in which L, $R^1$ and $R^2$ each have the meanings given above, and this is subsequently reacted in an inert solvent in the presence of a suitable transition metal catalyst to give a compound of the formula (I-A)

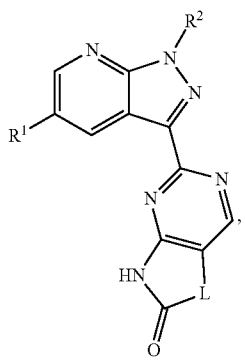
(I-A)

in which L, R¹ and R² each have the meanings given above, or

[B] is reacted in an inert solvent in the presence of a suitable base with a compound of the formula (VI)

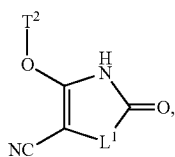
(VI)

in which

L¹ represents a group *—$CR^{4A}R^{4B}$—$(CR^{5A}R^{5B})_p$-#,
where
* represents the point of attachment to the carbonyl group,
# represents the point of attachment to the pyrimidine or triazine ring,
p represents a number 1 or 2,
$R^{4A}$ represents hydrogen, fluorine, ($C_1$-$C_4$)-alkyl or hydroxyl,
$R^{4B}$ represents hydrogen, fluorine, ($C_1$-$C_4$)-alkyl or trifluoromethyl,
or
$R^{4A}$ and $R^{4B}$ together with the carbon atom to which they are attached form an oxo group, a 3- to 6-membered carbocycle or a 4- to 6-membered heterocycle,
$R^{5A}$ represents hydrogen, fluorine, ($C_1$-$C_4$)-alkyl or hydroxyl,
$R^{5B}$ represents hydrogen, fluorine, ($C_1$-$C_4$)-alkyl or trifluoromethyl, and $T^2$ represents ($C_1$-$C_4$)-alkyl, to give a compound of the formula (IV-B)

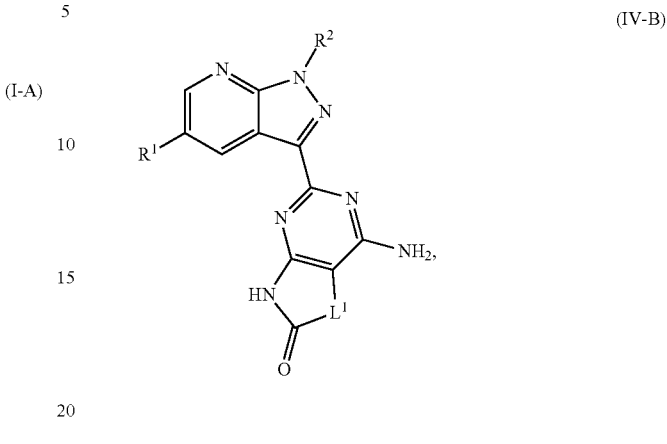
(IV-B)

in which L¹, R¹ and R² each have the meanings given above, and this is then reacted further analogously to process [A] to give a compound of the formula (I-B)

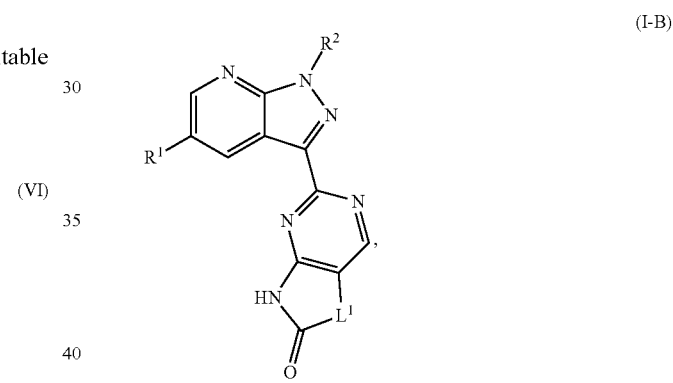
(I-B)

in which L¹, R¹ and R² each have the meanings given above, or

[C] is reacted in an inert solvent in the presence of a suitable base with a compound of the formula (VII)

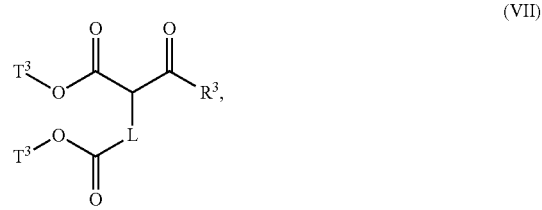
(VII)

in which L and R³ each have the meanings given above
and
$T^3$ represents ($C_1$-$C_4$)-alkyl, to give a compound of the formula (VIII)

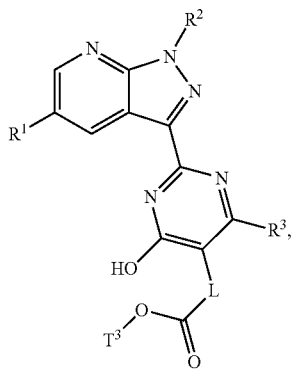
(VIII)

in which L, R¹, R², R³ and T³ each have the meanings given above,
this is then converted with phosphoryl chloride into a compound of the formula (IX)

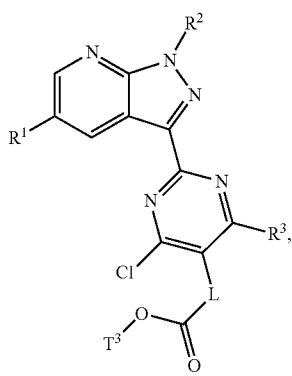
(IX)

in which L, R¹, R², R³ and T³ each have the meanings given above,
this is subsequently converted in an inert solvent into a corresponding azide compound and this is reduced directly to a compound of the formula (X)

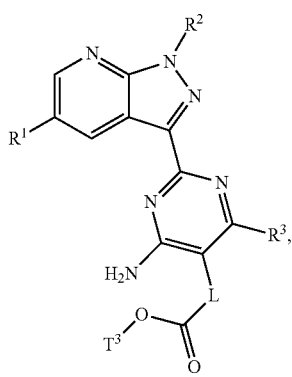
(X)

in which L, R¹, R², R³ and T³ each have the meanings given above,
and this is then reacted in an inert solvent in the presence of a suitable base to give a compound of the formula (I-C)

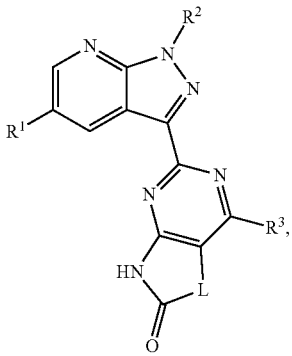
(I-C)

in which L, R¹, R² and R³ each have the meanings given above,
or
[D] is reacted in an inert solvent in the presence of a suitable base with hydrazine hydrate to give a compound of the formula (XI)

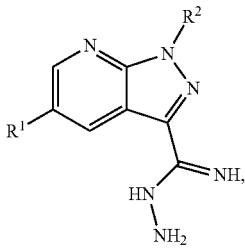
(XI)

in which R¹ and R² each have the meanings given above,
this is then reacted in an inert solvent with a compound of the formula (XII)

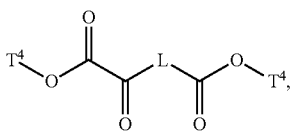
(XII)

in which L has the meaning given above and
T⁴ represents $(C_1\text{-}C_4)$-alkyl,
to give a compound of the formula (XIII)

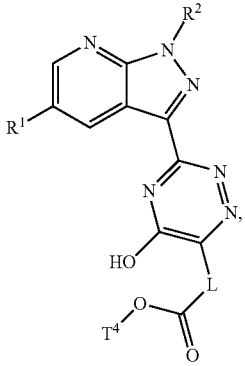
(XIII)

in which L, R¹, R² and T⁴ each have the meanings given above,
this is subsequently converted with phosphoryl chloride into a compound of the formula (XIV)

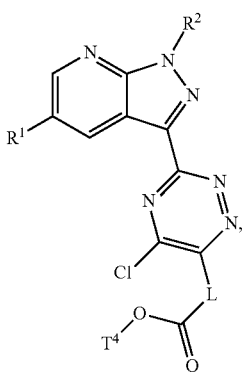

(XIV)

in which L, $R^1$, $R^2$ and $T^4$ each have the meanings given above, and this is reacted directly with ammonia to give a compound of the formula (XV)

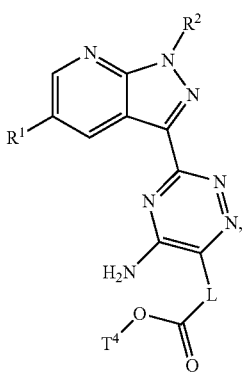

(XV)

in which L, $R^1$, $R^2$ and $T^4$ each have the meanings given above, and finally cyclized in an inert solvent in the presence of a suitable base to give a compound of the formula (I-D)

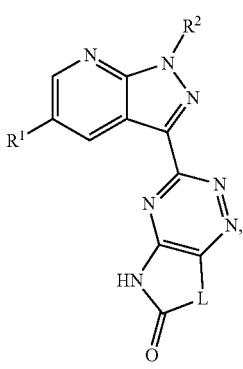

(I-D)

in which L, $R^1$ and $R^2$ each have the meanings given above, and the resulting compounds of the formulae (I-A), (I-B), (I-C) and (I-D) are optionally converted with the appropriate (i) solvents and/or (ii) acids or bases into their solvates, salts and/or solvates of the salts.

Together, the compounds of the formulae (I-A), (I-B), (I-C) and (I-D) form the group of the compounds of the formula (I) according to the invention.

Inert solvents for the process steps (II)+(III) and (VI)→(IV) are, for example, alcohols such as methanol, ethanol, n-propanol, isopropanol, n-butanol or tert-butanol, ethers such as diethyl ether, dioxane, dimethoxyethane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulphoxide (DMSO), N,N'-dimethylpropyleneurea (DMPU), N-methylpyrrolidone (NMP), pyridine, acetonitrile, sulpholane or else water. It is also possible to use mixtures of the solvents mentioned. Preference is given to tert-butanol or methanol.

Suitable bases for the process steps (II)+(III) and (VI)→(IV) are alkali metal hydroxides such as, for example, lithium hydroxide, sodium hydroxide or potassium hydroxide, alkali metal carbonates such as lithium carbonate, sodium carbonate, potassium carbonate or caesium carbonate, alkali metal bicarbonates such as sodium bicarbonate or potassium bicarbonate, alkali metal alkoxides such as sodium methoxide or potassium methoxide, sodium ethoxide or potassium ethoxide or potassium tert-butoxide, or organic amines such as triethylamine, diisopropylethylamine, pyridine, 1,8-diazabicyclo[5.4.0]undec-7-ene (DBU) or 1,5-diazabicyclo[4.3.0]non-5-ene (DBN). Preference is given to potassium tert-butoxide or sodium methoxide.

The reactions (II)+(III) and (VI)→(IV) are generally carried out in a temperature range from +20° C. to +150° C., preferably at from +75° C. to +100° C., if appropriate in a microwave. The reaction can be carried out at atmospheric pressure, at elevated pressure or at reduced pressure (for example at from 0.5 to 5 bar). In general, the reaction is carried out at atmospheric pressure.

The process step (IV)→(V) is carried out in the presence or absence of a solvent. Suitable solvents are all organic solvents which are inert under the reaction conditions. The preferred solvent is dimethoxyethane.

The reaction (IV)→(V) is generally carried out in a temperature range from +20° C. to +100° C., preferably in the range from +50° C. to +100° C., if appropriate in a microwave. The reaction can be carried out at atmospheric pressure, at elevated pressure or at reduced pressure (for example in the range from 0.5 to 5 bar). In general, the reaction is carried out at atmospheric pressure.

The process step (IV)→(V) is generally carried out using a molar ratio of 10 to 30 mol of isopentyl nitrite and 10 to 30 mol of the iodine equivalent per mole of the compound of the formula (IV).

A suitable source of iodine for the reaction (IV)→(V) is, for example, diiodomethane or a mixture of caesium iodide, iodine and copper(I) iodide.

Inert solvents for the process step (V)→(I-A) are alcohols such as methanol, ethanol, n-propanol, isopropanol, n-butanol, tert-butanol or 1,2-ethanediol, ethers such as diethyl ether, dioxane, tetra-hydrofuran, glycol dimethyl ether or diethylene glycol dimethyl ether, or other solvents such as dimethylformamide (DMF), dimethyl sulphoxide (DMSO), N,N'-dimethylpropyleneurea (DMPU), N-methylpyrrolidone (NMP), pyridine, acetonitrile or else water. It is also possible to use mixtures of the solvents mentioned. Preference is given to DMF.

The reduction (V)→(I-A) is carried out using hydrogen in association with transition metal catalysts such as, for example, palladium (10% on activated carbon), Raney nickel or palladium hydroxide.

The reaction (V)→(I-A) is generally carried out in a temperature range from +20° C. to +50° C. The reaction can be carried out at atmospheric or elevated pressure (for example in the range from 0.5 to 5 bar). In general, the reaction is carried out at atmospheric pressure.

Inert solvents for the process step (II)+(VII)→(VIII) are, for example, alcohols such as methanol, ethanol, n-propanol, isopropanol, n-butanol or tert-butanol, ethers such as diethyl ether, dioxane, dimethoxyethane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulphoxide (DMSO), N,N'-dimethylpropyleneurea (DMPU), N-methylpyrrolidone (NMP), pyridine or acetonitrile. It is also possible to use mixtures of the solvents mentioned. Preference is given to methanol or ethanol.

Suitable bases for the process step (II)+(VII)→(VIII) are alkali metal hydroxides such as, for example, lithium hydroxide, sodium hydroxide or potassium hydroxide, alkali metal carbonates such as lithium carbonate, sodium carbonate, potassium carbonate or caesium carbonate, alkali metal bicarbonates such as sodium bicarbonate or potassium bicarbonate, alkali metal alkoxides such as sodium methoxide or potassium methoxide, sodium ethoxide or potassium ethoxide or potassium tert-butoxide, or organic amines such as triethylamine, diisopropylethylamine, pyridine, 1,8-diazabicyclo[5.4.0]undec-7-ene (DBU) or 1,5-diazabicyclo[4.3.0]non-5-ene (DBN). Preference is given to sodium methoxide or sodium ethoxide.

The reaction (II)+(VII)→(VIII) is generally carried out in a temperature range from +50° C. to +120° C., preferably from +50° C. to +100° C., if appropriate in a microwave. The reaction can be carried out at atmospheric or elevated pressure (for example in the range from 0.5 to 5 bar). In general, the reaction is carried out at atmospheric pressure.

The reactions (VIII)→(IX) and (XIII)→(XIV) can be carried out in a solvent which is inert under the reaction conditions, or in the absence of a solvent. The preferred solvent is sulpholane.

The reactions (VIII)→(IX) and (XIII)→(XIV) are generally carried out in a temperature range from +70° C. to +150° C., preferably from +80° C. to +130° C., if appropriate in a microwave. The reaction can be carried out at atmospheric or elevated pressure (for example in the range from 0.5 to 5 bar). In general, the reaction is carried out at atmospheric pressure.

Especially preferably, the reaction (XIII)→(XIV) is carried out in the absence of a solvent in a temperature range from 0° C. to +50° C. at atmospheric pressure.

The process step (IX)→(X) takes place by reaction with sodium azide with intermediate formation of the azide derivatives, which are directly reduced to give the corresponding amines. Inert solvents are the azide formation are, for example, ethers such as diethyl ether, dioxane, dimethoxyethane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulphoxide (DMSO), N,N'-dimethylpropyleneurea (DMPU), N-methylpyrrolidone (NMP), pyridine, acetonitrile or sulpholane. It is also possible to use mixtures of the solvents mentioned. Preference is given to DMF.

The azide formation is generally carried out in a temperature range from +50° C. to +100° C., preferably from +60° C. to +80° C., at atmospheric pressure.

The reduction takes place in an inert solvent such as, for example, alcohols such as methanol, ethanol, n-propanol, isopropanol, n-butanol, tert-butanol or 1,2-ethanediol, ethers such as diethyl ether, dioxane, tetrahydrofuran, glycol dimethyl ether or diethylene glycol dimethyl ether, or other solvents such as dimethylformamide (DMF), dimethyl sulphoxide (DMSO), N,N'-dimethylpropyleneurea (DMPU), N-methylpyrrolidone (NMP), pyridine, acetonitrile or else water. It is also possible to use mixtures of the solvents mentioned. Preference is given to DMF.

The reduction takes place at from +10° C. to +30° C. using hydrogen in combination with transition metal catalysts such as, for example, palladium (10% on activated carbon), platinum dioxide or palladium hydroxide, or without hydrogen using tin(II) chloride and hydrochloric acid.

Alternatively, the reaction (IX)→(X) can also be carried out in one step analogously to process step (XIV)→(XV).

The process step (XIV)→(XV) is carried out in a solvent which is inert under the reaction conditions. Suitable solvents are, for example, ethers such as diethyl ether, dioxane, tetrahydrofuran, glycol dimethyl ether or diethylene glycol dimethyl ether, or other solvents such as dimethylformamide (DMF), dimethyl sulphoxide (DMSO), N,N'-dimethylpropyleneurea (DMPU), N-methylpyrrolidone (NMP), pyridine, acetonitrile or else water. It is also possible to use mixtures of the solvents mentioned. Preference is given to acetonitrile.

The reaction (XIV)→(XV) is generally carried out in a temperature range from +20° C. to +100° C., preferably from +40° C. to +70° C., if appropriate in a microwave. The reaction can be carried out at atmospheric or elevated pressure (for example in the range from 0.5 to 5 bar). In general, the reaction is carried out at atmospheric pressure.

The cyclizations (X)→(I-C) and (XV)→(I-D) are carried out in a solvent which is inert under the reaction conditions such as, for example, alcohols such as methanol, ethanol, n-propanol, isopropanol, n-butanol or tert-butanol, ethers such as diethyl ether, dioxane, dimethoxyethane, tetrahydrofuran (THF), glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulphoxide (DMSO), N,N'-dimethylpropyleneurea (DMPU), N-methylpyrrolidone (NMP), pyridine, acetonitrile or sulpholane. It is also possible to use mixtures of the solvents mentioned. Preference is given to THF.

Suitable bases for the process steps (X)→(I-C) and (XV)→(I-D) are alkali metal hydroxides such as, for example, lithium hydroxide, sodium hydroxide or potassium hydroxide, alkali metal carbonates such as lithium carbonate, sodium carbonate, potassium carbonate or caesium carbonate, alkali metal bicarbonates such as sodium bicarbonate or potassium bicarbonate, alkali metal alkoxides such as sodium methoxide or potassium methoxide, sodium ethoxide or potassium ethoxide or potassium tert-butoxide, or organic amines such as triethylamine, diiso-propylethylamine, pyridine, 1,8-diazabicyclo[5.4.0]undec-7-ene (DBU) or 1,5-diazabicyclo[4.3.0]-non-5-ene (DBN). Preference is given to potassium tert-butoxide.

The reactions (X)→(I-C) and (XV)→(I-D) are generally carried out in a temperature range from 0° C. to +50° C., preferably from +10° C. to +30° C., if appropriate in a microwave. The reaction can be carried out at atmospheric or elevated pressure (for example in the range from 0.5 to 5 bar). In general, the reaction is carried out at atmospheric pressure.

Alternatively, the cyclization to (I-C) or (I-D) takes place directly during the reduction of the azide to the corresponding amine (X) or during the reaction (XIV)→(XV) without addition of further reagents.

In an alternative practice of the processes [C] and [D], the reactions (IX)→(X)→(I-C) and (XI)+(XII)→(XIII)→(XIV)→(XV)→(I-D), respectively, are carried out simultaneously in a one-pot reaction without isolation of the intermediates.

Preferably, the reactions (XIII)→(XIV)→(XV)→(I-D) are carried out simultaneously in a one-pot reaction without isolation of the intermediates.

Inert solvents for the process step (XI)+(XII)→(XIII) are, for example, alcohols such as methanol, ethanol, n-propanol, isopropanol, n-butanol or tert-butanol, ethers such as diethyl ether, dioxane, dimethoxyethane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulphoxide (DMSO), N,N'-dimethylpropyleneurea (DMPU), N-methylpyrrolidone (NMP), pyridine or acetonitrile. It is also possible to use mixtures of the solvents mentioned. Preference is given to methanol or ethanol.

The reaction (XI)+(XII)→(XIII) is generally carried out in a temperature range from +50° C. to +120° C., preferably from +50° C. to +100° C., if appropriate in a microwave. The reaction can be carried out at atmospheric or elevated pressure (for example in the range from 0.5 to 5 bar). In general, the reaction is carried out at atmospheric pressure.

Inert solvents for the process step (II)→(XI) are, for example, alcohols such as methanol, ethanol, n-propanol, isopropanol, n-butanol or tert-butanol, ethers such as diethyl ether, dioxane, dimethoxyethane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulphoxide (DMSO), N,N'-dimethylpropyleneurea (DMPU), N-methylpyrrolidone (NMP), pyridine or acetonitrile. It is also possible to use mixtures of the solvents mentioned. Preference is given to ethanol.

Suitable bases for the process step (II)→(XI) are alkali metal hydroxides such as, for example, lithium hydroxide, sodium hydroxide or potassium hydroxide, alkali metal carbonate such as lithium carbonate, sodium carbonate, potassium carbonate or caesium carbonate, alkali metal bicarbonate such as sodium bicarbonate or potassium bicarbonate, alkali metal alkoxides such as sodium methoxide or potassium methoxide, sodium ethoxide or potassium ethoxide or potassium tert-butoxide, or organic amines such as triethylamine, diisopropylethylamine, pyridine, 1,8-diazabicyclo[5.4.0]undec-7-ene (DBU) or 1,5-diazabicyclo[4.3.0]non-5-ene (DBN). Preference is given to triethylamine.

The reaction (II)→(XI) is generally carried out in a temperature range from 0° C. to +60° C., preferably from +10° C. to +30° C. The reaction can be carried out at atmospheric or elevated pressure (for example in the range from 0.5 to 5 bar). In general, the reaction is carried out at atmospheric pressure.

The preparation processes described can be illustrated in an exemplary manner by the synthesis schemes below (Schemes 1 to 4):

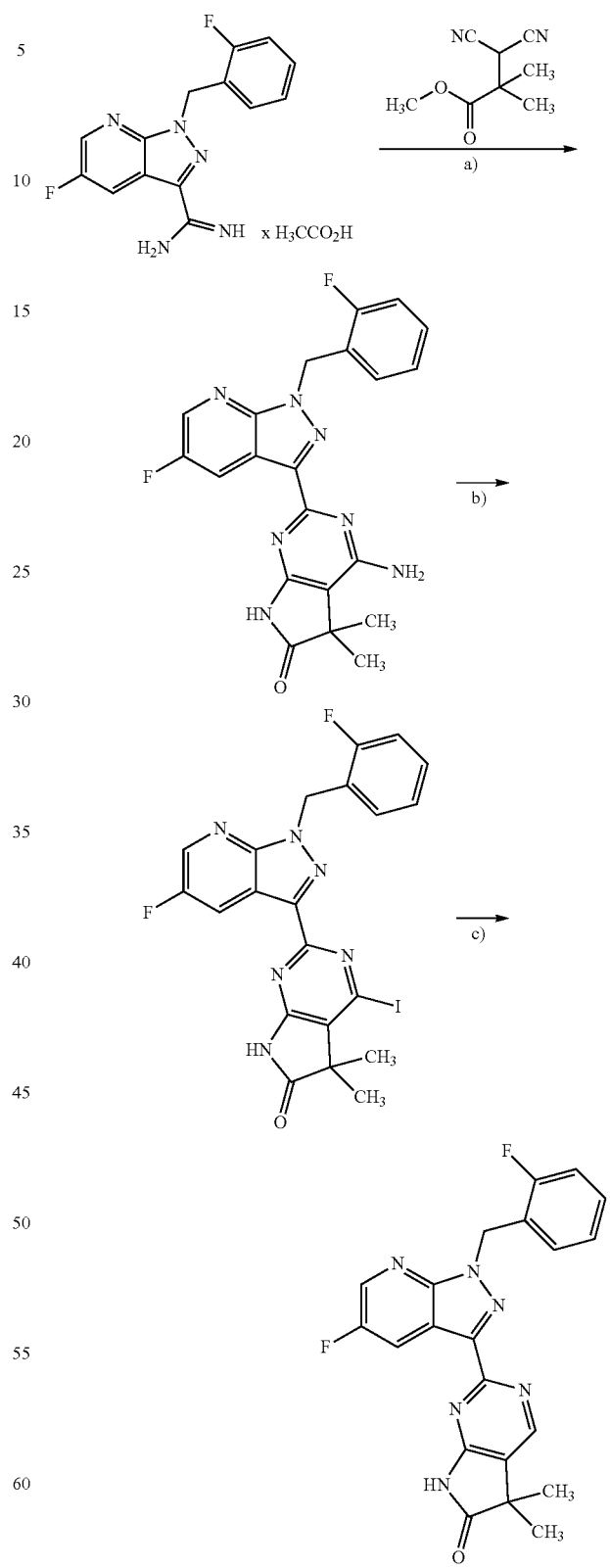

[a]: KOt-Bu, tert-butanol; b): diiodomethane, isopentyl nitrite; c): Pd/C, hydrogen, DMF].

Scheme 2
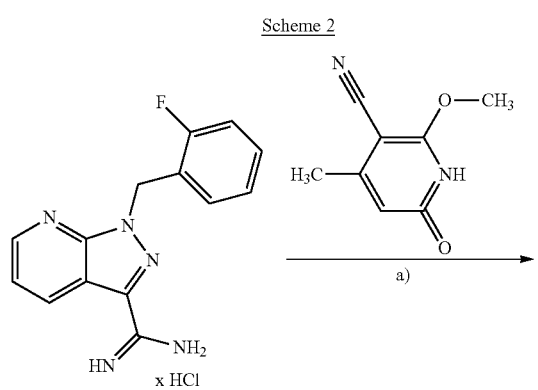
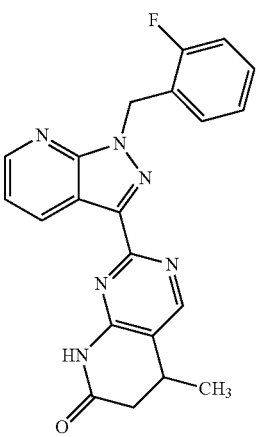
[a): NaOMe, methanol, 65° C., b): CsI, I₂, CuI₂, isopentyl nitrite, 1,2-dimethoxyethane; c): Pd/C, hydrogen, DMF].
Scheme 3
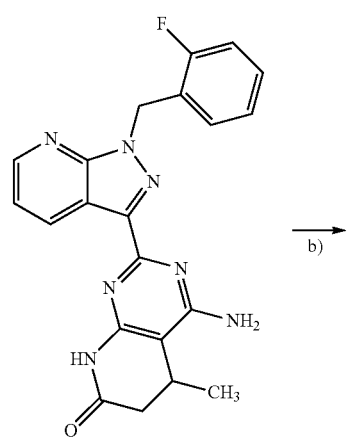
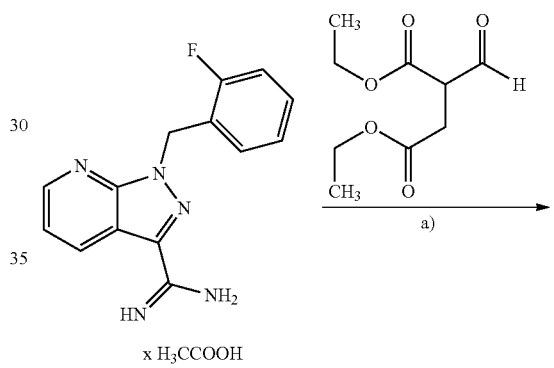
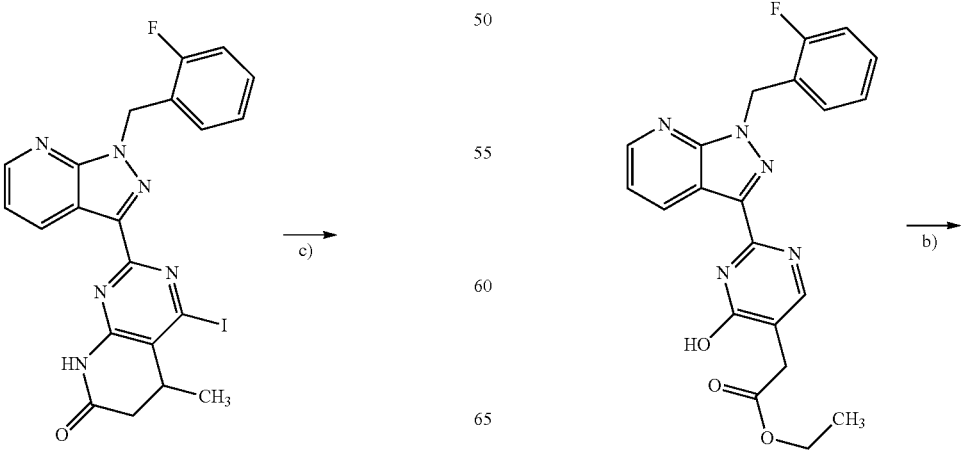

25
-continued
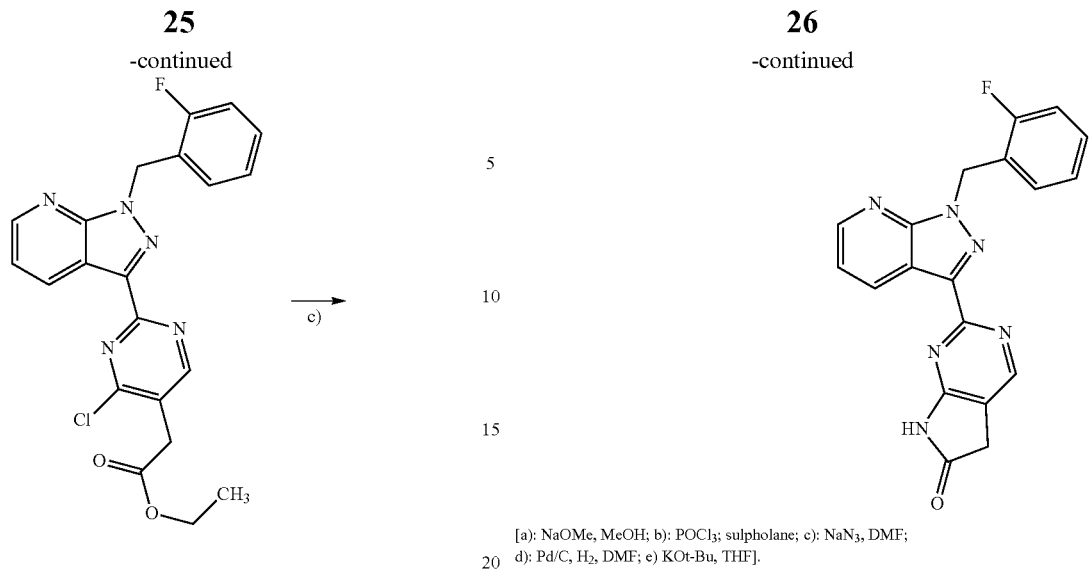
[a]: NaOMe, MeOH; b): POCl3; sulpholane; c): NaN3, DMF;
d): Pd/C, H2, DMF; e) KOt-Bu, THF].
Scheme 4
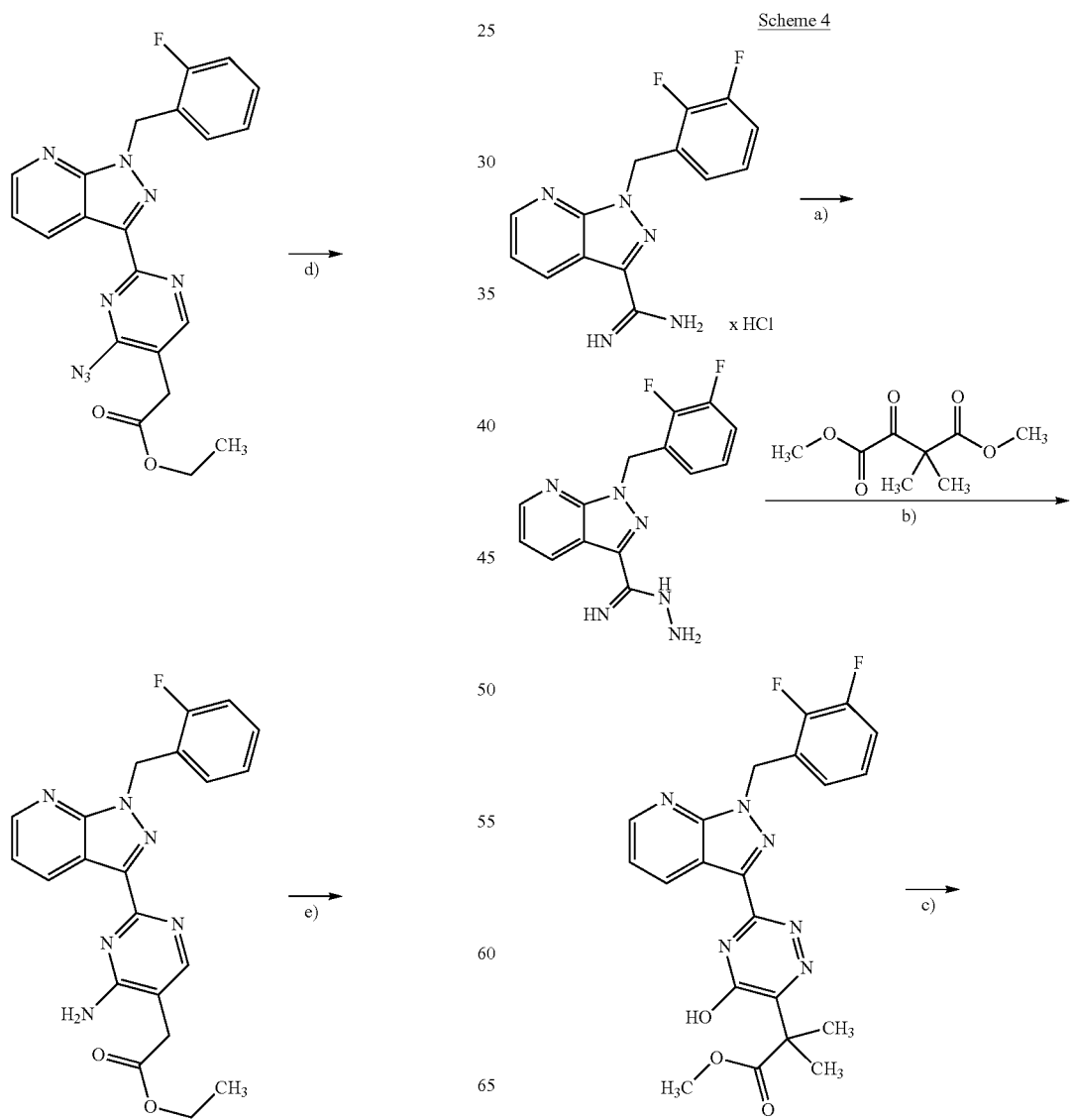

27
-continued

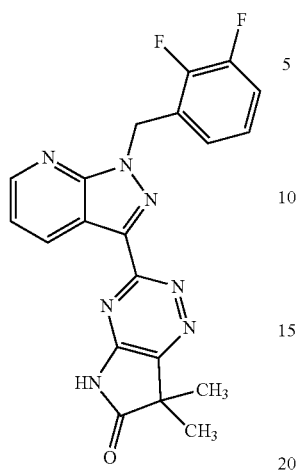

[a]: hydrazine hydrate, NEt₃, EtOH b): EtOH c): 1. POCl₃; 2. conc. NH₃, acetonitrile].

Further compounds according to the invention can also be prepared by converting functional groups of individual substituents, in particular those listed under L and R³, starting with the compounds of the formula (I), (IX) or (XIV) obtained by the above processes. These conversions can be carried out by customary methods known to the person skilled in the art and include, for example, reactions such as nucleophilic and electrophilic substitutions, oxidations, reductions, hydrogenations, transition metal-catalysed coupling reacxctions, eliminations, alkylation, amination, esterification, ester hydrolysis, etherification, ether cleavage, formation of carboxamides, and also the introduction and removal of temporary protective groups. The synthesis schemes below (Schemes 5, 6, 11 and 12) illustrate preferred conversions in an exemplary manner:

Scheme 5

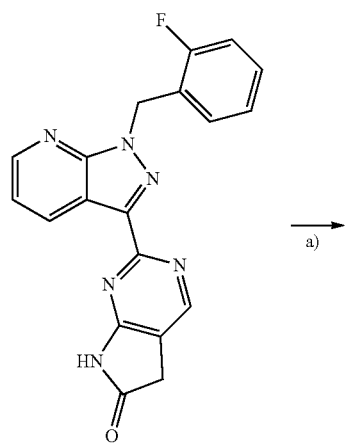
a)

28
-continued

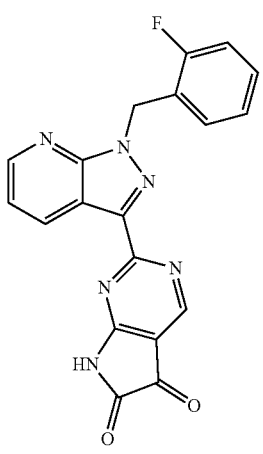

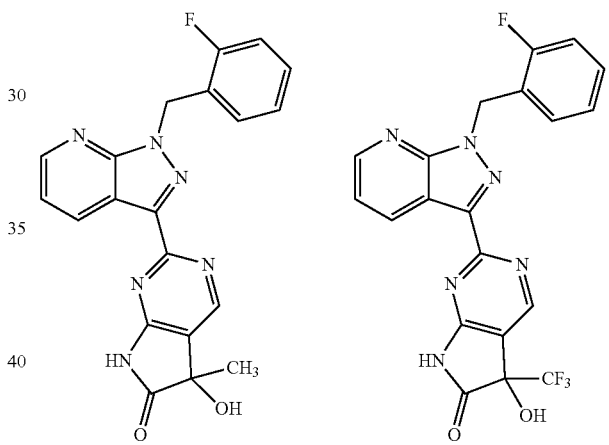

[a]: selenium dioide, dioxane; b): MeMgBr, THF c): CsF, (trifluoromethyl)trimethylsilane, dimethoxyethane].

Scheme 6

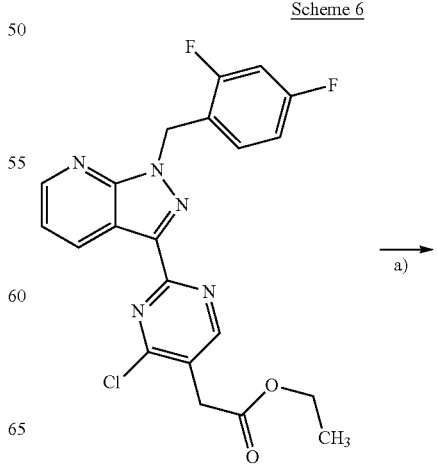
a)

29
-continued
30
-continued
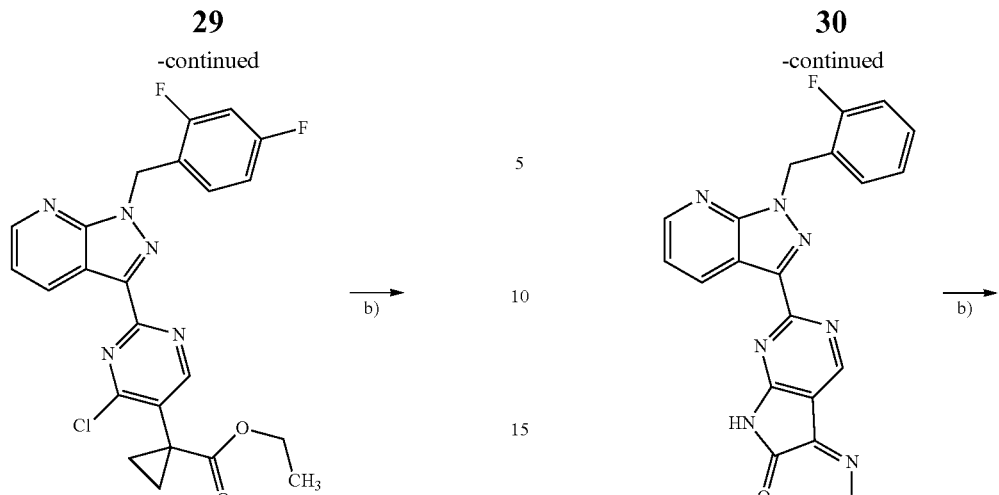
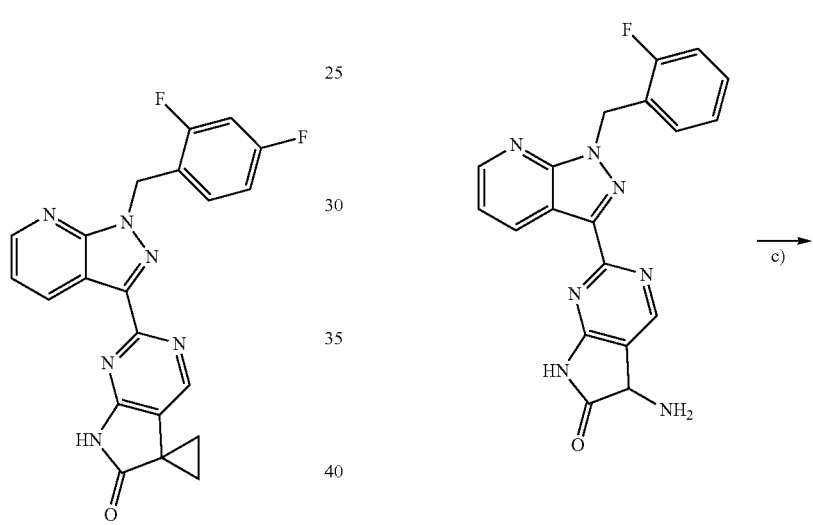
[a): NaH, dibromoethane, DMF; b): 1. NaN₃, DMF, 2. Pd/C, H₂, DMF, 3. KOt-Bu, THF].
Scheme 11
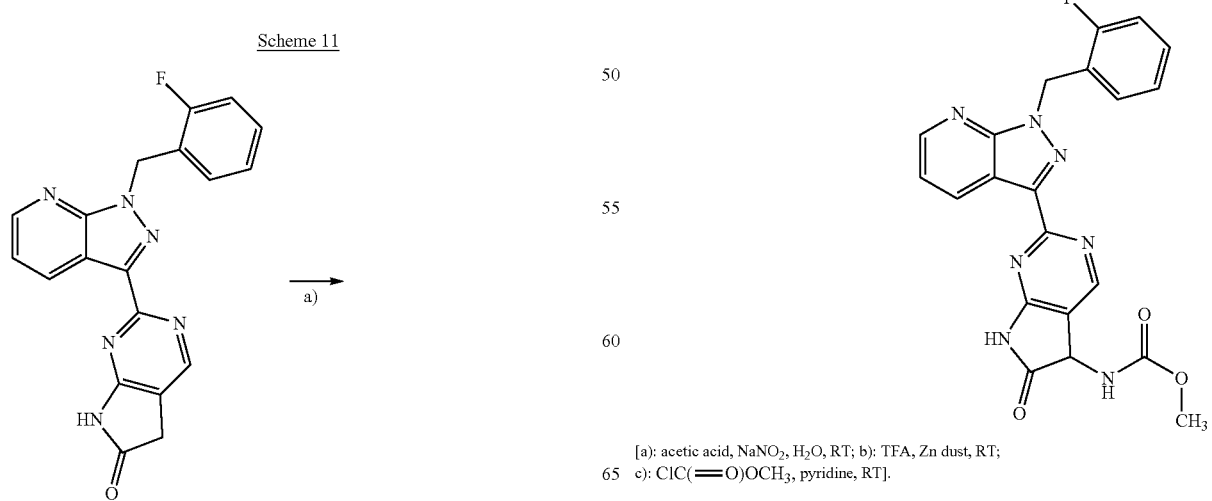
[a): acetic acid, NaNO₂, H₂O, RT; b): TFA, Zn dust, RT;
c): ClC(=O)OCH₃, pyridine, RT].

Scheme 12

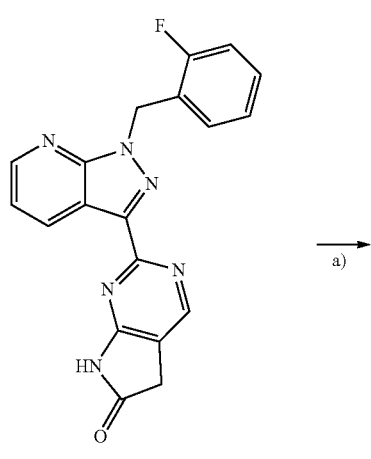

a)

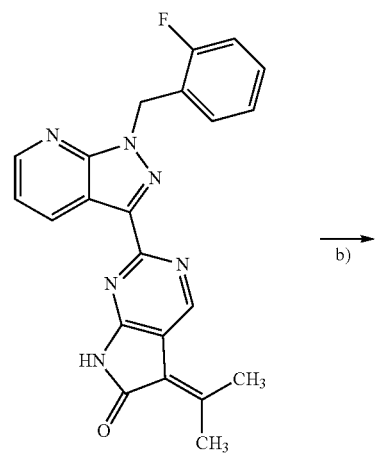

b)

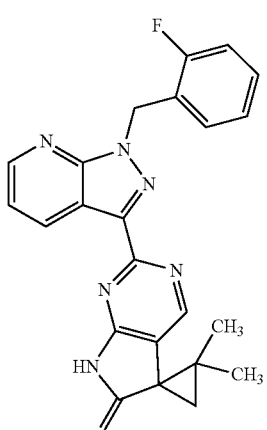

[a): piperidine, RT; b) trimethylsulphoxonium iodide, NaH, DMSO, RT → 50° C.].

The compounds of the formula (H) are known from the literature (see, for example, WO 03/095451, Example 6A) or can be prepared by cyclizing a compound of the formula (XVI)

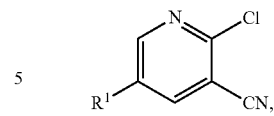

(XVI)

in which $R^1$ has the meaning given above, in an inert solvent with hydrazine hydrate to give the compound of the formula (XVII)

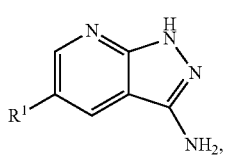

(XVII)

in which $R^1$ has the meaning given above, then reacting this in an inert solvent in the presence of a suitable Lewis acid first with isopentyl nitrite to give the corresponding diazonium salt and then converting this directly with sodium iodide in the compound of the formula (XVIII)

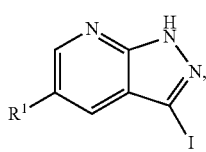

(XVIII)

in which $R^1$ has the meaning given above, subsequently converting this in an inert solvent in the presence of a suitable base with the compound of the formula (XIX)

$$R^2—X^1 \quad \text{(XIX)},$$

in which $R^2$ has the meaning given above and $X^1$ represents a suitable leaving group, such as, for example, halogen, tosylate or mesylate, into a compound of the formula (XX)

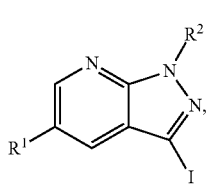

(XX)

in which $R^1$ and $R^2$ each have the meanings given above, then reacting this in an inert solvent with copper cyanide to give a compound of the formula (XXI)

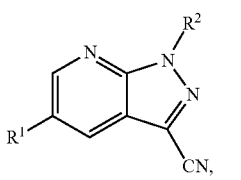

(XXI)

in which $R^1$ and $R^2$ each have the meanings given above,
and finally reacting this under acidic conditions with one equivalent of ammonia.

Inert solvents for the process step (XVI)→(XVII) are alcohols such as methanol, ethanol, n-propanol, isopropanol, n-butanol, tert-butanol or 1,2-ethanediol, ethers such as diethyl ether, dioxane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulphoxide (DMSO), NX-dimethylpropyleneurea (DMPU), N-methylpyrrolidone (NMP), pyridine, acetonitrile or else water. It is also possible to use mixtures of the solvents mentioned. Preference is given to 1,2-ethanediol.

The reaction (XVI)→(XVII) is generally carried out in a temperature range from +60° C. to +200° C., preferably at from +120° C. to +180° C. The reaction can be carried out at atmospheric pressure, at elevated pressure or at reduced pressure (for example at from 0.5 to 5 bar). In general, the reaction is carried out at atmospheric pressure.

Inert solvents for the reaction (XVII)→(XVIII) are, for example, halogenated hydrocarbons such as dichloromethane, trichloromethane, carbon tetrachloride, trichloroethylene or chlorobenzene, ethers such as diethyl ether, dioxane, tetrahydrofuran, glycol dimethyl ether or diethylene glycol dimethyl ether, or other solvents such as dimethylformamide (DMF), dimethyl sulphoxide (DMSO), N,N'-dimethylpropyleneurea (DMPU), N-methylpyrrolidone (NMP), pyridine or acetonitrile. Preference is given to DMF.

Suitable Lewis acids for the process step (XVII)→(XVIII) are boron trifluoride/diethyl ether complex, cerium(IV) ammonium nitrate (CAN), tin(II) chloride, lithium perchlorate, zinc(II) chloride, indium(III) chloride or indium(III) bromide. Preference is given to boron trifluoride/diethyl ether complex.

The reaction (XVII)→(XVIII) is generally carried out in a temperature range from −78° C. to +40° C., preferably at from 0° C. to +20° C. The reaction can be carried out at atmospheric pressure, at elevated pressure or at reduced pressure (for example at from 0.5 to 5 bar). In general, the reaction is carried out at atmospheric pressure.

Inert solvents for the reaction (XVIII)+(XIX)→(XX) are, for example, halogenated hydrocarbons such as dichloromethane, trichloromethane, carbon tetrachloride, trichloroethylene or chlorobenzene, ethers such as diethyl ether, dioxane, tetrahydrofuran, glycol dimethyl ether or diethylene glycol dimethyl ether, or other solvents such as dimethylformamide (DMF), dimethyl sulphoxide (DMSO), N,N'-dimethylpropyleneurea (DMPU), N-methylpyrrolidone (NMP), pyridine, acetonitrile. Preference is given to DMF.

Suitable bases for the process step (XVIII)+(XIX)→(XX) are alkali metal hydrides such as potassium hydride or sodium hydride, alkali metal carbonates such as lithium carbonate, sodium carbonate, potassium carbonate or caesium carbonate, alkali metal bicarbonates such as sodium bicarbonate or potassium bicarbonate, alkali metal alkoxides such as sodium methoxide or potassium methoxide, sodium ethoxide or potassium ethoxide or potassium tert-butoxide, amides such as sodium amide, lithium bis(trimethylsilyl)amide, sodium bis(trimethylsilyl)amide or potassium bis(trimethylsilyl)amide or lithium diisopropylamide, organometallic compounds such as butyllithium or phenyllithium, or organic amines such as triethylamine, diisopropylethylamine, pyridine, 1,8-diazabicyclo[5.4.0]undec-7-ene (DBU) or 1,5-diazabicyclo[4.3.0]non-5-ene (DBN). Preference is given to caesium carbonate.

The reaction (XVIII)+(XIX)→(XX) is generally carried out in a temperature range from 0° C. to +60° C., preferably at from +10° C. to +25° C. The reaction can be carried out at atmospheric pressure, at elevated pressure or at reduced pressure (for example at from 0.5 to 5 bar). In general, the reaction is carried out at atmospheric pressure.

Inert solvents for the process step (XX)→(XXI) are, for example, ethers such as diethyl ether, dioxane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulphoxide (DMSO), N,N'-dimethylpropyleneurea (DMPU), N-methylpyrrolidone (NMP), pyridine or acetonitrile. It is also possible to use mixtures of the solvents mentioned. Preference is given to DMSO.

The reaction (XX)→(XXI) is generally carried out in a temperature range from +20° C. to +180° C., preferably at from +100° C. to +160° C., if appropriate in a microwave. The reaction can be carried out at atmospheric pressure, at elevated pressure or at reduced pressure (for example at from 0.5 to 5 bar). In general, the reaction is carried out at atmospheric pressure.

The reaction (XXI)→(II) is carried out using methods known to the person silted in the art in a two-step process first with formation of the imino ester using sodium methoxide in methanol at 0° C. to +40° C. and subsequent nucleophilic addition of one equivalent of ammonia such as, for example, ammonia or ammonium chloride in a suitable acid with formation of the amidine (III) at from +50 to +150° C.

Suitable acids for the formation of the amidine (II) are inorganic acids such as, for example, hydrogen chloride/hydrochloric acid, sulphuric acid, polyphosphoric acid or phosphoric acid, or organic acids such as, for example, acetic acid, trifluoroacetic acid or formic acid. Preference is given to using hydrochloric acid or acetic acid.

The preparation process described can be illustrated in an exemplary manner by the synthesis scheme below (Scheme 7):

Scheme 7

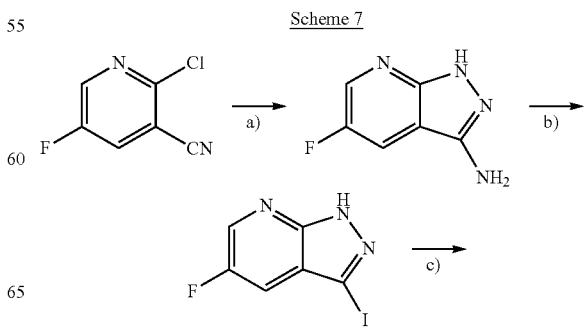

-continued

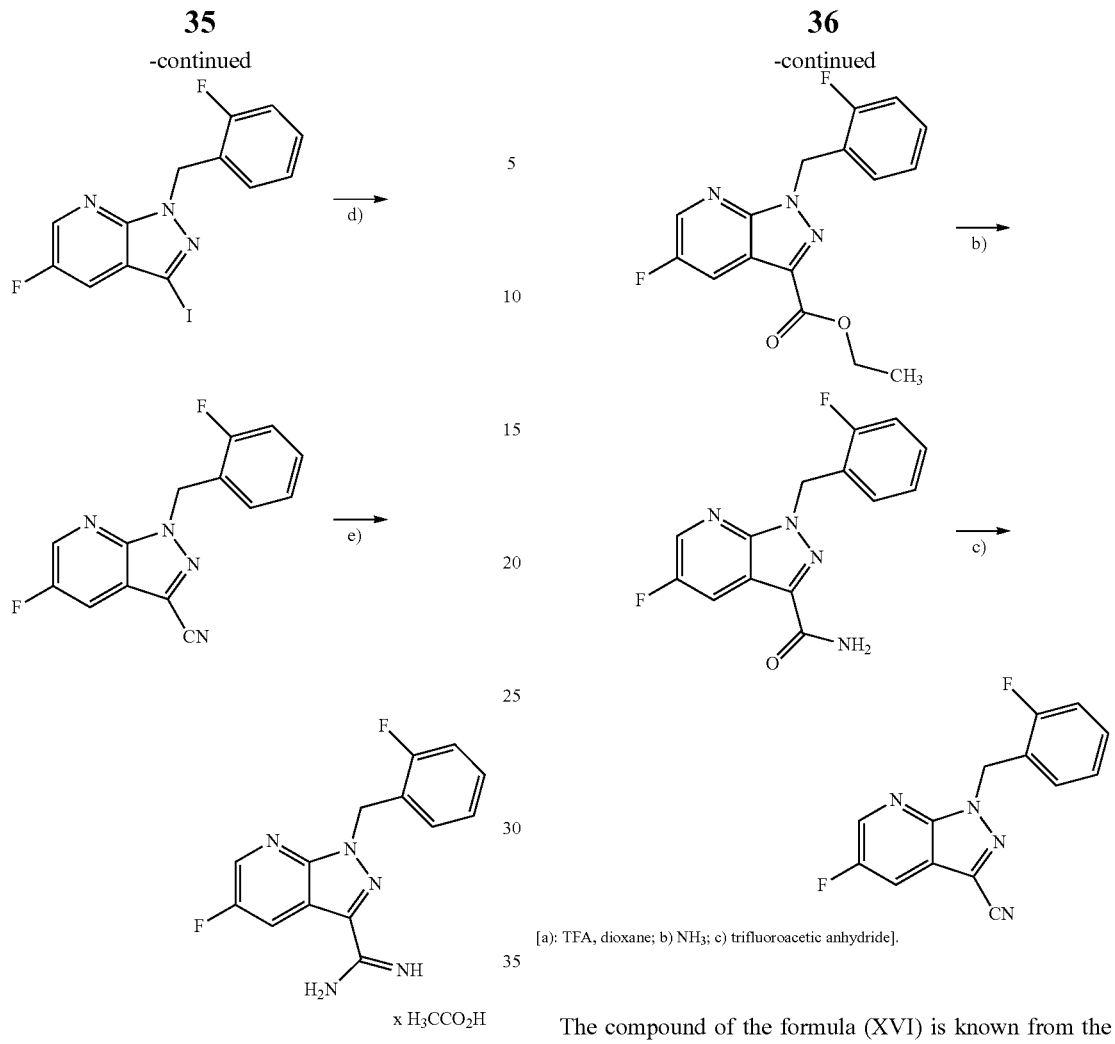

[a]: hydrazine hydrate, 1,2-ethanediol; b): isopentyl nitrite, NaI, THF; b): 2-fluorobenzyl bromide, Cs₂CO₃, DMF; d): CuCN, DMSO, e): 1. NaOME, MeOH, 2. NH₄Cl, acetic acid].

Alternatively, the preparation of the compounds of the formula (II) is carried out as shown in an exemplary manner in the synthesis scheme below (Scheme 13):

Scheme 13

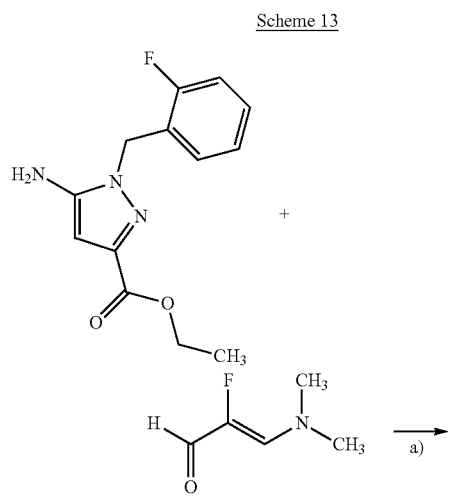

[a]: TFA, dioxane; b) NH₃; c) trifluoroacetic anhydride].

The compound of the formula (XVI) is known from the literature [cf., for example, Winn M., *J. Med. Chem.* 1993, 36, 2676-7688; EP 634 413-A1; CN 1613849-A; EP 1626045-A1; WO 2009/018415] or can be prepared analogously to procedures known from the literature or as shown in the synthesis scheme below (Scheme 8):

Scheme 8

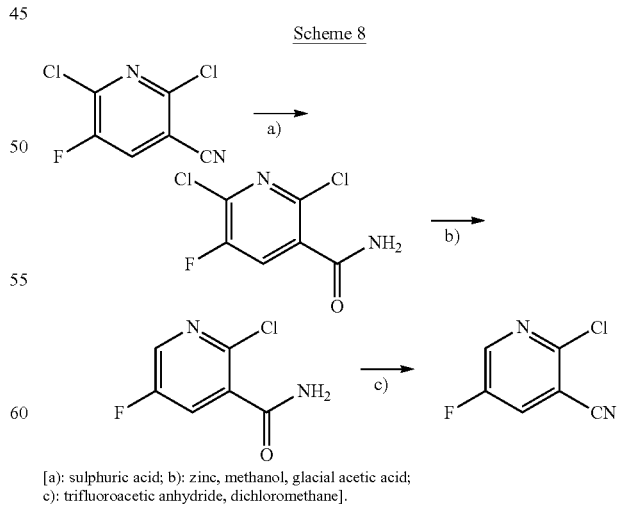

[a]: sulphuric acid; b): zinc, methanol, glacial acetic acid; c): trifluoroacetic anhydride, dichloromethane].

The compounds of the formulae (III) and (VI) are commercially available, known from the literature or can be prepared analogously to procedures known from the literature or as shown in an exemplary manner in the synthesis schemes below (Schemes 9 and 10):

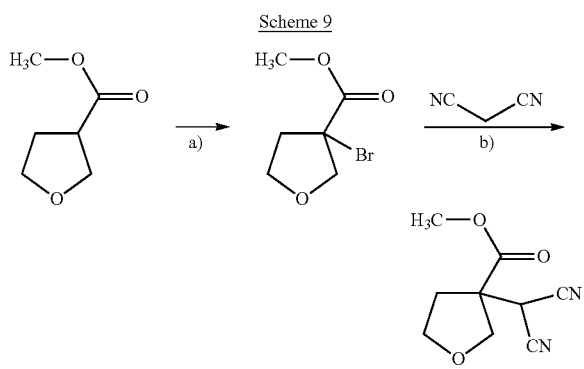

[a]: 1. LiHMDS, -78° C., THF, 2. NBS; b): NaH, 50° C., THF].

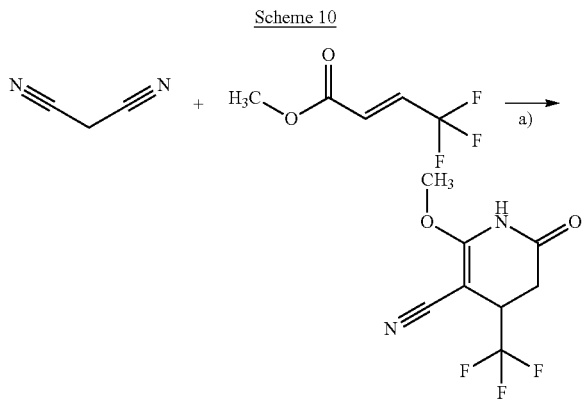

[a]: NaOMe, MeOH, 65° C.].

The compounds of the formulae (VII) and (XII) are commercially available, known from the literature or can be prepared analogously to procedures known from the literature.

The compounds according to the invention act as potent stimulators of soluble guanylate cyclase, possess valuable pharmacological properties, and have an improved therapeutic profile, for example with respect to their in vivo properties and/or their pharmacokinetic behaviour. They are therefore suitable for the treatment and prophylaxis of diseases in humans and animals.

The compounds according to the invention bring about vessel relaxation and inhibition of thrombocyte aggregation and lead to a lowering of blood pressure and to an increase in coronary blood flow. These effects are due to direct stimulation of soluble guanylate cyclase and an increase in intracellular cGMP. Moreover, the compounds according to the invention intensify the action of substances that raise the cGMP level, for example EDRF (endothelium-derived relaxing factor), NO donors, protoporphyrin IX, arachidonic acid or phenylhydrazine derivatives.

The compounds according to the invention are suitable for the treatment and prophylaxis of cardiovascular, pulmonary, thromboembolic and fibrotic diseases.

The compounds according to the invention can therefore be used in medicinal products for the treatment and prophylaxis of cardiovascular diseases, for example high blood pressure (hypertension), resistant hypertension, acute and chronic heart failure, coronary heart disease, stable and unstable angina pectoris, peripheral and cardiac vascular diseases, arrhythmias, disturbances of atrial and ventricular rhythm and conduction disturbances, for example atrioventricular blocks of degree I-III (AVB supraventricular tachyarrhythmia, atrial fibrillation, atrial flutter, ventricular fibrillation, ventricular flutter, ventricular tachyarrhythmia, torsade-de-pointes tachycardia, atrial and ventricular extrasystoles, AV-junction extrasystoles, sick-sinus syndrome, syncopes, AV-node reentry tachycardia, Wolff-Parkinson-White syndrome, acute coronary syndrome (ACS), autoimmune heart diseases (pericarditis, endocarditis, valvulitis, aortitis, cardiomyopathies), shock such as cardiogenic shock, septic shock and anaphylactic shock, aneurysms, Boxer cardiomyopathy (premature ventricular contraction (PVC)), for the treatment and prophylaxis of thromboembolic diseases and ischaemias such as myocardial ischaemia, myocardial infarction, stroke, cardiac hypertrophy, transient ischaemic attacks, preeclampsia, inflammatory cardiovascular diseases, spasms of the coronary arteries and peripheral arteries, development of oedema, for example pulmonary oedema, cerebral oedema, renal oedema or oedema due to heart failure, peripheral perfusion disturbances, reperfusion injury, arterial and venous thromboses, microalbuminuria, myocardial insufficiency, endothelial dysfunction, for preventing restenoses such as after thrombolysis therapies, percutaneous transluminal angioplasty (PTA), transluminal coronary angioplasty (PTCA), heart transplant and bypass operations, and micro- and macrovascular damage (vasculitis), increased level of fibrinogen and of low-density LDL and increased concentrations of plasminogen activator inhibitor 1 (PAI-1), and for the treatment and prophylaxis of erectile dysfunction and female sexual dysfunction.

In the sense of the present invention, the term heart failure comprises both acute and chronic manifestations of heart failure, as well as more specific or related forms of disease such as acute decompensated heart failure, right ventricular failure, left ventricular failure, total heart failure, ischaemic cardiomyopathy, dilatated cardiomyopathy, hypertrophic cardiomyopathy, idiopathic cardiomyopathy, congenital heart defects, heart failure with valvular defects, mitral valve stenosis, mitral valve insufficiency, aortic valve stenosis, aortic valve insufficiency, tricuspid stenosis, tricuspid insufficiency, pulmonary valve stenosis, pulmonary valve insufficiency, combined valvular defects, heart muscle inflammation (myocarditis), chronic myocarditis, acute myocarditis, viral myocarditis, diabetic heart failure, alcoholic cardiomyopathy, storage cardiomyopathies, diastolic heart failure and systolic heart failure.

In addition, the compounds according to the invention can also be used for the treatment and prophylaxis of arteriosclerosis, disturbances of lipid metabolism, hypolipoproteinaemias, dyslipidaemias, hypertriglyceridaemias, hyperlipidaemias, hypercholesterolaemias, abetalipoproteinaemia, sitosterolaemia, xanthomatosis, Tangier disease, adiposity, obesity, and combined hyperlipidaemias and metabolic syndrome.

Moreover, the compounds according to the invention can be used for the treatment and prophylaxis of primary and secondary Raynaud phenomenon, microcirculation disturbances, claudication, peripheral and autonomic neuropathies, diabetic microangiopathies, diabetic retinopathy, diabetic limb ulcers, gangrene, CREST syndrome, erythematous disorders, onychomycosis, rheumatic diseases and for promoting wound healing.

Furthermore, the compounds according to the invention are suitable for treating urological diseases, for example benign prostatic syndrome (BPS), benign prostatic hyperplasia (BPH), benign prostatic enlargement (BPE), bladder outlet obstruction (BOO), lower urinary tract syndromes (LUTS, including feline urological syndrome (FUS)), diseases of the urogenital system including neurogenic overactive bladder (OAB) and (IC), urinary incontinence (UI) for example mixed, urge, stress, or overflow incontinence (MUI, UUI, SUI, OUI), pelvic pains, benign and malignant diseases of the organs of the male and female urogenital system.

Furthermore, the compounds according to the invention are suitable for the treatment and prophylaxis of kidney diseases, in particular acute and chronic renal insufficiency, and acute and chronic renal failure. In the sense of the present invention, the term renal insufficiency comprises both acute and chronic manifestations of renal insufficiency, as well as underlying or related kidney diseases such as renal hypoperfusion, intradialytic hypotension, obstructive uropathy, glomerulopathies, glomerulonephritis, acute glomerulonephritis, glomerulosclerosis, tubulointerstitial diseases, nephropathic diseases such as primary and congenital kidney disease, nephritis, immunological kidney diseases such as kidney transplant rejection, immune complex-induced kidney diseases, nephropathy induced by toxic substances, contrast medium-induced nephropathy, diabetic and non-diabetic nephropathy, pyelonephritis, renal cysts, nephrosclerosis, hypertensive nephrosclerosis and nephrotic syndrome, which can be characterized diagnostically for example by abnormally reduced creatinine and/or water excretion, abnormally increased blood concentrations of urea, nitrogen, potassium and/or creatinine, altered activity of renal enzymes such as e.g. glutamyl synthetase, altered urine osmolarity or urine volume, increased microalbuminuria, macroalbuminuria, lesions of glomeruli and arterioles, tubular dilatation, hyperphosphataemia and/or need for dialysis. The present invention also comprises the use of the compounds according to the invention for the treatment and prophylaxis of sequelae of renal insufficiency, for example pulmonary oedema, heart failure, uraemia, anaemia, electrolyte disturbances (e.g. hyperkalaemia, hyponatraemia) and disturbances in bone and carbohydrate metabolism.

Furthermore, the compounds according to the invention are also suitable for the treatment and prophylaxis of asthmatic diseases, pulmonary arterial hypertension (PAH) and other forms of pulmonary hypertension (PH), comprising pulmonary hypertension associated with left ventricular disease, HIV, sickle cell anaemia, thromboembolism (CTEPH), sarcoidosis, COPD or pulmonary fibrosis, chronic obstructive pulmonary disease (COPD), acute respiratory distress syndrome (ARDS), acute lung injury (ALI), alpha-1-antitrypsin deficiency (AATD), pulmonary fibrosis, pulmonary emphysema (e.g. smoking-induced pulmonary emphysema) and cystic fibrosis (CF).

The compounds described in the present invention are also active substances for controlling diseases in the central nervous system that are characterized by disturbances of the NO/cGMP system. In particular, they are suitable for improving perception, capacity for concentration, capacity for learning or memory performance after cognitive disturbances, such as occur in particular in situations/diseases/syndromes such as mild cognitive impairment, age-related learning and memory disturbances, age-related memory loss, vascular dementia, head injury, stroke, post-stroke dementia, post-traumatic head injury, general disturbances of concentration, disturbances of concentration in children with learning and memory problems, Alzheimer's disease, Lewy body dementia, dementia with frontal lobe degeneration including Pick's syndrome, Parkinson's disease, progressive nuclear palsy, dementia with corticobasal degeneration, amyotrophic lateral sclerosis (ALS), Huntington's disease, demyelination, multiple sclerosis, thalamic degeneration, Creutzfeldt-Jakob dementia, HIV-dementia, schizophrenia with dementia or Korsakoff psychosis. They are also suitable for the treatment and prophylaxis of diseases of the central nervous system such as anxiety, tension and depression, CNS-related sexual dysfunctions and sleep disturbances and for controlling pathological eating disorders and use of luxury foods and addictive drugs.

Furthermore, the compounds according to the invention are also suitable for controlling cerebral perfusion and are effective agents for combating migraines. They are also suitable for the prophylaxis and control of consequences of cerebral infarctions (apoplexia cerebri) such as stroke, cerebral ischaemias and head injury. The compounds according to the invention can also be used for controlling pain states and tinnitus.

In addition, the compounds according to the invention possess anti-inflammatory action and can therefore be used as anti-inflammatory agents for the treatment and prophylaxis of sepsis (SIRS), multiple organ failure (MODS, MOF), inflammatory diseases of the kidney, chronic intestinal inflammations (IBD, Crohn's disease, UC), pancreatitis, peritonitis, rheumatoid diseases, inflammatory skin diseases and inflammatory eye diseases.

Moreover, the compounds according to the invention can also be used for the treatment and prophylaxis of autoimmune diseases.

Furthermore, the compounds according to the invention are suitable for the treatment and prophylaxis of fibrotic diseases of the internal organs, for example of the lung, heart, kidney, bone marrow and in particular of the liver, and dermatological fibroses and fibrotic diseases of the eye. In the sense of the present invention, the term fibrotic diseases comprises in particular the following terms: hepatic fibrosis, hepatic cirrhosis, pulmonary fibrosis, endomyocardial fibrosis, nephropathy, glomerulonephritis, interstitial renal fibrosis, fibrotic lesions as a consequence of diabetes, bone marrow fibrosis and similar fibrotic diseases, scleroderma, morphea, keloids, hypertrophic scars (including after surgery), naevi, diabetic retinopathy, proliferative vitreoretinopathy and connective tissue diseases (e.g. sarcoidosis).

Furthermore, the compounds according to the invention are suitable for controlling postoperative scarring, e.g. as a result of glaucoma operations.

The compounds according to the invention can also be used cosmetically for ageing and keratinizing skin.

Moreover, the compounds according to the invention are suitable for the treatment and prophylaxis of hepatitis, neoplasms, osteoporosis, glaucoma and gastroparesis.

The present invention further relates to the use of the compounds according to the invention for the treatment and prophylaxis of diseases, in particular the aforementioned diseases.

The present invention further relates to the use of the compounds according to the invention for the treatment and prophylaxis of heart failure, angina pectoris, hypertension, pulmonary hypertension, ischaemias, vascular diseases, renal insufficiency, thromboembolic diseases, fibrotic diseases and arteriosclerosis.

The present invention further relates to the compounds according to the invention for use in a method for the treatment and prophylaxis of heart failure, angina pectoris, hypertension, pulmonary hypertension, ischaemias, vascular diseases, renal insufficiency, thromboembolic diseases, fibrotic diseases and arteriosclerosis.

The present invention further relates to the use of the compounds according to the invention for producing a medicinal product for the treatment and prophylaxis of diseases, in particular the aforementioned diseases.

The present invention further relates to the use of the compounds according to the invention for producing a medicinal product for the treatment and prophylaxis of heart failure, angina pectoris, hypertension, pulmonary hypertension, ischaemias, vascular diseases, renal insufficiency, thromboembolic diseases, fibrotic diseases and arteriosclerosis.

The present invention further relates to a method for the treatment and prophylaxis of diseases, in particular the aforementioned diseases, using an effective amount of at least one of the compounds according to the invention.

The present invention further relates to a method for the treatment and prophylaxis of heart failure, angina pectoris, hypertension, pulmonary hypertension, ischaemias, vascular diseases, renal insufficiency, thromboembolic diseases, fibrotic diseases and arteriosclerosis, using an effective amount of at least one of the compounds according to the invention.

The compounds according to the invention can be used alone or in combination with other active substances if necessary. The present invention further relates to medicinal products containing at least one of the compounds according to the invention and one or more further active substances, in particular for the treatment and prophylaxis of the aforementioned diseases. As suitable combination active substances, we may mention for example and preferably:

organic nitrates and NO-donors, for example sodium nitroprusside, nitroglycerin, isosorbide mononitrate, isosorbide dinitrate, molsidomine or SIN-1, and inhalational NO;

compounds that inhibit the degradation of cyclic guanosine monophosphate (cGMP), for example inhibitors of phosphodiesterases (PDE) 1, 2 and/or 5, in particular PDE-5 inhibitors such as sildenafil, vardenafil and tadalafil;

antithrombotic agents, for example and preferably from the group of platelet aggregation inhibitors, anticoagulants or profibrinolytic substances;

active substances for lowering blood pressure, for example and preferably from the group of calcium antagonists, angiotensin AII antagonists, ACE inhibitors, endothelin antagonists, renin inhibitors, alpha-blockers, beta-blockers, mineralocorticoid receptor antagonists and diuretics; and/or active substances that alter fat metabolism, for example and preferably from the group of thyroid receptor agonists, cholesterol synthesis inhibitors such as for example and preferably HMG-CoA-reductase or squalene synthesis inhibitors, ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbers, bile acid reabsorption inhibitors and lipoprotein(a) antagonists.

Antithrombotic agents are preferably to be understood as compounds from the group of platelet aggregation inhibitors, anticoagulants or profibrinolytic substances.

In a preferred embodiment of the invention, the compounds according to the invention are administered in combination with a platelet aggregation inhibitor, for example and preferably aspirin, clopidogrel, ticlopidine or dipyridamole.

In a preferred embodiment of the invention, the compounds according to the invention are administered in combination with a thrombin inhibitor, for example and preferably ximelagatran, dabigatran, melagatran, bivalirudin or Clexane.

In a preferred embodiment of the invention, the compounds according to the invention are administered in combination with a GPIIb/IIIa antagonist, for example and preferably tirofiban or abciximab.

In a preferred embodiment of the invention, the compounds according to the invention are administered in combination with a factor Xa inhibitor, for example and preferably rivaroxaban (BAY 59-7939), DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or a low molecular weight (LMW) heparin derivative.

In a preferred embodiment of the invention, the compounds according to the invention are administered in combination with a vitamin K antagonist, for example and preferably coumarin.

The agents for lowering blood pressure are preferably to be understood as compounds from the group of calcium antagonists, angiotensin AII antagonists, ACE inhibitors, endothelin antagonists, renin inhibitors, alpha-blockers, beta-blockers, mineralocorticoid-receptor antagonists and diuretics.

In a preferred embodiment of the invention, the compounds according to the invention are administered in combination with a calcium antagonist, for example and preferably nifedipine, amlodipine, verapamil or diltiazem.

In a preferred embodiment of the invention, the compounds according to the invention are administered in combination with an alpha-1-receptor blocker, for example and preferably prazosin.

In a preferred embodiment of the invention, the compounds according to the invention are administered in combination with a beta-blocker, for example and preferably propranolol, atenolol, timolol, pindolol, alprenolol, oxprenolol, penbutolol, bupranolol, metipranolol, nadolol, mepindolol, carazolol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AII antagonist, for example and preferably losartan, candesartan, valsartan, telmisartan or embursatan.

In a preferred embodiment of the invention, the compounds according to the invention are administered in combination with an ACE inhibitor, for example and preferably enalapril, captopril, lisinopril, ramipril, delapril, fosinopril, quinopril, perindopril or trandopril.

In a preferred embodiment of the invention, the compounds according to the invention are administered in combination with an endothelin antagonist, for example and preferably bosentan, darusentan, ambrisentan or sitaxsentan.

In a preferred embodiment of the invention, the compounds according to the invention are administered in combination with a renin inhibitor, for example and preferably aliskiren, SPP-600 or SPP-800.

In a preferred embodiment of the invention, the compounds according to the invention are administered in combination with a mineralocorticoid-receptor antagonist, for example and preferably spironolactone or eplerenone.

In a preferred embodiment of the invention, the compounds according to the invention are administered in combination with a loop diuretic, for example furosemide, torasemide, bumetanide and piretanide, with potassium-sparing diuretics for example amiloride and triamterene, with aldosterone antagonists, for example spironolactone, potassium canrenoate and eplerenone and thiazide diuretics, for example hydrochlorothiazide, chlorthalidone, xipamide, and indapamide.

Agents altering fat metabolism are preferably to be understood as compounds from the group of CETP inhibitors, thyroid receptor agonists, cholesterol synthesis inhibitors such as HMG-CoA-reductase or squalene synthesis inhibitors, the ACAT inhibitors, MTP inhibitors, PPAR-alpha, PPAR-gamma and/or PPAR-delta agonists, cholesterol-absorption inhibitors, polymeric bile acid adsorbers, bile acid reabsorption inhibitors, lipase inhibitors and the lipoprotein (a) antagonists.

In a preferred embodiment of the invention, the compounds according to the invention are administered in combination with a CETP inhibitor, for example and preferably dalcetrapib, BAY 60-5521, anacetrapib or CETP-vaccine (CETi-1).

In a preferred embodiment of the invention, the compounds according to the invention are administered in combination with a thyroid receptor agonist, for example and preferably D-thyroxin, 3,5,3'-triiodothyronin (T3), CGS 23425 or axitirome (CGS 26214).

In a preferred embodiment of the invention, the compounds according to the invention are administered in combination with a HMG-CoA-reductase inhibitor from the class of statins, for example and preferably lovastatin, simvastatin, pravastatin, fluvastatin, atorvastatin, rosuvastatin or pitavastatin.

In a preferred embodiment of the invention, the compounds according to the invention are administered in combination with a squalene synthesis inhibitor, for example and preferably BMS-188494 or TAK-475.

In a preferred embodiment of the invention, the compounds according to the invention are administered in combination with an ACAT inhibitor, for example and preferably avasimibe, melinamide, pactimibe, eflucimibe or SMP-797.

In a preferred embodiment of the invention, the compounds according to the invention are administered in combination with an MTP inhibitor, for example and preferably implitapide, BMS-201038, R-103757 or JTT-130.

In a preferred embodiment of the invention, the compounds according to the invention are administered in combination with a PPAR-gamma agonist, for example and preferably pioglitazone or rosiglitazone.

In a preferred embodiment of the invention, the compounds according to the invention are administered in combination with a PPAR-delta agonist, for example and preferably GW 501516 or BAY 68-5042.

In a preferred embodiment of the invention, the compounds according to the invention are administered in combination with a cholesterol-absorption inhibitor, for example and preferably ezetimibe, tiqueside or pamaqueside.

In a preferred embodiment of the invention, the compounds according to the invention are administered in combination with a lipase inhibitor, for example and preferably orlistat.

In a preferred embodiment of the invention, the compounds according to the invention are administered in combination with a polymeric bile acid adsorber, for example and preferably cholestyramine, colestipol, colesolvam, CholestaGel or colestimide.

In a preferred embodiment of the invention, the compounds according to the invention are administered in combination with a bile acid reabsorption inhibitor, for example and preferably ASBT (=IBAT) inhibitors, e.g. AZD-7806, S-8921, AK-105, BARI-1741, SC-435 or SC-635.

In a preferred embodiment of the invention, the compounds according to the invention are administered in combination with a lipoprotein(a) antagonist, for example and preferably gemcabene calcium (CI-1027) or nicotinic acid.

The present invention further relates to medicinal products that contain at least one compound according to the invention, usually together with one or more inert, non-toxic, pharmaceutically suitable excipients, and use thereof for the aforementioned purposes.

The compounds according to the invention can have systemic and/or local action. For this purpose they can be applied in a suitable way, e.g. by oral, parenteral, pulmonary, nasal, sublingual, lingual, buccal, rectal, dermal, transdermal, conjunctival, or otic administration or as implant or stent.

For these routes of application, the compounds according to the invention can be administered in suitable dosage forms.

Dosage forms functioning according to the prior art, for rapid and/or modified release of the compounds according to the invention, which contain the compounds according to the invention in crystalline and/or amorphized and/or dissolved form, e.g. tablets (uncoated or coated tablets, for example with enteric coatings or coatings with delayed dissolution or insoluble coatings, which control the release of the compound according to the invention), tablets or films/wafers that disintegrate rapidly in the oral cavity, films/lyophilizates, capsules (for example hard or soft gelatin capsules), sugar-coated pills, granules, pellets, powders, emulsions, suspensions, aerosols or solutions, are suitable for oral application.

Parenteral application can take place avoiding an absorption step (e.g. intravenous, intraarterial, intracardiac, intraspinal or intralumbar) or including absorption (e.g. intramuscular, subcutaneous, intracutaneous, percutaneous or intraperitoneal). Injection and infusion preparations in the form of solutions, suspensions, emulsions, lyophilizates or sterile powders are suitable, among others, as dosage forms for parenteral application.

Inhaled pharmaceutical forms (including powder inhalers, nebulizers), nasal drops, solutions or sprays, tablets, films/wafers or capsules for lingual, sublingual or buccal application, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, dusting powders, implants or stents for example are suitable for other routes of administration.

Oral or parenteral application is preferred, especially oral application.

The compounds according to the invention can be transformed to the aforementioned dosage forms. This can take place in a manner known per se by mixing with inert, non-toxic, pharmaceutically suitable excipients. These excipients include inter alia carriers (for example microcrystalline cellulose, lactose, mannitol), solvents (e.g. liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (e.g. antioxidants such as ascorbic acid), colorants (e.g. inorganic pigments, for example iron oxides) and taste and/or odour correctants.

In general, it has proved advantageous, in the case of parenteral application, to administer amounts of about 0.001 to 1 mg/kg, preferably about 0.01 to 0.5 mg/kg body weight to achieve effective results. For oral application, the dosage is about 0.01 to 100 mg/kg, preferably about 0.01 to 20 mg/kg body weight and very particularly preferably 0.1 to 10 mg/kg body weight.

Nevertheless, it may optionally be necessary to deviate from the stated amounts, namely depending on body weight, route of application, individual response to the active substance, type of preparation and time point or interval when application takes place. Thus, in some cases it may be sufficient to use less than the aforementioned minimum amount, whereas in other cases the stated upper limit must be exceeded. When applying larger amounts, it may be advisable to distribute these in several individual doses throughout the day.

The following practical examples explain the invention. The invention is not limited to the examples.

The percentages in the following tests and examples are percentages by weight, unless stated otherwise; parts are parts by weight. Proportions of solvents, dilution ratios and concentrations for liquid/liquid solutions refer in each case to the volume.

A. EXAMPLES

Abbreviations and Acronyms
aq. aqueous solution
calc. calculated
DCI direct chemical ionization (in MS)
DMF dimethylformamide
DMSO dimethyl sulphoxide
eq. equivalent(s)
ESI electrospray ionization (in MS)
Et ethyl
h hour(s)
HPLC high-performance liquid chromatography
HRMS high-resolution mass spectrometry
conc. concentrated
LC/MS liquid chromatography-coupled mass spectrometry
LiHMDS lithium hexamethyl disilazide
Me methyl
min minute(s)
MS mass spectrometry
NMR nuclear magnetic resonance spectrometry
Pd/C palladium on activated charcoal (10%)
Ph phenyl
RT room temperature
$R_t$ retention time (in HPLC)
t-Bu tert-butyl
TFA trifluoroacetic acid
THF tetrahydrofuran
UV ultraviolet spectrometry
v/v volume to volume ratio (of a solution)
XPHOS dicyclohexyl-(2',4',6'-triisopropylbiphenyl-2-yl)-phosphine
LC/MS Methods:
Method 1 (LC-MS):
Instrument: Waters ACQUITY SQD UPLC system; column: Waters Acquity UPLC HSS T3 1.8μ 50×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; oven: 50° C.; flow rate: 0.40 ml/min; UV detection: 210-400 nm.
Method 2 (LC-MS):
MS instrument type: Waters ZQ; HPLC instrument type: Agilent 1100 Series; UV DAD; column: Thermo Hypersil GOLD 3μ 20 mm×4 mm; mobile phase A: 1 l of water+0.5 ml of 50% strength formic acid, mobile phase B: 1 l of acetonitrile+0.5 ml of 50% strength formic acid; gradient: 0.0 min 100% A→3.0 min 10% A→4.0 min 10% A, oven: 55° C.; flow rate 2 ml/min; UV detection: 210 nm.
Method 3 (LC-MS):
Instrument: Micromass Quattro Premier with Waters UPLC Acquity; column: Thermo Hypersil GOLD 1.9μ 50×1 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→1.5 min 10% A→2.2 min 10% A oven: 50° C.; flow rate: 0.33 ml/min; UV detection: 210 nm.
Method 4 (LC-MS):
Instrument: Waters ACQUITY SQD UPLC system; column: Waters Acquity UPLC HSS T3 1.8μ 30×2 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A oven: 50° C.; flow rate: 0.60 ml/min; UV detection: 208-400 nm.
Starting Materials and Intermediates:

Example 1A 1-(2-Fluorobenzyl)-1H-pyrazolo[3,4-b]pyridine-3-carboximidamide hydrochloride

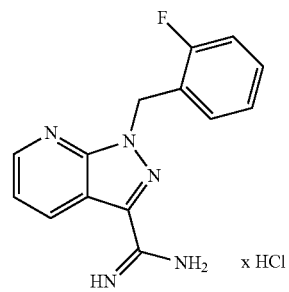 [SMILES: N=C(N)c1nn(Cc2ccccc2F)c2ncccc12]

The synthesis of this compound is described in WO 03/095451, Example 6A.

Example 2A 2,6-Dichloro-5-fluoronicotinamide

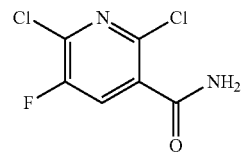 [SMILES: NC(=O)c1cc(F)c(Cl)nc1Cl]

A suspension of 25 g (130.90 mmol) of 2,6-dichloro-5-fluoro-3-cyanopyridine in conc. sulphuric acid (125 ml) was stirred at 60-65° C. for 1 h. After cooling to RT, the contents of the flask were poured into ice-water and extracted three times with ethyl acetate (100 ml each). The combined organic phases were washed with water (100 ml) and then washed with saturated aqueous sodium bicarbonate solution (100 ml), dried and concentrated on a rotary evaporator. The material obtained was dried under high vacuum.

Yield: 24.5 g (90% of theory)

$^1$H NMR (400 MHz, DMSO-$d_6$): δ=7.95 (br s, 1H), 8.11 (br s, 1H), 8.24 (d, 1H).

Example 3A

2-Chloro-5-fluoronicotinamide

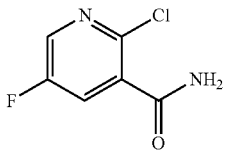

At RT, 44 g (210.58 mmol) of 2,6-dichloro-5-fluoronicotinamide were added to a suspension of 21.9 g (335.35 mmol) of zinc in methanol (207 ml). Acetic acid (18.5 ml) was then added, and the mixture was heated at reflux with stirring for 24 h. The contents of the flask were then decanted from the zinc, ethyl acetate (414 ml) and saturated aqueous sodium bicarbonate solution (414 ml) were added and the mixture was stirred vigorously. The mixture was then filtered off with suction through kieselguhr and washed three times with ethyl acetate (517 ml each). The organic phase was separated off and the aqueous phase was washed with ethyl acetate (258 ml). The combined organic phases were washed once with saturated aqueous sodium bicarbonate solution (414 ml), dried and concentrated under reduced pressure. Dichloromethane (388 ml) was added to the crystals obtained in this manner, and the crystals were triturated for 20 min. The crystals were once more filtered off with suction and washed with diethyl ether and sucked dry.

Yield: 20.2 g (53% of theory)

$^1$H NMR (400 MHz, DMSO-$d_6$): δ=7.87 (br s, 1H), 7.99 (dd, 1H), 8.10 (br s, 1H), 8.52 (d, 1H).

Example 4A

2-Chloro-5-fluoronicotinonitrile

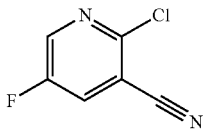

81.2 ml (582.25 mmol) of triethylamine were added to a suspension of 46.2 g (264.66 mmol) of 2-chloro-5-fluoronicotinamide in dichloromethane (783 ml), and the mixture was cooled to 0° C. With stirring, 41.12 ml (291.13 mmol) of trifluoroacetic anhydride were then slowly added dropwise, and the mixture was stirred at 0° C. for another 1.5 h. The reaction solution was then washed twice with saturated aqueous sodium bicarbonate solution (391 ml each), dried and concentrated under reduced pressure.

Yield: 42.1 g (90% of theory).

$^1$H NMR (400 MHz, DMSO-$d_6$): δ=8.66 (dd, 1H), 8.82 (d, 1H).

Example 5A

5-Fluoro-1H-pyrazolo[3,4-b]pyridine-3-amine

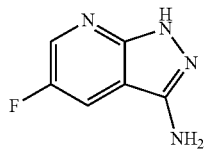 [SMILES: Nc1n[nH]c2ncc(F)cc12]

A suspension of 38.5 g (245.93 mmol) of 2-chloro-5-fluoronicotinonitrile was initially charged in 1,2-ethanediol (380 ml), and hydrazine hydrate (119.6 ml) was then added. With stirring, the mixture was heated at reflux for 4 h. On cooling, the product precipitated out. Water (380 ml) was added to the crystals, and the mixture was stirred at RT for 10 min. The suspension was then filtered off with suction through a frit and washed with water (200 ml) and with −10° C.-cold THF (200 ml). Drying under high vacuum over phosphorus pentoxide.

Yield: 22.8 g (61% of theory)

$^1$H NMR (400 MHz, DMSO-$d_6$): δ=5.54 (s, 2H), 7.96 (dd, 1H), 8.38 (m, 1H), 12.07 (m, 1H).

Example 6A

5-Fluoro-3-iod-1H-pyrazolo[3,4-b]pyridine

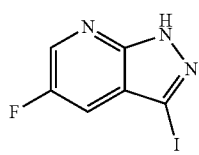

10 g (65.75 mmol) of 5-fluoro-1H-pyrazolo[3,4-b]pyridine-3-amine were initially charged in THF (329 ml), and the mixture was cooled to 0° C. 16.65 ml (131.46 mmol) of boron trifluoride/diethyl ether complex were then added slowly. The reaction mixture was cooled further to −10° C. A solution of 10.01 g (85.45 mmol) of isopentyl nitrite in THF (24.39 ml) was then added slowly, and the mixture was stirred for a further 30 min. The mixture was diluted with cold diethyl ether (329 ml) and the resulting solid was filtered off. The diazonium salt prepared in this manner was added a little at a time into a solution of 12.81 g (85.45 mmol) of sodium iodide in acetone (329 ml) at 0° C., and the mixture was stirred at RT for 30 min. The reaction mixture was added to ice-water (1.8 l) and extracted twice with ethyl acetate (487 ml each). The collected organic phases were washed with saturated aqueous sodium chloride solution (244 ml), dried, filtered and concentrated. This gave 12.1 g (86% pure, 60% of theory) of the title compound as a solid. The crude product was reacted without further purification.

LC-MS (Method 2): $R_t$=1.68 min

MS (ESIpos): m/z=264 (M+H)+

Example 7A

5-Fluoro-1-(2-fluorobenzyl)-3-iodo-1H-pyrazolo[3,4-b]pyridine

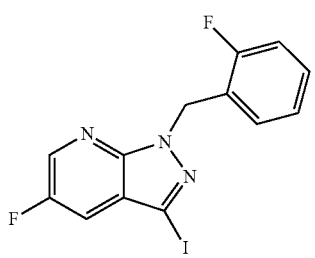 [SMILES: Fc1cnc2c(c1)c(I)nn2Cc1ccccc1F]

12.1 g (about 39.65 mmol) of the compound from Example 6A were initially charged in DMF (217 ml), and 8.25 g (43.62 mmol) of 2-fluorobenzyl bromide and 14.21 g (43.62 mmol) of caesium carbonate were then added. The mixture was stirred at RT for two hours. The reaction mixture was then added to water (1.17 l) and extracted twice with ethyl acetate (502 ml). The collected organic phases were washed with saturated aqueous sodium chloride solution (335 ml), dried, filtered and concentrated. The residue was chromatographed on silica gel (mobile phase:petroleum ether/ethyl acetate 97:3) and the product fractions were concentrated. This gave 9.0 g (61% of theory) of the title compound as a solid. The solid was taken up in ethyl acetate and washed with 10% strength aqueous sodium thiosulphate solution and then with saturated aqueous sodium chloride solution, dried and concentrated.

LC-MS (Method 2): $R_t$=2.57 min
MS (ESIpos): m/z=372 (M+H)$^+$
1H NMR (400 MHz, DMSO-d6): δ=5.73 (s, 2H), 7.13-7.26 (m, 3H), 7.33-7.41 (m, 1H), 7.94 (dd, 1H), 8.69-8.73 (m, 1H).

Example 8A

5-Fluoro-1-(2-fluorobenzyl)-1H-pyrazolo[3,4-b]pyridine-3-carbonitrile

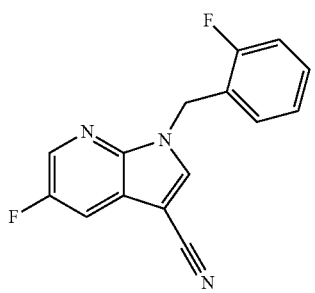 [SMILES: N#Cc1cn(Cc2ccccc2F)c2ncc(F)cc12]

A suspension of 16.03 g (43.19 mmol) of 5-fluoro-1-(2-fluorobenzyl)-3-iodo-1H-pyrazolo[3,4-b]pyridine (Example 7A) and 4.25 g (47.51 mmol) of copper cyanide was initially charged in DMSO (120 ml) and stirred at 150° C. for 2 h. After cooling, the contents of the flask were cooled to about 40° C., poured into a solution of conc. ammonia water (90 ml) and water (500 ml), ethyl acetate (200 ml) was added and the mixture was stirred briefly. The aqueous phase was separated off and extracted two more times with ethyl acetate (200 ml each). The combined organic phases were washed twice with 10% strength aqueous sodium chloride solution (100 ml each), dried and concentrated under reduced pressure. The crude product was reacted without further purification.

Yield: 11.1 g (91% of theory)
$^1$H NMR (400 MHz, DMSO-d$_6$): δ=5.87 (s, 2H), 7.17-7.42 (m, 4H), 8.52 (dd, 1H), 8.87 (dd, 1H).

Example 9A

5-Fluoro-1-(2-fluorobenzyl)-1H-pyrazolo[3,4-b]pyridine-3-carboximidamide acetate

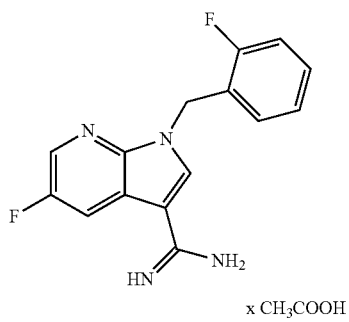 [SMILES: N=C(N)c1cn(Cc2ccccc2F)c2ncc(F)cc12]

11.1 g (41.07 mmol) of 5-fluoro-1-(2-fluorobenzyl)-1H-pyrazolo[3,4-b]pyridine-3-carbonitrile (Example 8A) were added to 2.22 g (41.07 mmol) of sodium methoxide in methanol (270 ml), and the mixture was stirred at RT for 2 h. 2.64 g (49.29 mmol) of ammonium chloride and acetic acid (9.17 ml) were added, and the mixture was heated at reflux overnight. The mixture was then concentrated to dryness, and the residue was taken up in water (100 ml) and ethyl acetate (100 ml) and adjusted to pH 10 with 2 N aqueous sodium hydroxide solution. The mixture was stirred at RT for about 1 h. The resulting suspension was filtered off with suction and washed with ethyl acetate (100 ml), water (100 ml) and once more with ethyl acetate (100 ml). The residue was dried over phosphorus pentoxide under high vacuum.

Yield: 9.6 g (78% of theory)
MS (ESIpos): m/z=288 (M+H)$^+$
1H NMR (400 MHz, DMSO-d$_6$): δ=1.85 (s, 3H), 5.80 (s, 2H), 7.14-7.25 (m, 3H), 7.36 (m, 1H), 8.42 (dd, 1H), 8.72 (dd, 1H).

Example 10A

Methyl 3,3-dicyano-2,2-dimethylpropanoate

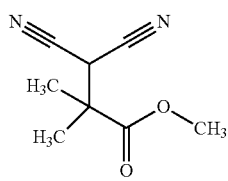

3 g (45.411 mmol) of malononitrile were added slowly to 1.816 g (45.411 mmol) of sodium hydride (60% in mineral oil) in THF (91 ml). 5.876 ml (45.411 mmol) of methyl 2-bromo-2-methylpropanoate were then added, and the mixture was stirred at RT overnight. Another 5.876 ml (45.411 mmol) of methyl 2-bromo-2-methylpropanoate were then added, and the mixture was heated at 50° C. overnight. Another 1.762 ml (13.623 mmol) of methyl 2-bromo-2-methylpropanoate were then added, and the mixture was heated at 50° C. for another 4 h. Saturated aqueous sodium bicarbonate solution was then added, and the mixture was extracted three times with ethyl acetate. The combined organic phases were washed with saturated aqueous sodium chloride solution, dried with sodium sulphate, filtered and concentrated to dryness. This gave 8.9 g of crude product which was purified by chromatography on silica gel (cyclohexane/ethyl acetate 4:1).

Yield: 6.47 g (85% of theory)

1H NMR (400 MHz, DMSO-d6): δ [ppm]=1.40 (s, 6H), 3.74 (s, 3H), 5.27 (s, 1H).

Example 11A

Methyl 3-bromotetrahydrofuran-3-carboxylate

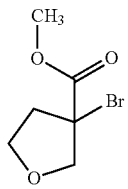

5.0 g (38.419 mmol) of methyl tetrahydrofuran-3-carboxylate (Journal of Organic Chemistry; 1996; 2690) were dissolved in 200 ml of THF and cooled to −78° C., and 76.83 ml (76.83 mmol) of bis(trimethylsilyl)lithium amide (1 M in THF) were then added. After 30 min at −78° C., 10.26 g (57.63 mmol) of N-bromosuccinimide, suspended in 50 ml of THF, were added slowly. The mixture was then allowed to warm to RT overnight. Water was added, and the mixture was extracted with ethyl acetate. The phases were separated and the aqueous phase was extracted two more times with ethyl acetate. The combined organic phases were washed with saturated aqueous sodium chloride solution and then dried with sodium sulphate, filtered and concentrated. The crude product was purified by chromatography on silica gel (mobile phase:dichloromethane). This gave 491 mg (6% of theory) of the title compound.

1H NMR (400 MHz, CDCl₃): δ [ppm]=2.49 (ddd, 1H), 2.74 (ddd, 1H), 3.83 (s, 3H), 4.03-4.10 (m, 1H), 4.11-4.17 (m, 2H), 4.31 (d, 1H).

Example 12A

Methyl 3-(dicyanomethyl)tetrahydrofuran-3-carboxylate

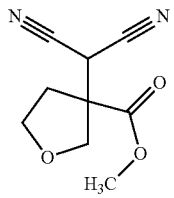

440 mg (11.00 mmol) of sodium hydride (60% in mineral oil) were initially charged in 30 ml of THF, and 726 mg (11.00 mmol) of malononitrile were added a little at a time. 2.3 g (11.00 mmol) of the compound obtained in Example 69A in THF (50 ml) were then added. The mixture was stirred at RT for 6 h and then heated at 50° C. overnight. After cooling, saturated aqueous sodium bicarbonate solution was added, and the mixture was extracted three times with ethyl acetate. The combined organic phases were washed with saturated aqueous sodium chloride solution and then dried with sodium sulphate, filtered and concentrated. The residue (2.66 g) was dried under high vacuum for 1 h and then reacted without further purification.

Example 13A

4-Amino-2-[1-(2-fluorobenzyl)-1H-pyrazolo[3,4-b]pyridin-3-yl]-5,5-dimethyl-5,7-dihydro-6H-pyrrolo[2,3-d]pyrimidin-6-one

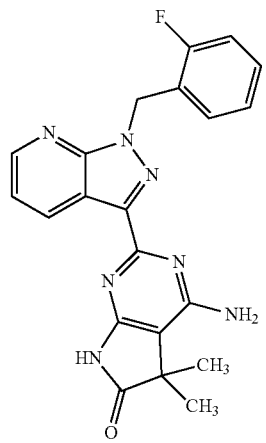 [SMILES: CC1(C)C(=O)Nc2nc(-c3nn(Cc4ccccc4F)c4ncccc34)nc(N)c21]

5.887 g (19.256 mmol) of Example 1A were initially charged in tert-butanol (50 ml), and 2.593 g (23.107 mmol) of potassium tert-butoxide were added. 3.2 g (19.256 mmol) of Example 10A in tert-butanol (25 ml) were then added dropwise, and the mixture was heated at reflux overnight. The next day, another 0.64 g (3.851 mmol) of Example 10A were added, and the mixture was heated at reflux for another day. After cooling, a precipitate was filtered off and washed with diethyl ether. The precipitate was then slurried in water, filtered off once more and washed with diethyl ether. Drying under high vacuum gave 6.65 g of the title compound (85% of theory).

LC-MS (Method 1): R$_t$=0.90 min; MS (ESIpos): m/z=404 (M+H)⁺

¹H NMR (400 MHz, DMSO-d₆): δ [ppm]=1.35 (s, 6H), 5.82 (s, 2H), 6.82 (br s, 2H), 7.14-7.25 (m, 3H), 7.33-7.40 (m, 2H), 8.63 (dd, 1H), 9.03 (dd, 1H), 10.98 (s br, 1H).

Example 14A

4-Amino-2-[5-fluoro-1-(2-fluorobenzyl)-1H-pyrazolo[3,4-b]pyridin-3-yl]-5,5-dimethyl-5,7-dihydro-6H-pyrrolo[2,3-d]pyrimidin-6-one

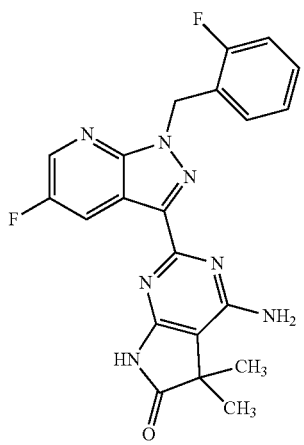 [SMILES: CC1(C)C(=O)Nc2nc(-c3nn(Cc4ccccc4F)c4ncc(F)cc34)nc(N)c21]

Analogously to the preparation of Example 2, 4.18 g (12.035 mmol) of Example 9A were reacted with 2.20 g (13.239 mmol) of Example 10A. This gave 3.72 g of the title compound (73% of theory).

LC-MS (Method 1): $R_t$=0.98 min; MS (ESIpos): m/z=422 (M+H)$^+$ $^1$H NMR (400 MHz, DMSO-d$_6$): δ [ppm]=1.34 (s, 6H), 5.81 (s, 2H), 6.85 (br s, 2H), 7.13-7.25 (m, 3H), 7.36 (m, 1H), 8.69 (dd, 1H), 8.84 (dd, 1H), 10.96 (s br, 1H).

Example 15A

4'-Amino-2'-[1-(2-fluorobenzyl)-1H-pyrazolo[3,4-b]pyridin-3-yl]-4,5-dihydrospiro[furan-3,5'-pyrrolo[2,3-d]pyrimidin]-6'(7'H)-one

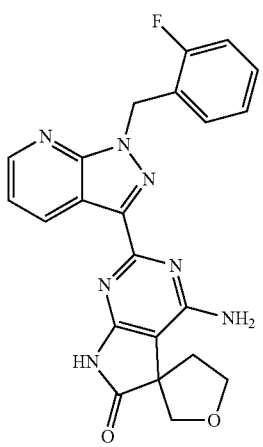 [SMILES: Nc1nc(-c2nn(Cc3ccccc3F)c3ncccc23)nc2c1C1(CCOC1)C(=O)N2]

Analogously to the preparation of Example 13A, 2.257 g (7.382 mmol) of Example 1A were reacted with 1.434 g (7.382 mmol) of Example 12A. This gave 566 mg of the title compound (17% of theory).

LC-MS (Method 1): $R_t$=0.84 min; MS (ESIpos): m/z=432 (M+H)$^+$ $^1$H NMR (400 MHz, DMSO-d$_6$): δ [ppm]=2.20-2.37 (m, 2H), 3.71 (d, 1H), 3.90 (q, 1H), 4.10 (d, 1H), 4.25-4.31 (m, 1H), 5.82 (s, 2H), 6.57 (br s, 2H), 7.12-7.25 (m, 3H), 7.33-7.41 (m, 2H), 8.64 (dd, 1H), 9.02 (dd, 1H), 11.96 (s br, 1H).

Example 16A

Ethyl {2-[1-(2-fluorobenzyl)-1H-pyrazolo[3,4-b]pyridin-3-yl]-4-hydroxypyrimidin-5-yl}acetate

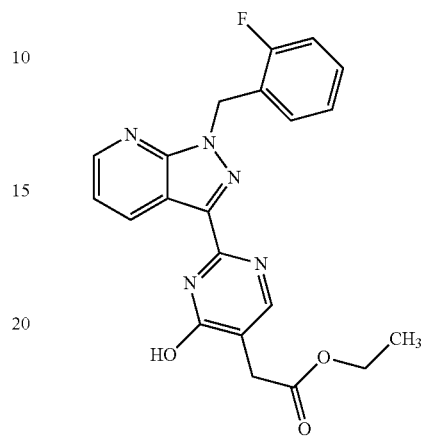

7.519 g (327 mmol) of sodium were added to ethanol (660 ml) and, under argon, reacted completely. 50.00 g (163.53 mmol) of Example 1A and, after 5 min, 40.45 g (188.01 mmol) of diethyl 2-formylbutanedioate (synthesis described in WO 2005/73234, page 43) were then added. The mixture was then heated at reflux for 12 h. After cooling, the water and then 1 N hydrochloric acid were added to the reaction mixture. The precipitate that formed was filtered off with suction and washed successively with water/ethanol (1:1, 200 ml), ethanol (100 ml) and finally with diethyl ether. Drying under high vacuum gave 58.0 g of the title compound (83% of theory).

LC-MS (Method 1): $R_t$=1.00 min; MS (ESIpos): m/z=408 (M+H)$^+$ $^1$H NMR (400 MHz, DMSO-d$_6$): δ [ppm]=1.19 (t, 3H), 3.48 (s, 2H), 4.09 (q, 2H), 5.87 (s, 2H), 7.15 (t, 1H), 7.24 (t, 1H), 7.34-7.39 (m, 2H), 7.46 (dd, 1H), 8.10 (s br, 1H), 8.71 (dd, 1H), 8.74 (d, 1H), 12.83 (s br, 1H).

Example 17A

Ethyl {4-chloro-2-[1-(2-fluorobenzyl)-1H-pyrazolo[3,4-b]pyridin-3-yl]pyrimidin-5-yl}acetate

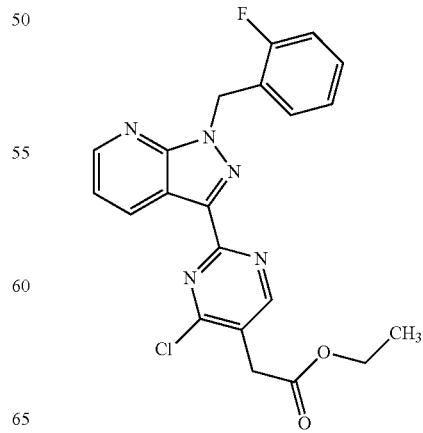

55.00 g (135 mmol) of Example 16A were initially charged in sulpholane (220 ml), and 41.40 g (270 mmol) of phosphoryl chloride were added. The mixture was then heated at 120° C. for 1 h. After cooling, the mixture was added to warm water (1500 ml) and then neutralized with solid sodium bicarbonate. The precipitate that formed was filtered off with suction and washed with water. The product was then purified further by chromatography on silica gel (mobile phase:cyclohexane/ethyl acetate 3:2). Drying under high vacuum gave 43.0 g of the title compound (73% of theory).

LC-MS (Method 1): $R_t$=1.20 min; MS (ESIpos): m/z=426 (M+H)$^+$ $^1$H NMR (400 MHz, DMSO-d$_6$): δ [ppm]=1.21 (t, 3H), 3.96 (s, 2H), 4.15 (q, 2H), 5.90 (s, 2H), 7.16 (t, 1H), 7.22-7.27 (m, 2H), 7.36-7.39 (m, 1H), 7.49 (dd, 1H), 8.71 (dd, 1H), 8.84 (dd, 1H), 8.96 (s, 1H).

Example 18A

Ethyl {4-azido-2-[1-(2-fluorobenzyl)-1H-pyrazolo[3,4-b]pyridin-3-yl]pyrimidin-5-yl}acetate

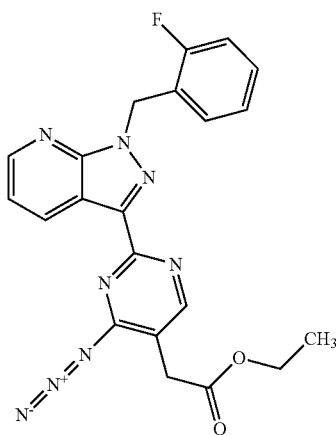 [SMILES: CCOC(=O)Cc1cnc(-c2nn(Cc3ccccc3F)c3ncccc23)nc1N=[N+]=[N-]]

10.00 g (23.482 mmol) of Example 17A were initially charged in DMF (200 ml), and 2.290 g (35.223 mmol) of sodium azide were added. The mixture was then heated at 60° C. for 1 h. After cooling, the reaction mixture was added to water and extracted three times with ethyl acetate. The organic phases were combined and washed once with saturated aqueous sodium chloride solution, then dried over sodium sulphate, filtered and concentrated. The residue was used without further purification for the next step.

LC-MS (Method 1): $R_t$=1.16 min; MS (ESIpos): m/z=433 (M+H)$^+$

Example 19A

Ethyl {4-amino-2-[1-(2-fluorobenzyl)-1H-pyrazolo[3,4-b]pyridin-3-yl]pyrimidin-5-yl}acetate

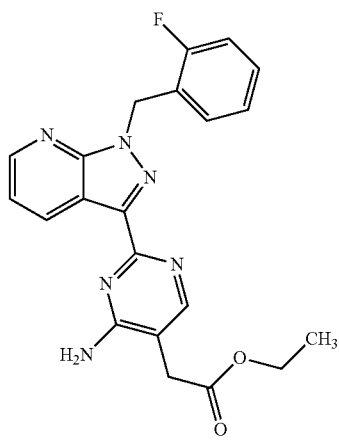 [SMILES: CCOC(=O)Cc1cnc(-c2nn(Cc3ccccc3F)c3ncccc23)nc1N]

10.15 g (23.482 mmol) of the crude product from Example 18A were hydrogenated overnight in DMF (400 ml) using palladium on carbon (10%) at a hydrogen pressure of 1 atmosphere. The mixture was then filtered through Celite and concentrated. The residue was used without further purification for the next step.

LC-MS (Method 1): $R_t$=0.83 min; MS (ESIpos): m/z=407 (M+H)$^+$

Example 20A

Ethyl 1-{4-chloro-2-[1-(2-fluorobenzyl)-1H-pyrazolo[3,4-b]pyridin-3-yl]pyrimidin-5-yl}cyclopropanecarboxylate

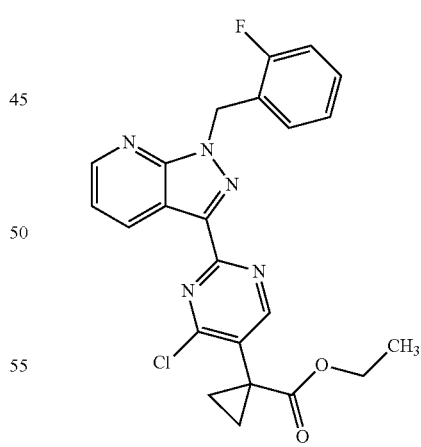

1.00 g (2.348 mmol) of Example 17A were initially charged in THF (15 ml) and DMF (15 ml), 469 mg (11.741 mmol) of sodium hydride (60%) were added and the mixture was stirred at RT for 15 min. 0.607 ml (7.054 mmol) of 1,2-dibromoethane was then added, and the mixture was stirred at RT for a further 30 min Water and ethyl acetate were added to the mixture, the phases were separated and the organic phase was extracted twice with ethyl acetate. The combined organic phases were washed once with saturated aqueous sodium chloride solution and dried with sodium sulphate, filtered and concentrated. The title compound obtained in this manner (1.38 g, 75% pure) was used without further purification for the next step.

LC-MS (Method 1): $R_t$=1.26 min; MS (ESIpos): m/z=452 (M+H)$^+$

Example 21A

Ethyl 1-{4-azido-2-[1-(2-fluorobenzyl)-1H-pyrazolo[3,4-b]pyridin-3-yl]pyrimidin-5-yl}cyclopropanecarboxylate

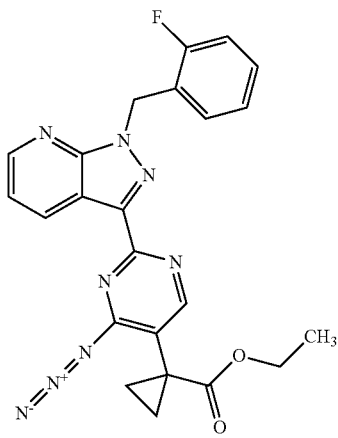 [SMILES: CCOC(=O)C1(c2cnc(-c3nn(Cc4ccccc4F)c4ncccc34)nc2N=[N+]=[N-])CC1]

550 mg (about 0.913 mmol) of Example 20A were reacted analogously to the procedure of Example 18A. The title compound obtained in this manner was used without further purification for the next step.

LC-MS (Method 1): $R_t$=1.23 min; MS (ESIpos): m/z=458 (M+H)$^+$

Example 22A

Ethyl 1-{4-amino-2-[1-(2-fluorobenzyl)-1H-pyrazolo[3,4-b]pyridin-3-yl]pyrimidin-5-yl}cyclopropanecarboxylate

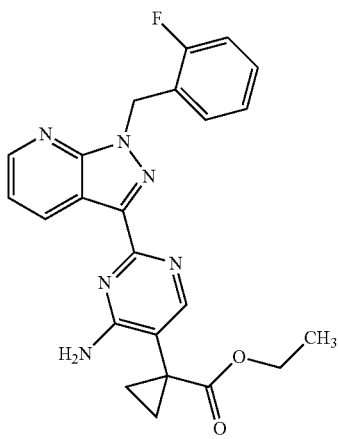 [SMILES: CCOC(=O)C1(c2cnc(-c3nn(Cc4ccccc4F)c4ncccc34)nc2N)CC1]

418 mg (0.913 mmol) of Example 21A were hydrogenated analogously to the procedure of Example 19A. The title compound obtained in this manner was used without further purification for the next step.

LC-MS (Method 1): $R_t$=0.86 min; MS (ESIpos): m/z=433 (M+H)$^+$

Example 23A 1-(2-Fluorobenzyl)-1H-pyrazolo[3,4-b]pyridine-3-carboximidohydrazide

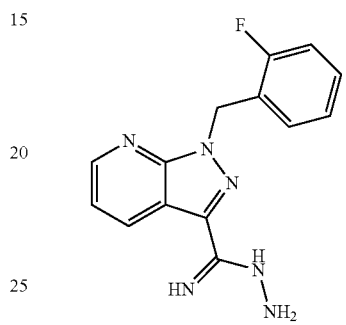

20.000 g (65.414 mmol) of the compound from Example 1A were dissolved in 320 ml of ethanol and, at 0° C., 26.477 g (261.656 mmol) of triethylamine and 4.093 g (65.414 mmol) of hydrazine hydrate (80% strength solution in water) were added. The mixture was stirred at RT overnight and then concentrated on a rotary evaporator. This gave 26.84 g (100% of theory, 69% pure) of the title compound.

LC-MS (Method 3): $R_t$=0.64 min; MS (ESIpos): m/z=285 (M+H)$^+$

Example 24A

Diethyl 2-(difluoroacetyl)butanedioate

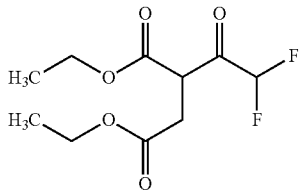 [SMILES: CCOC(=O)CC(C(=O)OCC)C(=O)C(F)F]

0.52 g (14.296 mmol) of sodium hydride (60% in mineral oil) was initially charged in THF (30 ml), and at 0° C. a solution of 2.00 g (11.437 mmol) of ethyl 4,4-difluoro-3-oxobutyrate in THF (20 ml) was then added dropwise. After warming to RT and a further 30 min at this temperature, 2.865 g (17.156 mmol) of ethyl bromoacetate in THF (15 ml) were added and the mixture was then heated at reflux overnight. After cooling, saturated aqueous ammonium chloride solution was added and the mixture was then extracted three times with ethyl acetate. The combined organic phases were dried with sodium sulphate, filtered and concentrated. After 5 min at high vacuum, the title compound obtained in this manner (3.00 g, about 50% pure) was used without further purification for the next step.

Example 25A

Ethyl {4-(difluoromethyl)-2-[1-(2-fluorobenzyl)-1H-pyrazolo[3,4-b]pyridin-3-yl]-6-hydroxypyrimidin-5-yl}acetate

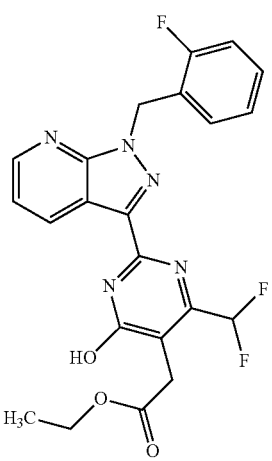

Analogously to Example 16A, 1.521 g (4.973 mmol) of Example 1A were reacted with 2.885 g (about 5.719 mmol) of Example 24A. After work-up, the product was purified by preparative HPLC (mobile phase:acetonitrile/water, gradient). This gave 600 mg (26% of theory) of the title compound.

LC-MS (Method 1): $R_t$=1.08 min; MS (ESIpos): m/z=458 (M+H)$^+$

Example 26A

Ethyl {4-chloro-6-(difluoromethyl)-2-[1-(2-fluorobenzyl)-1H-pyrazolo[3,4-b]pyridin-3-yl]-pyrimidin-5-yl}acetate

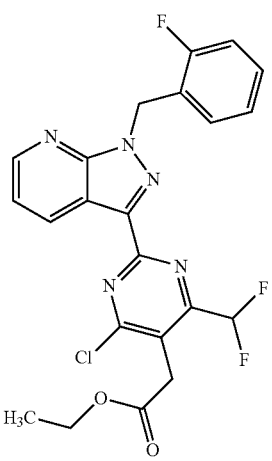 [SMILES: CCOC(=O)Cc1c(Cl)nc(-c2nn(Cc3ccccc3F)c3ncccc23)nc1C(F)F]

600 mg (1.312 mmol) of Example 25A were reacted analogously to Example 17A. This gave 1.7 g of the title compound (about 36% pure, contaminated with sulpholane).

LC-MS (Method 1): $R_t$=1.25 min; MS (ESIpos): m/z=476 (M+H)$^+$

Example 27A

Ethyl 2-{4-chloro-6-(difluoromethyl)-2-[1-(2-fluorobenzyl)-1H-pyrazolo[3,4-b]pyridin-3-yl]-pyrimidin-5-yl}-2-methylpropanoate

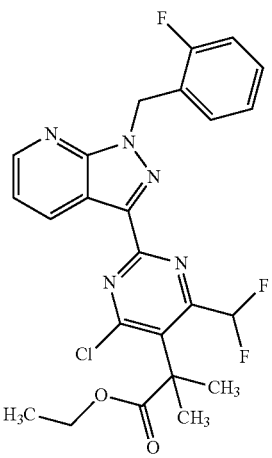 [SMILES: CCOC(=O)C(C)(C)c1c(Cl)nc(-c2nn(Cc3ccccc3F)c3ncccc23)nc1C(F)F]

Analogously to 20A, 1.7 g (about 1.31 mmol) of Example 26A were reacted with methyl iodide. This gave 1.24 g of the title compound (about 36% pure, contaminated with sulpholane).

LC-MS (Method 1): $R_t$=1.33 min; MS (ESIpos): m/z=504 (M+H)$^+$

Example 28A

Ethyl 2-{4-azido-6-(difluoromethyl)-2-[1-(2-fluorobenzyl)-1H-pyrazolo[3,4-b]pyridin-3-yl]-pyrimidin-5-yl}-2-methylpropanoate

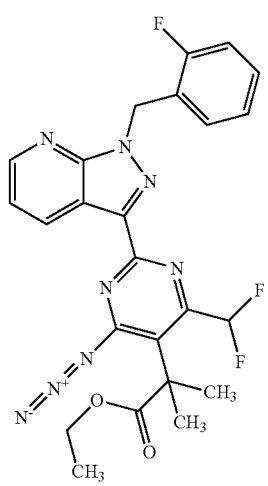 [SMILES: CCOC(=O)C(C)(C)c1c(N=[N+]=[N-])nc(-c2nn(Cc3ccccc3F)c3ncccc23)nc1C(F)F]

1.24 g (about 1.312 mmol) of Example 27A were reacted analogously to Example 18A. This gave the title compound (contaminated with sulpholane) which was reacted further without determination of the yield since the azide-containing solution was not concentrated any further.

LC-MS (Method 1): $R_t$=1.27 min; MS (ESIpos): m/z=511 (M+H)$^+$

Example 29A 1-(2,4-Difluorobenzyl)-3-iodo-1H-pyrazolo[3,4-b]pyridine

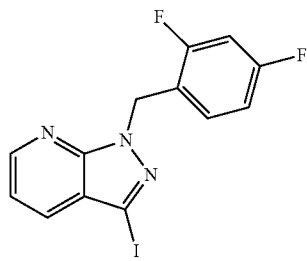 [SMILES: Fc1ccc(Cn2nc(I)c3cccnc32)c(F)c1]

Analogously to the synthesis of Example 7A, 54.00 g (215.98 mmol) of 3-iodo-1H-pyrazolo[3,4-b]pyridine (synthesis described in WO 2006/130673, Example 4) were reacted with 50.18 g (237.578) of 2,4-difluorobenzyl bromide. Ice-water was added to the crude product, the mixture was filtered off with suction and the precipitate was washed with isopropanol and pentane and then dried under high vacuum. This gave 76.7 g of the title compound (89% of theory).

LC-MS (Method 1): $R_t$=1.17 min; MS (ESIpos): m/z=372 (M+H)$^+$ $^1$H NMR (400 MHz, DMSO-d$_6$): δ=5.71 (s, 2H), 7.04-7.08 (m, 1H), 7.25-7.36 (m, 3H), 7.96 (dd, 1H), 8.65 (dd, 1H).

Example 30A 1-(2,4-Difluorobenzyl)-1H-pyrazolo[3,4-b]pyridine-3-carbonitrile

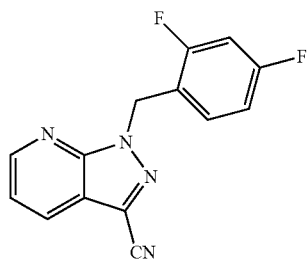 [SMILES: N#Cc1nn(Cc2ccc(F)cc2F)c2ncccc12]

76.00 g (204.78 mmol) of Example 29A were reacted analogously to Example 8A. This gave 57.00 g (94% pure, 97% of theory) of the title compound.

LC-MS (Method 1): $R_t$=1.07 min; MS (ESIpos): m/z=271 (M+H)$^+$ $^1$H NMR (400 MHz, DMSO-d$_6$): δ=5.86 (s, 2H), 7.07-7.12 (m, 1H), 7.27-7.32 (m, 1H), 7.44-7.50 (m, 1H), 7.55 (dd, 1H), 8.49 (dd, 1H), 8.81 (dd, 1H).

Example 31A 1-(2,4-Difluorobenzyl)-1H-pyrazolo[3,4-b]pyridine-3-carboximidamide acetate

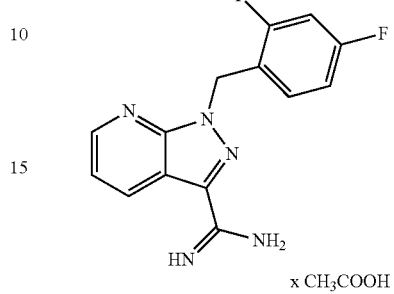

56.00 g (207.221 mmol) of Example 30A were reacted analogously to Example 9A. This gave 19.00 g of the title compound (26% of theory).

LC-MS (Method 1): $R_t$=0.60 min; MS (ESIpos): m/z=288 (M+H)$^+$ $^1$H NMR (400 MHz, DMSO-d$_6$): δ=1.81 (s, 3H), 5.80 (s, 2H), 7.03-7.08 (m, 1H), 7.26-7.37 (m, 2H), 7.41-7.44 (m, 1H), 8.61 (dd, 1H), 8.69 (dd, 1H).

Example 32A

Ethyl {2-[1-(2,4-difluorobenzyl)-1H-pyrazolo[3,4-b]pyridin-3-yl]-4-hydroxypyrimidin-5-yl}acetate

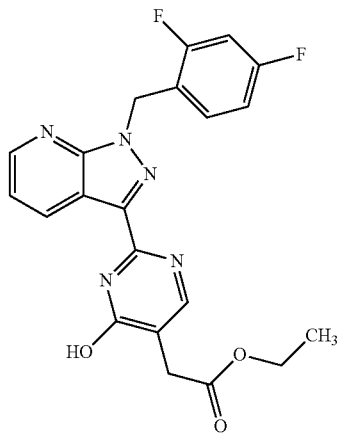 [SMILES: CCOC(=O)Cc1cnc(-c2nn(Cc3ccc(F)cc3F)c3ncccc23)nc1O]

15 g (43.187 mmol) of Example 31A were reacted analogously to the procedure of Example 16A. This gave 14.30 g of the title compound (75% of theory).

LC-MS (Method 1): $R_t$=1.03 min; MS (ESIpos): m/z=426 (M+H)$^+$ $^1$H NMR (400 MHz, DMSO-d$_6$): δ [ppm]=1.17 (t, 3H), 3.43 (s, 2H), 4.08 (q, 2H), 5.81 (s, 2H), 7.04 (ddd, 1H), 7.28 (ddd, 1H), 7.40-7.46 (m, 2H), 8.00 (s, 1H), 8.67 (dd, 1H), 8.77 (d, 1H), 12.73 (s br, 1H).

Example 33A

Ethyl {4-chloro-2-[1-(2,4-difluorobenzyl)-1H-pyrazolo[3,4-b]pyridin-3-yl]pyrimidin-5-yl}acetate

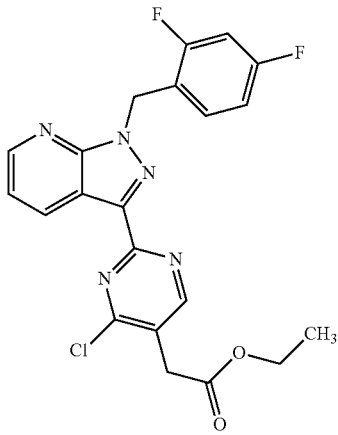 [SMILES: CCOC(=O)Cc1cnc(-c2nn(Cc3ccc(F)cc3F)c3ncccc23)nc1Cl]

14.20 g (33.380 mmol) of Example 32A were reacted analogously to the procedure of Example 17A. This gave 13.20 g of the title compound (88% of theory).

LC-MS (Method 1): $R_t$=1.23 min; MS (ESIpos): m/z=444 (M+H)$^+$ $^1$H NMR (400 MHz, DMSO-d$_6$): δ [ppm]=1.21 (t, 3H), 3.95 (s, 2H), 4.15 (q, 2H), 5.87 (s, 2H), 7.06 (ddd, 1H), 7.29 (ddd, 1H), 7.36 (ddd, 1H), 7.48 (dd, 1H), 8.71 (dd, 1H), 8.83 (dd, 1H), 8.96 (s, 1H).

Example 34A 1-(2,3-Difluorobenzyl)-3-iodo-1H-pyrazolo[3,4-b]pyridine

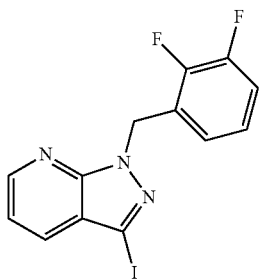 [SMILES: Fc1cccc(Cn2nc(I)c3cccnc32)c1F]

Analogously to the synthesis of Example 7A, 54.00 g (215.98 mmol) of 3-iodo-1H-pyrazolo[3,4-b]pyridine (synthesis described in WO 2006/130673 Example 4) were reacted with 50.18 g (237.578) of 2,3-difluorobenzyl bromide. Ice-water was added to the crude product, the mixture was filtered off with suction and the precipitate was washed with isopropanol and pentane and then dried under high vacuum. This gave 73.00 g of the title compound (85% of theory).

LC-MS (Method 1): $R_t$=1.13 min; MS (ESIpos): m/z=372 (M+H)$^+$ $^1$H NMR (400 MHz, DMSO-d$_6$): δ=5.79 (s, 2H), 7.04 (t, 1H), 7.14-7.20 (m, 1H), 7.33-7.43 (m, 2H), 7.98 (dd, 1H), 8.66 (dd, 1H).

Example 35A 1-(2,3-Difluorobenzyl)-1H-pyrazolo[3,4-b]pyridine-3-carbonitrile

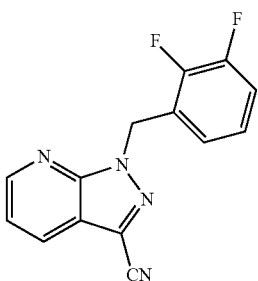 [SMILES: N#Cc1nn(Cc2cccc(F)c2F)c2ncccc12]

72.00 g (194.002 mmol) of Example 34A were reacted analogously to the synthesis of Example 8A. This gave 50.00 g (93% pure, 88% of theory) of the title compound.

LC-MS (Method 3): $R_t$=1.24 min; MS (ESIpos): m/z=271 (M+H)$^+$ $^1$H NMR (400 MHz, DMSO-d$_6$): δ=5.94 (s, 2H), 7.14-7.21 (m, 2H), 7.39-7.46 (m, 1H), 7.55 (dd, 1H), 8.51 (dd, 1H), 8.81 (dd, 1H).

Example 36A 1-(2,3-Difluorobenzyl)-1H-pyrazolo[3,4-b]pyridine-3-carboximidamide acetate

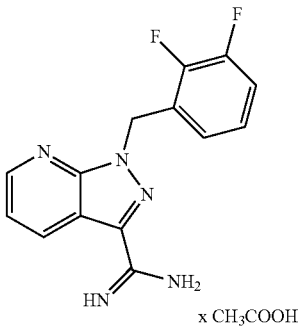 [SMILES: N=C(N)c1nn(Cc2cccc(F)c2F)c2ncccc12]

49.00 g (181.318 mmol) of Example 35A were reacted analogously to the synthesis of Example 9A. This gave 29.00 g of the title compound (46% of theory).

LC-MS (Method 1): $R_t$=0.62 min; MS (ESIpos): m/z=288 (M+H)$^+$ $^1$H NMR (400 MHz, DMSO-d$_6$): δ=1.81 (s, 3H), 5.88 (s, 2H), 7.04 (t, 1H), 7.13-7.19 (m, 1H), 7.36-7.45 (m, 2H), 8.63 (dd, 1H), 8.69 (dd, 1H).

Example 37A

Ethyl {2-[1-(2,3-difluorobenzyl)-1H-pyrazolo[3,4-b]pyridin-3-yl]-4-hydroxypyrimidin-5-yl}acetate

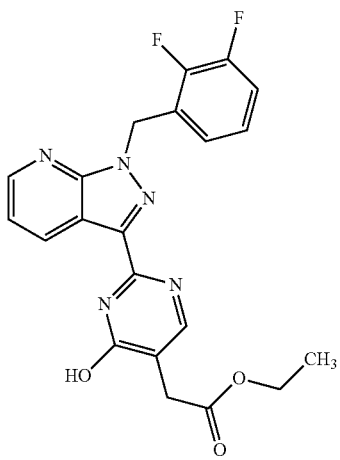 [SMILES: CCOC(=O)Cc1cnc(-c2nn(Cc3cccc(F)c3F)c3ncccc23)nc1O]

15 g (43.187 mmol) of Example 36A were reacted analogously to the procedure of Example 16A. This gave 13.20 g of the title compound (69% of theory).

LC-MS (Method 1): $R_t$=1.03 min; MS (ESIpos): m/z=426 (M+H)$^+$ $^1$H NMR (400 MHz, DMSO-d$_6$): δ [ppm]=1.19 (t, 3H), 3.48 (s, 2H), 4.09 (q, 2H), 5.90 (s, 2H), 7.13-7.18 (m, 2H), 7.36-7.43 (m, 1H), 7.47 (dd, 1H), 8.11 (s, 1H), 8.72-8.75 (m, 2H), 12.83 (s br, 1H).

Example 38A

Ethyl {4-chloro-2-[1-(2,3-difluorobenzyl)-1H-pyrazolo[3,4-b]pyridin-3-yl]pyrimidin-5-yl}acetate

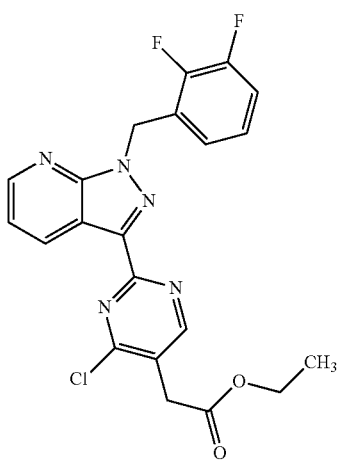 [SMILES: CCOC(=O)Cc1cnc(-c2nn(Cc3cccc(F)c3F)c3ncccc23)nc1Cl]

13.10 g (30.795 mmol) of Example 37A were reacted analogously to the procedure described in Example 17A. This gave 12.10 g of the title compound (88% of theory).

LC-MS (Method 1): $R_t$=1.23 min; MS (ESIpos): m/z=444 (M+H)$^+$ $^1$H NMR (400 MHz, DMSO-d$_6$): δ [ppm]=1.21 (t, 3H), 3.96 (s, 2H), 4.15 (q, 2H), 5.95 (s, 2H), 7.07-7.09 (t, 1H), 7.15-7.19 (m, 1H), 7.37-7.43 (m, 1H), 7.49 (dd, 1H), 8.71 (dd, 1H), 8.84 (dd, 1H), 8.96 (s, 1H).

Example 39A

Ethyl 2-{4-chloro-2-[1-(2,3-difluorobenzyl)-1H-pyrazolo[3,4-b]pyridin-3-yl]pyrimidin-5-yl}-2-methylpropanoate

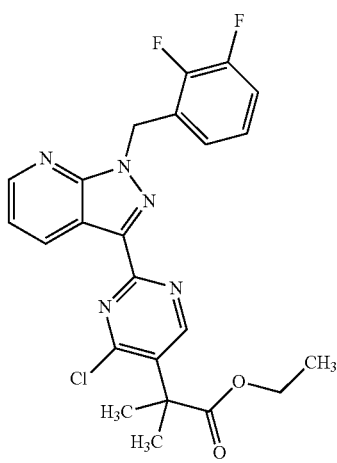 [SMILES: CCOC(=O)C(C)(C)c1cnc(-c2nn(Cc3cccc(F)c3F)c3ncccc23)nc1Cl]

Analogously to Example 20A, 800 mg (1.802 mmol) of Example 38A were reacted with methyl iodide. This gave 1.00 g (purity 84%) of the title compound which was reacted further without any further purification.

LC-MS (Method 1): $R_t$=1.30 min; MS (ESIpos): m/z=472 (M+H)$^+$ $^1$H NMR (400 MHz, DMSO-d$_6$): δ [ppm]=1.14 (t, 3H), 1.65 (s, 6H), 4.13 (q, 2H), 5.95 (s, 2H), 7.07 (t, 1H), 7.15-7.20 (m, 1H), 7.37-7.44 (m, 1H), 7.49 (dd, 1H), 8.72 (dd, 1H), 8.83 (dd, 1H), 9.06 (s, 1H).

Example 40A

Ethyl 2-{4-azido-2-[1-(2,3-difluorobenzyl)-1H-pyrazolo[3,4-b]pyridin-3-yl]pyrimidin-5-yl}-2-methylpropanoate

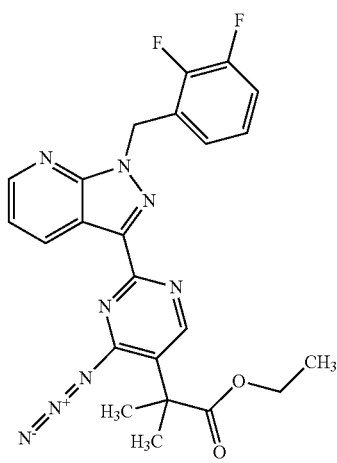 [SMILES: CCOC(=O)C(C)(C)c1cnc(-c2nn(Cc3cccc(F)c3F)c3ncccc23)nc1N=[N+]=[N-]]

67

1.00 g (about 1.80 mmol, 84% pure) of Example 39A was reacted analogously to Example 18A. The title compound obtained in this manner was reacted further without further purification. It was not possible to determine the yield, since the azide-containing solution was not concentrated to dryness.

LC-MS (Method 1): $R_t$=1.27 min; MS (ESIpos): m/z=479 (M+H)$^+$

Example 41A

Ethyl 2-{4-amino-2-[1-(2,3-difluorobenzyl)-1H-pyrazolo[3,4-b]pyridin-3-yl]pyrimidin-5-yl}-2-methylpropanoate

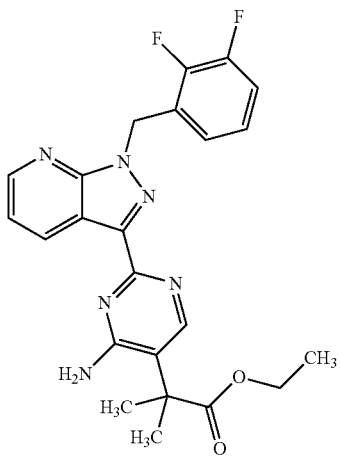 [SMILES: CCOC(=O)C(C)(C)c1cnc(-c2nn(Cc3cccc(F)c3F)c3ncccc23)nc1N]

The solution obtained in Example 40A was hydrogenated analogously to Example 19A. The crude compound obtained in this manner (0.863 g, about 94% pure) was used without purification for the next step.

LC-MS (Method 1): $R_t$=0.90 min; MS (ESIpos): m/z=453 (M+H)$^+$

Example 42A

4-Ethyl 1-methyl 2-(cyclopropylcarbonyl)butandioate

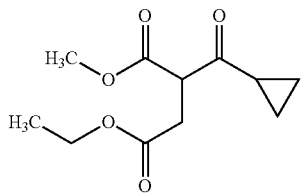 [SMILES: CCOC(=O)CC(C(=O)OC)C(=O)C1CC1]

2.00 g (14.069 mmol) of methyl 3-cyclopropyl-3-oxopropionate were reacted analogously to Example 24A. This gave 3.62 g (about 80% pure) of the title compound which was used without purification for the next step.

LC-MS (Method 1): $R_t$=0.78 min; MS (ESIpos): m/z=229 (M+H)$^+$

68

Example 43A

{4-Cyclopropyl-2-[1-(2-fluorobenzyl)-1H-pyrazolo[3,4-b]pyridin-3-yl]-6-hydroxypyrimidin-5-yl}acetic acid

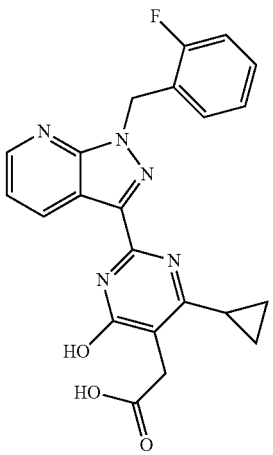 [SMILES: O=C(O)Cc1c(O)nc(-c2nn(Cc3ccccc3F)c3ncccc23)nc1C1CC1]

Analogously to Example 16A, 3.74 g (12.234 mmol) of Example 1A were reacted with 3.211 g of Example 42A. Work-up gave 763 mg (14% of theory) of the title compound.

LC-MS (Method 1): $R_t$=0.95 min; MS (ESIpos): m/z=420 (M+H)$^+$

Example 44A

Methyl {4-cyclopropyl-2-[1-(2-fluorobenzyl)-1H-pyrazolo[3,4-b]pyridin-3-yl]-6-hydroxypyrimidin-5-yl}acetate

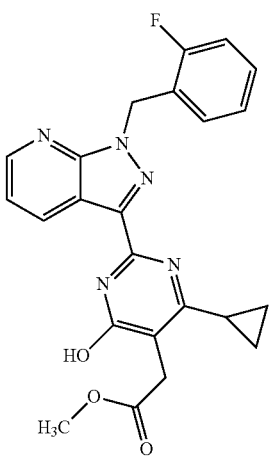 [SMILES: COC(=O)Cc1c(O)nc(-c2nn(Cc3ccccc3F)c3ncccc23)nc1C1CC1]

762 mg (1.817 mmol) of Example 43A were initially charged in methanol (20 ml), and 3 drops of conc. sulphuric acid were added. This gave a slurry which became stirrable again by further addition of methanol (15 ml). The mixture was heated at reflux for 1 h. After cooling, the mixture was filtered off with suction and washed with methanol and dried under high vacuum. This gave 685 mg (87% of theory) of the title compound.

LC-MS (Method 1): $R_t$=1.07 min; MS (ESIpos): m/z=434 (M+H)$^+$

¹H NMR (400 MHz, DMSO-d₆): δ [ppm]=1.01-1.05 (m, 2H), 1.16-1.19 (m, 2H), 2.12-2.16 (m, 1H), 3.63 (s, 3H), 3.72 (s, 2H), 5.85 (s, 2H), 7.14 (t, 1H), 7.20-7.25 (m, 1H), 7.31-7.39 (m, 2H), 7.49 (dd, 1H), 8.55 (dd, 1H), 8.70 (dd, 1H), 12.57 (s br, 1H).

Example 45A

Methyl {4-chloro-6-cyclopropyl-2-[1-(2-fluorobenzyl)-1H-pyrazolo[3,4-b]pyridin-3-yl]pyrimidin-5-yl}acetate

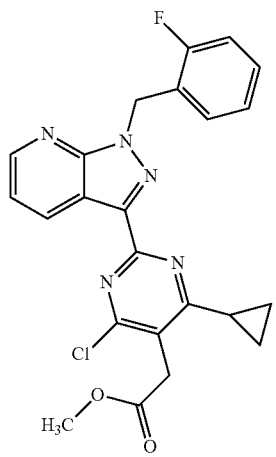 [SMILES: COC(=O)Cc1c(Cl)nc(-c2nn(Cc3ccccc3F)c3ncccc23)nc1C1CC1]

683 mg (1.576 mmol) of Example 44A were initially charged in phosphoryl chloride (2.423 ml), 470 mg (3.151 mmol) of diethylaniline were added and the mixture was heated at 90° C. for 2 days. After cooling, the mixture was added to warm water and the precipitate formed was filtered off with suction, washed with water and dried under high vacuum. This gave 724 mg (100% of theory) of the title compound.

LC-MS (Method 1): R_t=1.25 min; MS (ESIpos): m/z=452 (M+H)⁺

Example 46A

Methyl 2-{4-chloro-6-cyclopropyl-2-[1-(2-fluorobenzyl)-1H-pyrazolo[3,4-b]pyridin-3-yl]-pyrimidin-5-yl}-2-methylpropanoate

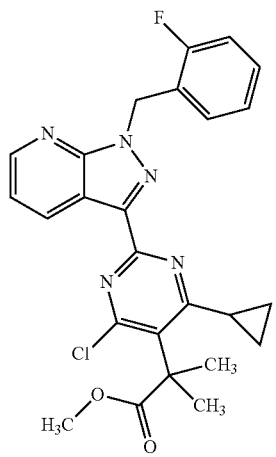 [SMILES: COC(=O)C(C)(C)c1c(Cl)nc(-c2nn(Cc3ccccc3F)c3ncccc23)nc1C1CC1]

Analogously to Example 20A, 712 mg (1.576 mmol) of Example 45A were reacted with methyl iodide. This gave 867 mg (about 75% pure) of the title compound which were used without purification for the next step.

LC-MS (Method 1): R_t=1.39 min; MS (ESIpos): m/z=480 (M+H)⁺

Example 47A

Methyl 2-{4-azido-6-cyclopropyl-2-[1-(2-fluorobenzyl)-1H-pyrazolo[3,4-b]pyridin-3-yl]pyrimidin-5-yl}-2-methylpropanoate

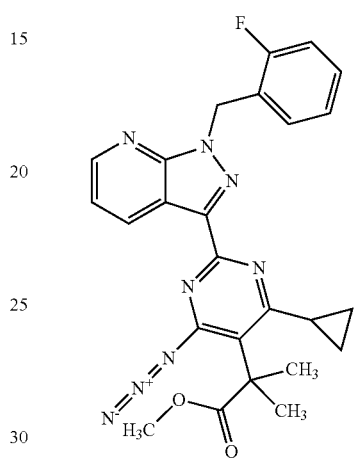

867 mg (about 1.355 mmol) of Example 46A were reacted analogously to the procedure of Example 18A. The title compound obtained in this manner was used without further purification for the next step. The yield was not determined, since the azide-containing solution was not concentrated to dryness.

LC-MS (Method 1): R_t=1.31 min; MS (ESIpos): m/z=487 (M+H)⁺

Example 48A

Ethyl 2-{4-chloro-2-[1-(2,4-difluorobenzyl)-1H-pyrazolo[3,4-b]pyridin-3-yl]pyrimidin-5-yl}-2-methylpropanoate

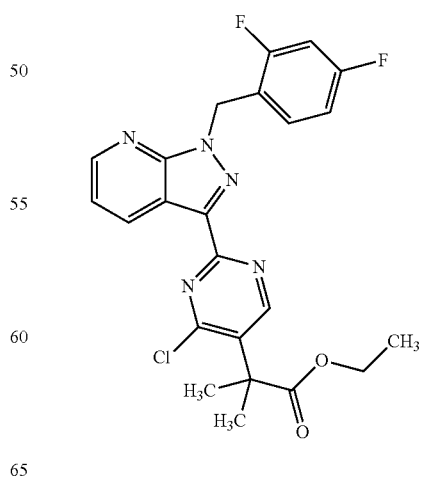

Analogously to Example 20A, 800 mg (1.802 mmol) of Example 33A were reacted with methyl iodide. This gave 1.05 g (78% pure) of the title compound which were used without purification for the next step.

LC-MS (Method 1): $R_t$=1.31 min; MS (ESIpos): m/z=472 (M+H)$^+$

Example 49A

Ethyl 2-{4-azido-2-[1-(2,4-difluorobenzyl)-1H-pyrazolo[3,4-b]pyridin-3-yl]pyrimidin-5-yl}-2-methylpropanoate

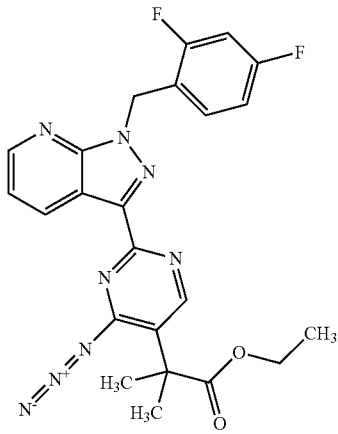 [SMILES: CCOC(=O)C(C)(C)c1cnc(-c2nn(Cc3ccc(F)cc3F)c3ncccc23)nc1N=[N+]=[N-]]

1.05 g (about 1.736 mmol) of Example 48A were reacted analogously to the procedure of Example 18A. The title compound obtained in this manner was used without further purification for the next step. The yield was not determined, since the azide-containing solution was not concentrated to dryness.

LC-MS (Method 1): $R_t$=1.27 min; MS (ESIpos): m/z=479 (M+H)$^+$

Example 50A

Ethyl 2-{4-amino-2-[1-(2,4-difluorobenzyl)-1H-pyrazolo[3,4-b]pyridin-3-yl]pyrimidin-5-yl}-2-methylpropanoate

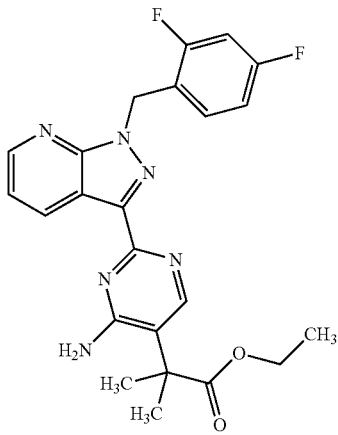 [SMILES: CCOC(=O)C(C)(C)c1cnc(-c2nn(Cc3ccc(F)cc3F)c3ncccc23)nc1N]

The solution obtained in Example 49A was hydrogenated analogously to the procedure of Example 19A. The title compound obtained in this manner (0.755 g, about 76% pure) was used without further purification for the next step. LC-MS (Method 1): $R_t$=0.91 min; MS (ESIpos): m/z=453 (M+H)$^+$ Example 51A 2-Methoxy-4-methyl-6-oxo-1,4,5,6-tetrahydropyridine-3-carbonitrile

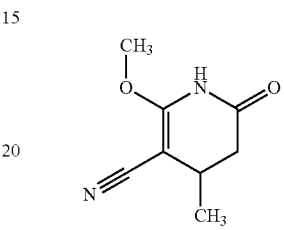

The synthesis of the compound has been described: *Heterocycles*, 1985; 1135-1141.

Example 52A

2-Methoxy-6-oxo-4-(trifluoromethyl)-1,4,5,6-tetrahydropyridine-3-carbonitrile

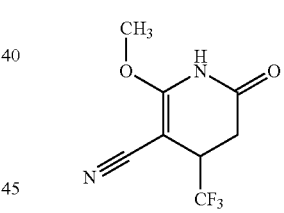

With ice cooling, 7.47 g (138.39 mmol) of sodium methoxide in methanol (85 ml) were initially charged, and 6.04 g (91.44 mmol) of malononitrile were added. With stirring, 11.84 g (76.84 mmol) of methyl 4,4,4-trifluorocrotonate were then added dropwise, and the mixture was stirred at RT for 30 min and then heated at reflux for 1 h. Under reduced pressure, the mixture was then concentrated to dryness. Water was added to the residue, and the mixture was extracted four times with ethyl acetate. The combined organic phases were dried with sodium sulphate, filtered and concentrated. Further purification was carried out by chromatography on silica gel (cyclohexane/ethyl acetate 3:1). This gave 1.95 g of the title compound (11% of theory).

LC-MS (Method 1): $R_t$=0.61 min; MS (ESIpos): m/z=221 (M+H)$^+$

Example 53A

4-Amino-2-[1-(2-fluorobenzyl)-1H-pyrazolo[3,4-b]pyridin-3-yl]-5-methyl-5,8-dihydropyrido[2,3-d]pyrimidin-7(6H)-one

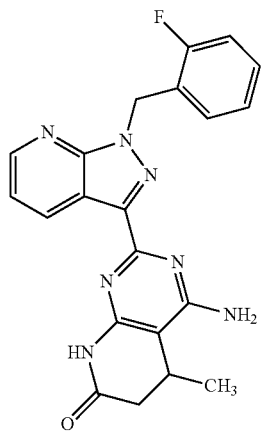 [SMILES: CC1CC(=O)Nc2nc(-c3nn(Cc4ccccc4F)c4ncccc34)nc(N)c21]

2.174 g (7.112 mmol) of Example 1A and 1.3 g (7.823 mmol) of Example 51A were initially charged in 20 ml of methanol, and 422 mg (7.823 mmol) of sodium methoxide were then added a little at a time at RT. The mixture was stirred at RT for 10 min and then heated at reflux overnight. After cooling, acetic acid (0.5 ml) and water (20 ml) were added and the mixture was cooled in an ice bath. The precipitate was filtered off with suction, washed with water and methanol and then dried under high vacuum. This gave 2.51 g of the title compound (87% of theory).

LC-MS (Method 1): $R_t$=0.85 min; MS (ESIpos): m/z=404 (M+H)$^+$ $^1$H NMR (400 MHz, DMSO-d$_6$): δ [ppm]=1.04 (d, 3H), 2.31 (d, 1H), 2.79 (dd, 1H), 3.13-3.19 (m, 1H), 5.81 (s, 2H), 6.93 (br s, 2H), 7.12-7.25 (m, 3H), 7.34-7.37 (m, 2H), 8.62 (dd, 1H), 9.14 (dd, 1H), 10.56 (s, 1H).

Example 54A

4-Amino-2-[1-(2-fluorobenzyl)-1H-pyrazolo[3,4-b]pyridin-3-yl]-5-(trifluoromethyl)-5,8-dihydropyrido[2,3-d]pyrimidin-7(6H)-one

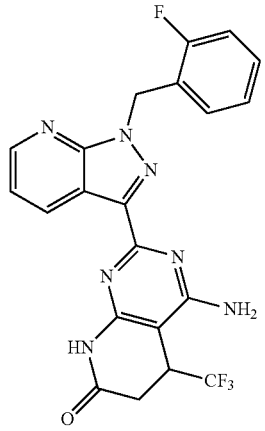 [SMILES: Nc1nc(-c2nn(Cc3ccccc3F)c3ncccc23)nc2c1C(C(F)(F)F)CC(=O)N2]

694 mg (2.271 mmol) of Example 1A and 500 mg (2.271 mmol) of Example 14A were initially charged in 10 ml of tert-butanol, and 305 mg (2.725 mmol) of potassium tert-butoxide were then added a little at a time at RT. The mixture was stirred at RT for 10 min and then heated at reflux for 2 days. After cooling, water and ethyl acetate were added to the reaction mixture. The precipitate was filtered off with suction. The filtrate was concentrated, a little ethyl acetate and diethyl ether were added and the precipitate formed was filtered off with suction. The combined solids fractions were then dried under high vacuum. This gave 588 mg of the title compound (53% of theory).

LC-MS (Method 1): $R_t$=0.92 min; MS (ESIpos): m/z=458 (M+H)$^+$

1H NMR (400 MHz, DMSO-d6): δ [ppm]=2.63 (d, 1H), 3.19 (dd, 1H), 4.16-4.20 (m, 1H), 5.83 (s, 2H), 7.13-7.40 (m, 7H), 8.63 (dd, 1H), 9.15 (dd, 1H), 10.85 (s, 1H).

Example 55A

2-[1-(2-Fluorobenzyl)-1H-pyrazolo[3,4-b]pyridin-3-yl]-4-iodo-5,5-dimethyl-5,7-dihydro-6H-pyrrolo[2,3-d]pyrimidin-6-one

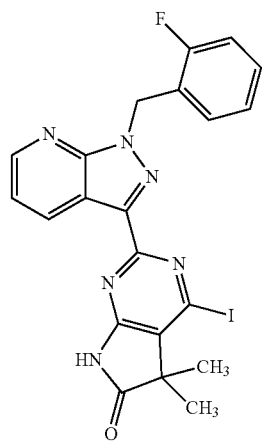 [SMILES: CC1(C)C(=O)Nc2nc(-c3nn(Cc4ccccc4F)c4ncccc34)nc(I)c21]

5.00 g (12.394 mmol) of Example 13A were initially charged in isopentyl nitrite (35.87 ml) and diiodomethane (1.16 mol, 93.71 ml), and the mixture was heated at 85° C. for 12 h. After cooling, the solids were filtered off and the filtrate was concentrated and then purified by chromatography on silica gel (mobile phase:first cyclohexane/dichloromethane gradient, then dichloro-methane/methanol gradient). This gave 5.50 g of the title compound (67% of theory).

LC-MS (Method 1): $R_t$=1.19 min; MS (ESIpos): m/z=515 (M+H)$^+$ $^1$H NMR (400 MHz, DMSO-d$_6$): δ [ppm]=1.42 (s, 6H), 5.88 (s, 2H), 7.13-7.26 (m, 3H), 7.34-7.38 (m, 1H), 7.48 (dd, 1H), 8.69 (dd, 1H), 8.79 (dd, 1H), 11.78 (s br, 1H).

Example 56A

2-[5-Fluoro-1-(2-fluorobenzyl)-1H-pyrazolo[3,4-b]pyridin-3-yl]-4-iodo-5,5-dimethyl-5,7-dihydro-6H-pyrrolo[2,3-d]pyrimidin-6-one

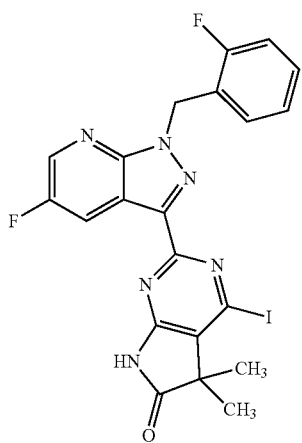 [SMILES: CC1(C)C(=O)Nc2nc(-c3nn(Cc4ccccc4F)c4ncc(F)cc34)nc(I)c21]

3.325 g (7.890 mmol) of Example 14A were reacted analogously to Example 55A. This gave 3.65 g of the title compound (87% of theory, 61% pure).

LC-MS (Method 1): R_t=1.26 min; MS (ESIpos): m/z=533 (M+H)+

$^1$H NMR (400 MHz, DMSO-d$_6$): δ [ppm]=1.42 (s, 6H), 5.87 (s, 2H), 7.14-7.26 (m, 3H), 7.37 (m, 1H), 8.48 (dd, 1H), 8.77 (dd, 1H), 11.76 (s br, 1H).

Example 57A

2'-[1-(2-Fluorobenzyl)-1H-pyrazolo[3,4-b]pyridin-3-yl]-4'-iodo-4,5-dihydrospiro[furan-3,5'-pyrrolo[2,3-d]pyrimidin]-6'(7'H)-one

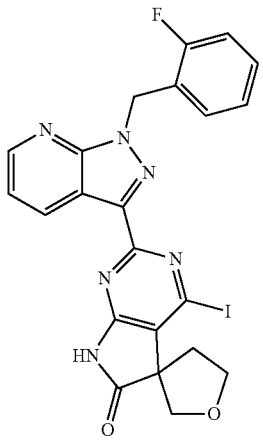 [SMILES: O=C1Nc2nc(-c3nn(Cc4ccccc4F)c4ncccc34)nc(I)c2C12CCOC2]

563 mg (1.305 mmol) of the compound obtained in Example 15A were initially charged in 1,2-dimethoxyethane (7.5 ml), and 339 mg (1.305 mmol) of caesium iodide, 165 mg (0.652 mmol) of iodine and 74 mg (0.391 mmol) of copper(I) iodide were then added. Isopentyl nitrite (1.04 ml) was then added, and the mixture was heated at 60° C. for 2 days. After cooling, the mixture was filtered, the filter cake was washed with ethyl acetate and the filtrate was washed twice with 5% strength aqueous sodium thiosulphate solution and once with saturated aqueous sodium chloride solution. The organic phase was then dried over sodium sulphate, filtered and concentrated to dryness. The residue was purified by preparative HPLC (acetonitrile/water (+0.05% formic acid) gradient). This gave 98 mg of the title compound (14% of theory).

LC-MS (Method 1): R_t=1.07 min; MS (ESIpos): m/z=543 (M+H)+

$^1$H NMR (400 MHz, DMSO-d$_6$): δ [ppm]=2.23-2.29 (m, 1H), 2.50 (1H, partially under DMSO peak), 3.93 (d, 1H), 4.04 (q, 1H), 4.16 (d, 1H), 4.21-4.27 (m, 1H), 5.88 (s, 2H), 7.13-7.26 (m, 3H), 7.34-7.40 (m, 1H), 7.49 (dd, 1H), 8.69 (dd, 1H), 8.80 (dd, 1H), 11.80 (s br, 1H).

Example 58A

2-[1-(2-Fluorobenzyl)-1H-pyrazolo[3,4-b]pyridin-3-yl]-4-iod-5-methyl-5,8-dihydropyrido[2,3-d]pyrimidin-7(6H)-one

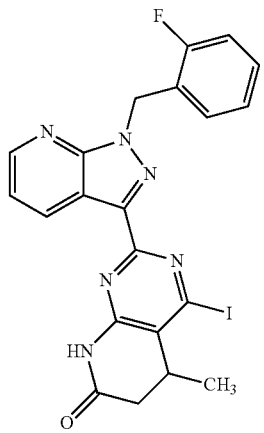 [SMILES: CC1CC(=O)Nc2nc(-c3nn(Cc4ccccc4F)c4ncccc34)nc(I)c21]

530 mg (1.314 mmol) of Example 53A were reacted analogously to the procedure of Example 57A. This gave 171 mg of the title compound (25% of theory).

LC-MS (Method 1): R_t=1.13 min; MS (ESIpos): m/z=515 (M+H)+

$^1$H NMR (400 MHz, DMSO-d$_6$): δ [ppm]=1.12 (d, 3H), 2.46 (signal partially under solvent, 1H), 3.01 (dd, 1H), 3.16-3.19 (m, 1H), 5.88 (s, 2H), 7.13-7.14 (m, 2H), 7.24 (t, 1H), 7.34-7.38 (m, 1H), 7.45 (dd, 1H), 8.67 (dd, 1H), 9.09 (dd, 1H), 11.33 (s, 1H).

Example 59A

2-[1-(2-Fluorobenzyl)-1H-pyrazolo[3,4-b]pyridin-3-yl]-4-iodo-5-(trifluoromethyl)-5,8-dihydropyrido[2,3-d]pyrimidin-7(6H)-one

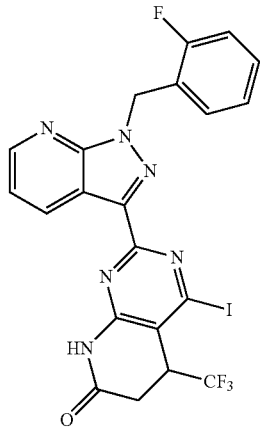 [SMILES: O=C1CC(C(F)(F)F)c2c(I)nc(-c3nn(Cc4ccccc4F)c4ncccc34)nc2N1]

556 mg (1.216 mmol) of Example 54A were reacted analogously to Example 57A. This gave 605 mg of the title compound (87% of theory).

LC-MS (Method 1): R$_t$=1.15 min; MS (ESIpos): m/z=569 (M+H)$^+$ $^1$H NMR (400 MHz, DMSO-d$_6$): δ [ppm]=2.74 (d, 1H), 3.38 (dd, 1H), 4.17-4.24 (m, 1H), 5.90 (s, 2H), 7.14-7.17 (m, 2H), 7.24 (t, 1H), 7.33-7.40 (m, 1H), 7.48 (dd, 1H), 8.69 (dd, 1H), 9.01 (dd, 1H), 11.60 (s, 1H).

Example 60A

5-Fluoro-1-(2-fluorobenzyl)-1H-pyrazolo[3,4-b]pyridine-3-carboximidohydrazide

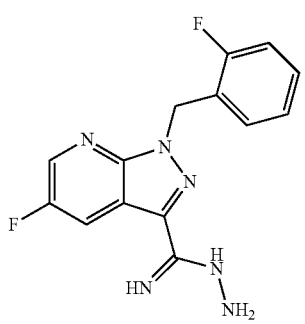 [SMILES: N=C(NN)c1nn(Cc2ccccc2F)c2ncc(F)cc12]

23.000 g (66.22 mmol) of Example 9A were dissolved in 322 ml of ethanol, and 26.804 g (264.88 mmol) of triethylamine and 6.027 g (66.22 mmol) of hydrazine hydrate (55% strength solution in water) were added at 0° C. The mixture was stirred at RT overnight and then added to 1.715 l of a 10% strength aqueous sodium chloride solution and extracted twice with ethyl acetate. The combined organic phases were washed with 10% strength aqueous sodium chloride solution, dried over sodium sulphate and concentrated on a rotary evaporator. The residue was purified on silica gel (mobile phase:dichloromethane/methanol, 95:5). This gave 15.000 g (75% of theory) of the title compound.

LC-MS (Method 1): R$_t$=0.58 min; MS (ESIpos): m/z=303 (M+H)$^+$ $^1$H NMR (400 MHz, DMSO-d$_6$): δ [ppm]=5.38 (s, 2H), 5.54 (s, 2H), 5.72 (s, 2H), 7.10-7.15 (m, 2H), 7.20-7.25 (m, 1H), 7.32-7.38 (m, 1H), 8.21 (dd, 1H), 8.64 (dd, 1H).

Example 61A

Methyl 2-{3-[5-fluoro-1-(2-fluorobenzyl)-1H-pyrazolo[3,4-b]pyridin-3-yl]-5-hydroxy-1,2,4-triazin-6-yl}-2-methylpropanoate

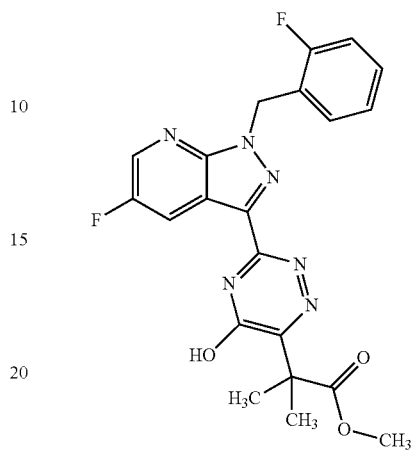

11.780 g (38.97 mmol) of Example 60A were dissolved in 353 ml of ethanol, and 14.667 g (77.94 mmol) of dimethyl 2,2-dimethyl-3-oxobutanedioate (described in J. Am. Chem. Soc. 124(14), 3680-3691; 2002) were added. The mixture was heated at reflux overnight. After cooling, the solid was filtered off with suction and washed with a little ethanol and the filtrate was concentrated. The residue was purified on silica gel (mobile phase:dichloromethane/acetone, 95:5). This gave 10.000 g (58% of theory) of the title compound.

LC-MS (Method 1): R$_t$=1.07 min; MS (ESIpos): m/z=441 (M+H)$^+$ $^1$H NMR (400 MHz, DMSO-d$_6$): δ [ppm]=1.45 (s, 6H), 3.56 (s, 3H), 5.91 (s, 2H), 7.16 (dt, 1H), 7.22-7.31 (m, 2H), 7.36-7.41 (m, 1H), 8.41 (dd, 1H), 8.83 (dd, 1H), 14.58 (s, 1H).

Example 62A 1-(2,3-Difluorobenzyl)-5-fluoro-3-iodo-1H-pyrazolo[3,4-b]pyridine

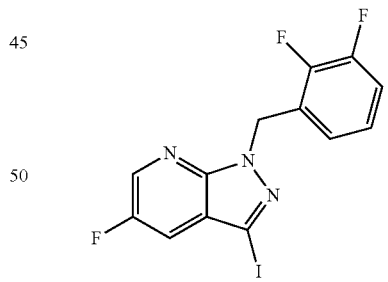

10.000 g (38.02 mmol) of Example 6A were dissolved in 270 ml of dimethylformamide, and 8.658 g (41.82 mmol) of 1-(bromomethyl)-2,3-difluorobenzene and 13.627 g (41.82 mmol) of caesium carbonate were added. The mixture was stirred at room temperature for 2 h, and ethyl acetate and water were then added. The organic phase was separated off and the aqueous phase was extracted three times with ethyl acetate. The combined organic phases were dried over sodium sulphate and concentrated on a rotary evaporator. This gave 8.460 g (56% of theory) of the target compound. The residue was used without further purification for the next step.

LC-MS (Method 1): R$_t$=1.24 min; MS (ESIpos): m/z=390 (M+H)$^+$ $^1$H NMR (400 MHz, DMSO-d$_6$): δ [ppm]=5.78 (s, 2H), 7.03-7.08 (m, 1H), 7.15-7.20 (m, 1H), 7.36-7.44 (m, 1H), 7.95 (dd, 1H), 8.72 (t, 1H).

Example 63A 1-(2,3-Difluorobenzyl)-5-fluoro-1H-pyrazolo[3,4-b]pyridine-3-carbonitrile

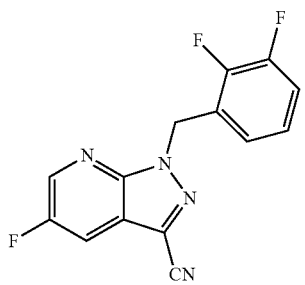 [SMILES: N#Cc1nn(Cc2cccc(F)c2F)c2ncc(F)cc12]

8.470 g (21.25 mmol) of Example 62A were dissolved in 59 ml of dimethyl sulphoxide, and 2.093 g (23.37 mmol) of copper(I) cyanide were added. The mixture was stirred at 150° C. for 1.5 h and then diluted with methanol and filtered through Celite. The filter cake was washed with methanol and the filtrate was concentrated on a rotary evaporator. The residue was taken up in ethyl acetate and washed twice with a mixture of saturated aqueous ammonium chloride solution and 25% strength aqueous ammonia solution (v/v=3:1) and also with saturated aqueous sodium chloride solution. The organic phase was separated off, dried over sodium sulphate and concentrated on a rotary evaporator. This gave 5.750 g (89% of theory, purity about 94%) of the target compound. The residue was used without further purification for the next step.

LC-MS (Method 1): R$_t$=1.32 min; MS (ESIpos): m/z=289 (M+H)$^+$ $^1$H NMR (400 MHz, DMSO-d$_6$): δ [ppm]=5.93 (s, 2H), 7.13-7.24 (m, 2H), 7.40-7.47 (m, 1H), 8.53 (dd, 1H), 8.88 (dd, 1H).

Example 64A 1-(2,3-Difluorobenzyl)-5-fluoro-1H-pyrazolo[3,4-b]pyridine-3-carboximidamide acetate

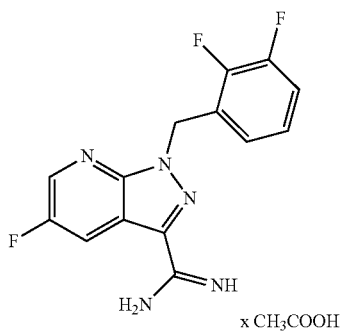 [SMILES: N=C(N)c1nn(Cc2cccc(F)c2F)c2ncc(F)cc12]

A little at a time, 0.433 g (18.81 mmol) of sodium were stirred into 133 ml of methanol. After the evolution of gas had ceased, 5.750 g (18.81 mmol) of Example 63A were added gradually, and the mixture was stirred at room temperature for 2 h. 1.208 g (22.57 mmol) of ammonium chloride and 4.394 g (73.17 mmol) of acetic acid were added, and the mixture was boiled under reflux overnight. After cooling, the mixture was concentrated on a rotary evaporator and ethyl acetate and 1 N aqueous sodium hydroxide solution were added to the residue, resulting in the formation of a solid. The solid was filtered off with suction, washed with ethyl acetate and dried under high vacuum. This gave 5.860 g (83% of theory) of the target compound.

LC-MS (Method 1): R$_t$=0.60 min; MS (ESIpos): m/z=306 (M-C$_2$H$_3$O$_2$)$^+$ $^1$H NMR (400 MHz, DMSO-d$_6$): δ=1.83 (s, 3H), 5.85 (s, 2H), 7.04 (t, 1H), 7.13-7.19 (m, 1H), 7.36-7.43 (m, 1H), 8.44 (dd, 1H), 8.45 (s br, 2H), 8.74 (s, 1H).

Example 65A 1-(2,3-Difluorobenzyl)-5-fluoro-1H-pyrazolo[3,4-b]pyridine-3-carboximidohydrazide

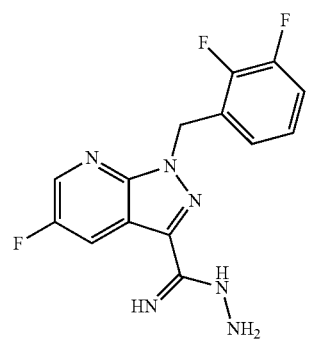 [SMILES: N=C(NN)c1nn(Cc2cccc(F)c2F)c2ncc(F)cc12]

5.680 g (15.55 mmol) of the compound from Example 64A were dissolved in 76 ml of ethanol, and 6.293 g (62.19 mmol) of triethylamine and 0.973 g (15.55 mmol) of hydrazine hydrate (80% strength solution in water) were added at 0° C. The mixture was stirred at RT overnight and then concentrated on a rotary evaporator. This gave 5.850 g (99% of theory, purity 84%) of the title compound. The product was used without further purification for the next step.

LC-MS (Method 1): R$_t$=0.68 min; MS (ESIpos): m/z=321 (M+H)$^+$

Example 66A

Methyl 2-{4-[1-(2,3-difluorobenzyl)-5-fluoro-1H-pyrazolo[3,4-b]pyridin-3-yl]-2-hydroxyphenyl}-2-methylpropanoate

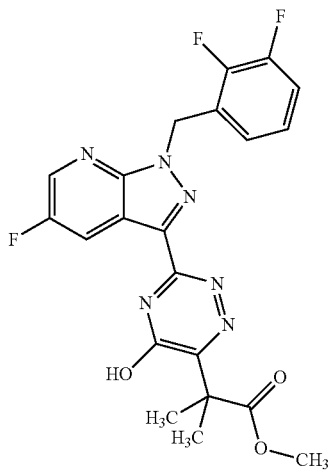 [SMILES: COC(=O)C(C)(C)c1nnc(-c2nn(Cc3cccc(F)c3F)c3ncc(F)cc23)nc1O]

5.850 g (15.40 mmol) of the compound from Example 65A were dissolved in 140 ml of ethanol, 5.795 g (30.80 mmol) of dimethyl 2,2-dimethyl-3-oxobutanedioate (described in J. Am. Chem. Soc. 124(14), 3680-3691; 2002) were added and the mixture was stirred overnight. The solid formed was filtered off with suction and washed with a little ethanol, and the filtrate was concentrated. The residue was stirred with diethyl ether, filtered off with suction, washed with a little diethyl ether and dried under high vacuum. This gave 2.060 g (29% of theory) of the title compound.

LC-MS (Method 1): $R_t$=1.03 min; MS (ESIpos): m/z=459 (M+H)$^+$ $^1$H NMR (400 MHz, DMSO-d$_6$): δ [ppm]=1.45 (s, 6H), 3.56 (s, 3H), 5.94 (s, 2H), 7.10-7.21 (m, 2H), 7.42 (q, 1H), 8.42 (dd, 1H), 8.83 (s, 1H), 14.53 (s br, 1H).

Example 67A 1-(2,4-Difluorobenzyl)-5-fluoro-3-iodo-1H-pyrazolo[3,4-b]pyridine

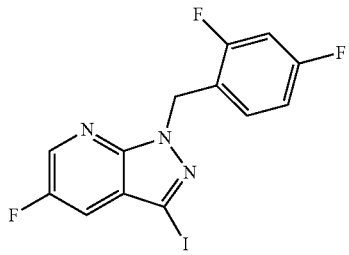 [SMILES: Fc1ccc(Cn2nc(I)c3cc(F)cnc32)c(F)c1]

10.000 g (38.02 mmol) of Example 6A were dissolved in 270 ml of dimethylformamide, and 8.658 g (41.82 mmol) of 1-(bromomethyl)-2,4-difluorobenzene and 13.627 g (41.82 mmol) of caesium carbonate were added. The mixture was stirred at room temperature for 2 h, and ethyl acetate and water were then added. The organic phase was separated off and the aqueous phase was extracted three times with ethyl acetate. The combined organic phases were dried over sodium sulphate and concentrated on a rotary evaporator. This gave 8.340 g (53% of theory, purity about 93%) of the target compound. The residue was used without further purification for the next step.

LC-MS (Method 3): $R_t$=1.45 min; MS (ESIpos): m/z=390 (M+H)$^+$ $^1$H NMR (400 MHz, DMSO-d$_6$): δ [ppm]=5.71 (s, 2H), 7.07 (dt, 1H), 7.27 (dt, 1H), 7.33-7.39 (m, 1H), 7.94 (dd, 1H), 8.72 (t, 1H).

Example 68A 1-(2,4-Difluorobenzyl)-5-fluoro-1H-pyrazolo[3,4-b]pyridine-3-carbonitrile

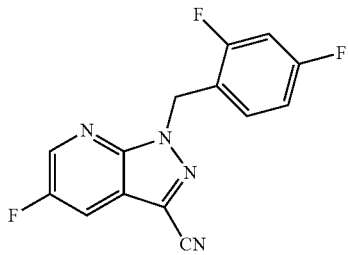 [SMILES: N#Cc1nn(Cc2ccc(F)cc2F)c2ncc(F)cc12]

8.340 g (20.07 mmol) of Example 67A were dissolved in 56 ml of dimethyl sulphoxide, and 1.977 g (22.07 mmol) of copper(I) cyanide were added. The mixture was stirred at 150° C. for 1.5 h and then diluted with methanol and filtered through Celite. The filter cake was washed with methanol and the filtrate was concentrated on a rotary evaporator. The residue was taken up in ethyl acetate and washed twice with a mixture of saturated aqueous ammonium chloride solution and 25% strength aqueous ammonia solution (v/v=3:1) and with saturated aqueous sodium chloride solution. The organic phase was separated off, dried over sodium sulphate and concentrated on a rotary evaporator. This gave 5.270 g (83% of theory, purity about 91%) of the target compound. The residue was used without further purification for the next step.

LC-MS (Method 1): $R_t$=1.09 min; MS (ESIpos): m/z=289 (M+H)$^+$ $^1$H NMR (400 MHz, DMSO-d$_6$): δ [ppm]=5.85 (s, 2H), 7.10 (dt, 1H), 7.30 (dt, 1H), 7.45-7.51 (m, 1H), 8.52 (dd, 1H), 8.88 (t, 1H).

Example 69A 1-(2,4-Difluorobenzyl)-5-fluoro-1H-pyrazolo[3,4-b]pyridine-3-carboximidamide acetate

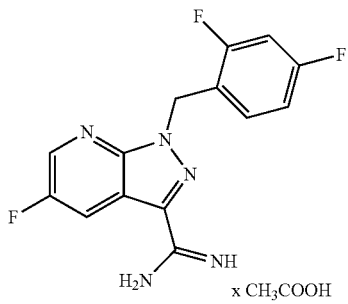 [SMILES: N=C(N)c1nn(Cc2ccc(F)cc2F)c2ncc(F)cc12]

A little at a time, 0.383 g (16.68 mmol) of sodium were stirred into 118 ml of methanol. After the formation of gas had ceased, 5.270 g (about 16.68 mmol) of Example 68A were added in portions, and the mixture was stirred at room temperature for 2 h. 1.070 g (20.01 mmol) of ammonium chloride and 3.895 g (64.86 mmol) of acetic acid were added, and the mixture was boiled under reflux overnight. After cooling, the mixture was concentrated on a rotary evaporator and ethyl acetate and 1 N aqueous sodium hydroxide solution were added to the residue, resulting in the formation of a solid. The solid was filtered off with suction, washed with ethyl acetate and dried under high vacuum. This gave 5.640 g (93% of theory) of the target compound.

LC-MS (Method 1): $R_t$=0.59 min; MS (ESIpos): m/z=306 $(M-C_2H_3O_2)^+$ $^1$H NMR (400 MHz, DMSO-$d_6$): δ=1.83 (s, 3H), 5.87 (s, 2H), 7.06 (t, 1H), 7.26-7.37 (m, 2H), 8.43 (dd, 1H), 8.73 (s, 1H).

Example 70A 1-(2,2-Difluorobenzyl)-5-fluoro-1H-pyrazolo[3,4-b]pyridine-3-carboximidohydrazide

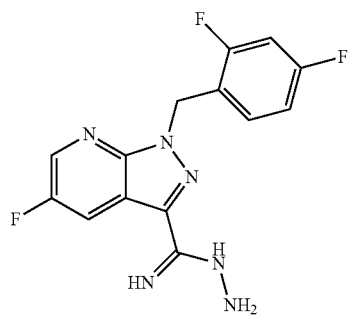 [SMILES: N=C(NN)c1nn(Cc2ccc(F)cc2F)c2ncc(F)cc12]

5.640 g (15.44 mmol) of Example 69A were dissolved in 76 ml of ethanol, and 6.249 g (61.76 mmol) of triethylamine and 0.966 g (15.44 mmol) of hydrazine hydrate (80% strength solution in water) were added at 0° C. The mixture was stirred at RT overnight and then concentrated on a rotary evaporator. This gave 5.30 g (100% of theory, purity 93%) of the title compound. The product was used without further purification for the next step.

LC-MS (Method 1): $R_t$=0.67 min; MS (ESIpos): m/z=321 $(M+H)^+$

Example 71A

Methyl 2-{4-[1-(2,4-difluorobenzyl)-5-fluoro-1H-pyrazolo[3,4-b]pyridin-3-yl]-2-hydroxyphenyl}-2-methylpropanoate

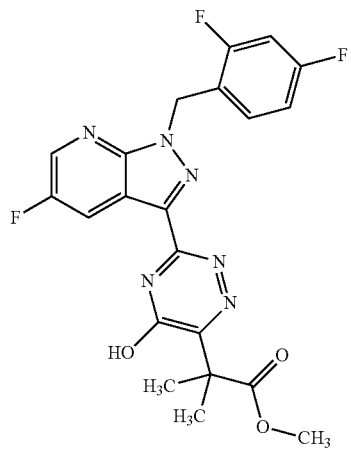 [SMILES: COC(=O)C(C)(C)c1nnc(-c2nn(Cc3ccc(F)cc3F)c3ncc(F)cc23)nc1O]

5.300 g (about 15.42 mmol) of Example 69A were dissolved in 140 ml of ethanol, 5.805 g (30.85 mmol) of dimethyl 2,2-dimethyl-3-oxobutanedioate (described in J. Am. Chem. Soc. 124(14), 3680-3691; 2002) were added and the mixture was stirred overnight. The solid formed was filtered off with suction and washed with a little ethanol, and the filtrate was concentrated. The residue was stirred with diethyl ether, filtered off with suction, washed with a little diethyl ether and dried under high vacuum. This gave 2.290 g (32% of theory) of the title compound.

LC-MS (Method 1): $R_t$=1.03 min; MS (ESIpos): m/z=459 $(M+H)^+$ $^1$H NMR (400 MHz, DMSO-$d_6$): δ [ppm]=1.44 (s, 6H), 3.55 (s, 3H), 5.86 (s, 2H), 7.07 (dt, 1H), 7.30 (dt, 1H), 7.42 (q, 1H), 8.43 (dd, 1H), 8.81 (s, 1H), 14.45 (s br, 1H).

Example 72A 5-2-[1-(2-Fluorobenzyl)-1H-pyrazolo[3,4-b]pyridin-3-yl]-5H-pyrrolo[2,3-d]pyrimidine-5,6(7H)-dione 5-oxime

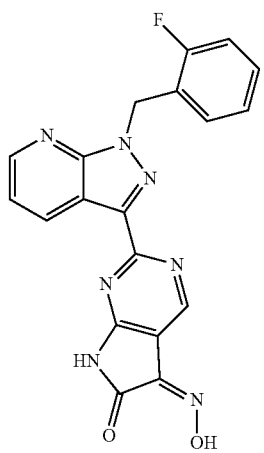 [SMILES: O=C1Nc2nc(-c3nn(Cc4ccccc4F)c4ncccc34)ncc2/C1=N/O]

700 mg (1.943 mmol) of Example 4 were suspended in acetic acid (14 ml), and 281 mg (4.079 mmol) of sodium nitrite and a few drops of water were added. After 30 min at RT, water was added and a precipitate was filtered off, washed with water and then dried under high vacuum. This gave 756 mg of the title compound (99% of theory).

LC-MS (Method 1): $R_t$=0.90 min; MS (ESIpos): m/z=390 $(M+H)^+$

Example 73A

5-Amino-2-[1-(2-fluorobenzyl)-1H-pyrazolo[3,4-b]pyridin-3-yl]-5,7-dihydro-6H-pyrrolo[2,3-d]-pyrimidin-6-one

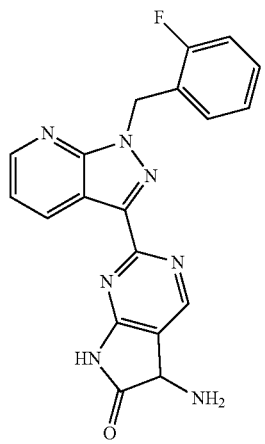 [SMILES: NC1C(=O)Nc2nc(-c3nn(Cc4ccccc4F)c4ncccc34)ncc21]

124 mg (0.319 mmol) of Example 72A were initially charged in trifluoroacetic acid (2.5 ml), 41 mg (0.637 mmol) of zinc dust were added and the mixture was stirred at RT overnight. The mixture was then concentrated and the crude material (about 150 mg) was used without purification for the next step.

LC-MS (Method 1): $R_t$=0.69 min; MS (ESIpos): m/z=376 (M+H)$^+$

Example 74A 1-(2,3-Difluorobenzyl)-1H-pyrazolo[3,4-b]pyridine-3-carboximidohydrazide

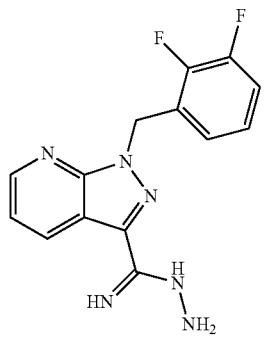 [SMILES: N=C(NN)c1nn(Cc2cccc(F)c2F)c2ncccc12]

10.00 g (28.791 mmol) of Example 36A were reacted analogously to Example 70A. This gave 11.74 g of the title compound in a purity of about 60% (81% of theory). The compound was used without further purification for the next step.

LC-MS (Method 1): $R_t$=0.57 min; MS (ESIpos): m/z=303 (M+H)$^+$

Example 75A

Methyl 2-{3-[1-(2,3-difluorobenzyl)-1H-pyrazolo[3,4-b]pyridin-3-yl]-5-hydroxy-1,2,4-triazin-6-yl}-2-methylpropanoate

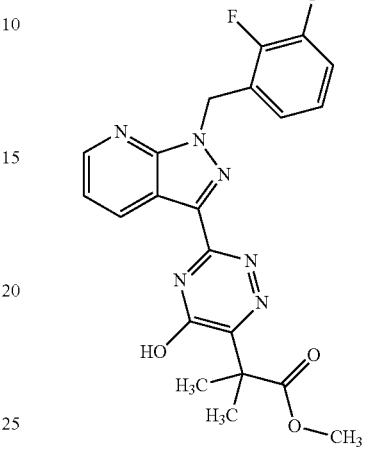

10.67 g (about 21.355 mmol) of Example 74A were dissolved in 300 ml of ethanol, 8.037 g (42.710 mmol) of dimethyl 2,2-dimethyl-3-oxobutanedioate (described in J. Am. Chem. Soc. 124(14), 3680-3691; 2002) were added and the mixture was stirred at 50° C. overnight. After cooling, a precipitate was filtered off and washed with ethanol. The residue was concentrated and then taken up in methanol (50 ml) and acetonitrile (50 ml) and purified by preparative HPLC (acetonitrile:water gradient). This gave 0.75 g (8% of theory) of the title compound.

LC-MS (Method 1): $R_t$=0.98 min; MS (ESIpos): m/z=441 (M+H)$^+$

Example 76A 1-(2,4-Difluorobenzyl)-1H-pyrazolo[3,4-b]pyridine-3-carboximidohydrazide

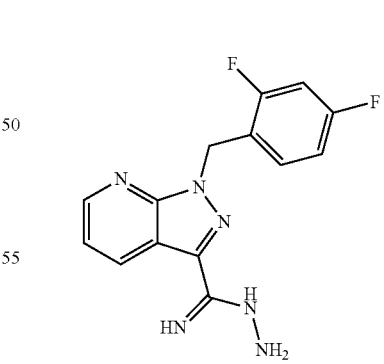

10.00 g (28.791 mmol) of Example 31A were reacted analogously to Example 70A. This gave 9.31 g of the title compound in a purity of about 82% (87% of theory). The compound was used without further purification for the next step.

LC-MS (Method 1): $R_t$=0.56 min; MS (ESIpos): m/z=303 (M+H)$^+$

Example 77A

Methyl 2-{3-[1-(2,4-difluorobenzyl)-1H-pyrazolo[3,4-b]pyridin-3-yl]-5-hydroxy-1,2,4-triazin-6-yl}-2-methylpropanoate

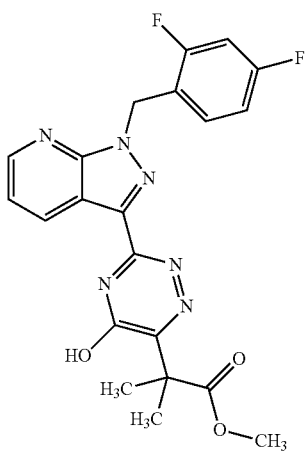 [SMILES: COC(=O)C(C)(C)c1nnc(-c2nn(Cc3ccc(F)cc3F)c3ncccc23)nc1O]

6.80 g (about 18.446 mmol) of Example 76A were dissolved in 272 ml of ethanol, 6.942 g (36.892 mmol) of dimethyl 2,2-dimethyl-3-oxobutanedioate (described in J. Am. Chem. Soc. 124(14), 3680-3691; 2002) were added and the mixture was stirred at 50° C. overnight. After cooling, a precipitate was filtered off and washed with ethanol. The residue was taken up in a large quantity of ethanol, resulting in the formation of another solid. This was filtered off and washed with ethanol and diethyl ether. The solid was dried and corresponded to the title compound 2.21 g (26% of theory). The filtrate was concentrated and then purified by preparative HPLC (acetonitrile:water:water+1% TFA–40:55:5). This gave an additional 0.64 g (7% of theory) of the title compound. In total, 2.85 g (33% of theory) of the title compound were obtained.

LC-MS (Method 1): $R_t$=1.03 min; MS (ESIpos): m/z=441 (M+H)$^+$

Example 78A

5-Fluoro-3-iodo-1-(2,3,6-trifluorobenzyl)-1H-pyrazolo[3,4-b]pyridine

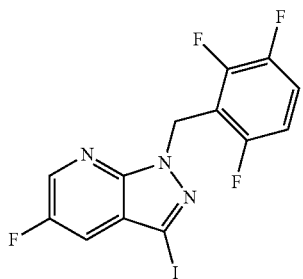 [SMILES: Fc1cnc2c(c1)c(I)nn2Cc1c(F)ccc(F)c1F]

10.0 g (38.021 mmol) of the compound from Example 6A were initially charged in DMF (170 ml), and 9.41 g (41.823 mmol) of 2,3,6-trifluorobenzyl bromide and 13.62 g (41.82 mmol) of caesium carbonate were then added. The mixture was stirred at RT overnight. The reaction mixture was then added to water (200 ml) and stirred for 15 min A precipitate was filtered off with suction, washed with water and subsequently dried under high vacuum. This gave 12.1 g of the title compound (78% of theory).

LC-MS (Method 1): $R_t$=1.24 min
MS (ESIpos): m/z=408 (M+H)$^+$
1H NMR (400 MHz, DMSO-$d_6$): δ=5.78 (s, 2H), 7.16-7.22 (m, 1H), 7.51-7.59 (m, 1H), 7.92 (dd, 1H), 8.73 (t, 1H).

Example 79A

5-Fluoro-1-(2,3,6-trifluorobenzyl)-1H-pyrazolo[3,4-b]pyridine-3-carbonitrile

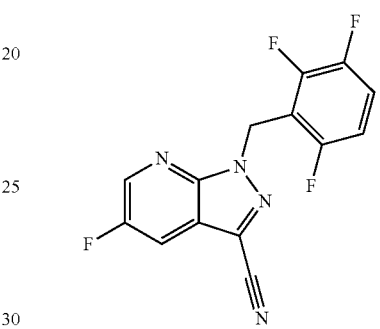

12.1 g (29.72 mmol) of Example 78A were reacted analogously to Example 8A. This gave 9.35 g of the title compound in a purity of 79% (81% of theory).

LC-MS (Method 1): $R_t$=1.08 min
MS (ESIpos): m/z=307 (M+H)$^+$
1H NMR (400 MHz, DMSO-d6): δ=5.91 (s, 2H), 7.21-7.23 (m, 1H), 7.57-7.61 (m, 1H), 8.51 (dd, 1H), 8.89 (t, 1H).

Example 80A

5-Fluoro-1-(2,3,6-trifluorobenzyl)-1H-pyrazolo[3,4-b]pyridine-3-carboximidamide acetate

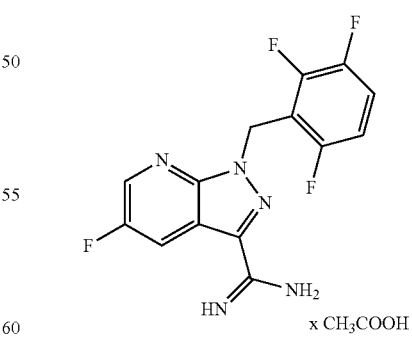

9.1 g of the crude compound of Example 79A were reacted analogously to Example 9A. This gave 7.77 g of the title compound (86% of theory).

LC-MS (Method 1): $R_t$=0.61 min
MS (ESIpos): m/z=324 (M+H)$^+$

Example 81A

5-Fluoro-1-(2,3,6-trifluorobenzyl)-1H-pyrazolo[3,4-b]pyridin-3-carboximidohydrazide

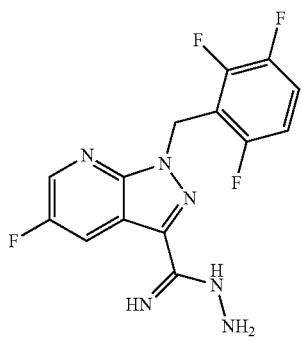 [SMILES: N=C(NN)c1nn(Cc2c(F)ccc(F)c2F)c2ncc(F)cc12]

7.77 g (20.271 mmol) of Example 80A were reacted analogously to the synthesis of Example 70A.

This gave 6.85 g of the title compound (99% of theory). The compound was used without further purification for the next step.

LC-MS (Method 1): $R_t$=0.59 min; MS (ESIpos): m/z=339 (M+H)$^+$

Example 82A

Methyl 2-{3-[5-fluoro-1-(2,3,6-trifluorobenzyl)-1H-pyrazolo[3,4-b]pyridin-3-yl]-5-hydroxy-1,2,4-triazin-6-yl}-2-methylpropanoate

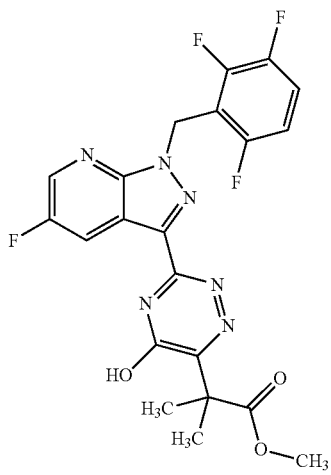 [SMILES: COC(=O)C(C)(C)c1nnc(-c2nn(Cc3c(F)ccc(F)c3F)c3ncc(F)cc23)nc1O]

6.85 g (20.271 mmol) of the compound from Example 81A were dissolved in 300 ml of ethanol, 7.629 g (40.542 mmol) of dimethyl 2,2-dimethyl-3-oxobutanedioate (described in J. Am. Chem. Soc. 124(14), 3680-3691; 2002) were added and the mixture was stirred at 50° C. overnight. After cooling, a precipitate was filtered off and washed with ethanol. The filtrate was concentrated and then purified by preparative HPLC (methanol:water-75:25). This gave 3.30 g (33% of theory) of the title compound.

LC-MS (Method 3): $R_t$=1.24 min; MS (ESIpos): m/z=477 (M+H)$^+$

Example 83A

Ethyl {2-[5-fluoro-1-(2-fluorobenzyl)-1H-pyrazolo[3,4-b]pyridin-3-yl]-4-hydroxypyrimidin-5-yl}-acetate

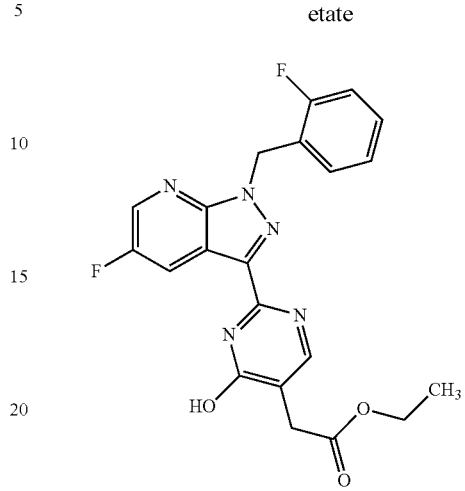

2.00 g (5.73 mmol) of Example 9A and 1.42 g (6.58 mmol) of diethyl 2-formylbutanedioate (synthesis described in WO 2005/73234, page 43) were initially charged in 50 ml of ethanol. 4.27 ml sodium ethoxide solution (21% strength in ethanol, 11.5 mmol) were then added dropwise. The mixture was then heated at reflux for 9 h. After cooling, 25 ml water and then 1 N hydrochloric acid were added to the reaction mixture. The precipitate that formed was filtered off with suction and washed successively with methanol (20 ml) and with diethyl ether (20 ml). Drying under high vacuum gave 1.53 g of the title compound (63% of theory).

LC-MS (Method 1): $R_t$=1.04 min; MS (ESIpos): m/z=426 (M+H)$^+$ $^1$H NMR (400 MHz, DMSO-$d_6$): δ [ppm]=1.19 (t, 3H), 3.48 (s, 2H), 4.09 (q, 2H), 5.86 (s, 2H), 7.16 (t, 1H), 7.24 (t, 1H), 7.31-7.34 (m, 2H), 8.11 (s br, 1H), 8.48 (d, 1H), 8.78 (s, 1H), 12.88 (s br, 1H).

Example 84A

Ethyl {4-chloro-2-[5-fluoro-1-(2-fluorobenzyl)-1H-pyrazolo[3,4-b]pyridin-3-yl]pyrimidin-5-yl}-acetate

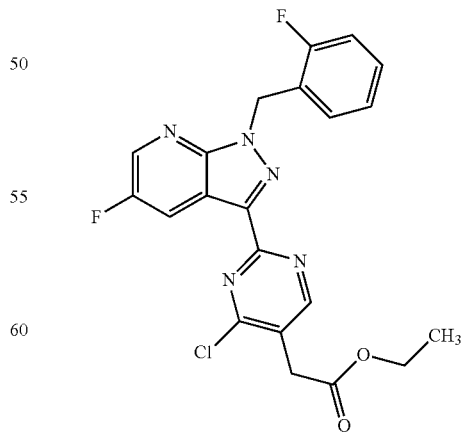

1.53 g (3.60 mmol) of Example 83A were initially charged in 3.35 ml (36.0 mmol) of phosphoryl chloride. 0.684 ml (5.40 mmol) of N,N-dimethylaniline was then added. The mixture was subsequently reacted in an oil bath at 150° C. for 1 h. The volatile components were separated off on a rotary evaporator and the residue was then carefully stirred into 50 ml of 2 M aqueous sodium carbonate solution. The mixture was stirred for 15 min and the solid was filtered off. The solid was taken up in ethyl acetate and washed with saturated aqueous sodium chloride solution, and the organic phase was dried with magnesium sulphate. The solvent was separated off by distillation under reduced pressure and the residue was dried under high vacuum overnight. This gave 1.44 g of the title compound (90% of theory).

LC-MS (Method 1): $R_t$=1.28 min; MS (ESIpos): m/z=444 $(M+H)^+$ $^1$H NMR (400 MHz, DMSO-d$_6$): δ [ppm]=1.21 (t, 3H), 3.99 (s, 2H), 4.15 (q, 2H), 5.90 (s, 2H), 7.17 (dt, 1H), 7.21-7.31 (m, 2H), 7.38 (m, 1H), 8.55 (dd, 1H), 8.79 (dd, 1H), 8.96 (s, 1H).

Example 85A

Ethyl 1-{4-chloro-2-[5-fluoro-1-(2-fluorobenzyl)-1H-pyrazolo[3,4-b]pyridin-3-yl]pyrimidin-5-yl}cyclopropanecarboxylate

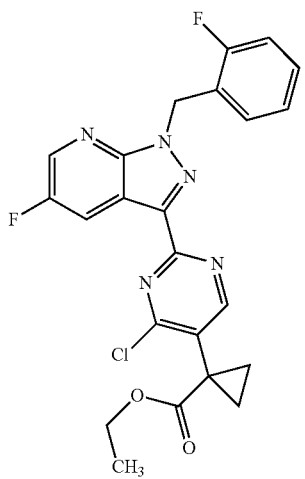 [SMILES: CCOC(=O)C1(c2cnc(-c3nn(Cc4ccccc4F)c4ncc(F)cc34)nc2Cl)CC1]

1.44 g (3.24 mmol) of Example 84A were initially charged in 40 ml of THF/DMF (v/v=1/1). 410 mg (16.2 mmol, 95% pure) of sodium hydride were then added a little at a time. The resulting solution was stirred for about 30 min (until the evolution of gas had ceased). 0.587 ml (6.81 mmol) of 1,2-dibromoethane was then added, and the mixture was stirred at room temperature for 1 h. The reaction mixture was hydrolysed with 50 ml of water and extracted with 50 ml of ethyl acetate. The organic phase was then washed with 50 ml water. The combined aqueous phases were extracted with ethyl acetate (2×30 ml) and the combined organic phases were then washed with saturated aqueous sodium chloride solution. After drying over magnesium sulphate, the solvent was separated off on a rotary evaporator. This gave 1.51 g of the title compound in a purity of about 80% (yield 79% of theory). The crude material was used without further work-up for the next step.

LC-MS (Method 1): $R_t$=1.36 min; MS (ESIpos): m/z=470 $(M+H)^+$ $^1$H NMR (400 MHz, DMSO-d$_6$): δ [ppm]=1.10 (t, 3H), 1.46 (m, 2H), 1.65 (m, 2H), 4.08 (q, 2H), 5.90 (s, 2H), 7.17 (t, 1H), 7.21-7.29 (m, 2H), 7.37 (m, 1H), 8.53 (dd, 1H), 8.79 (m, 1H), 8.94 (s, 1H).

Example 86A

Ethyl 1-{4-azido-2-[5-fluoro-1-(2-fluorobenzyl)-1H-pyrazolo[3,4-b]pyridin-3-yl]pyrimidin-5-yl}cyclopropanecarboxylate

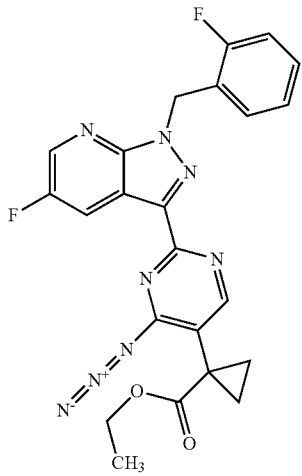 [SMILES: CCOC(=O)C1(c2cnc(-c3nn(Cc4ccccc4F)c4ncc(F)cc34)nc2N=[N+]=[N-])CC1]

1.51 g (2.57 mmol) of Example 85A were initially charged in 30 ml of DMF. 217 mg (3.34 mmol) of sodium azide were then added. The mixture was then stirred at 60° C. overnight. After cooling, 150 ml of water were added and the reaction mixture was extracted with ethyl acetate (3×70 ml). The combined organic phases were then washed with saturated aqueous sodium chloride solution. After drying with magnesium sulphate, the solvent was separated off on a rotary evaporator. This gave 1.15 g of the title compound in a purity of about 68% (93% of theory). The crude material was used without further work-up for the next step.

LC-MS (Method 1): $R_t$=1.33 min; MS (ESIpos): m/z=477 $(M+H)^+$

Example 87A

Ethyl 1-{4-amino-2-[5-fluoro-1-(2-fluorobenzyl)-1H-pyrazolo[3,4-b]pyridin-3-yl]pyrimidin-5-yl}cyclopropanecarboxylate

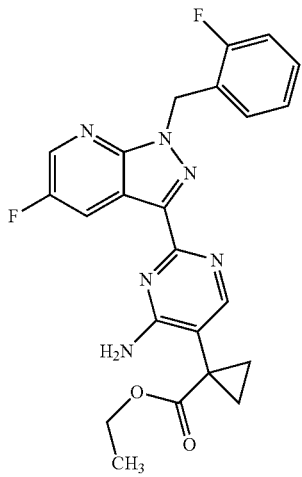 [SMILES: CCOC(=O)C1(c2cnc(-c3nn(Cc4ccccc4F)c4ncc(F)cc34)nc2N)CC1]

1.15 g (2.41 mmol) of Example 86A were initially charged in 30 ml of DMF. 500 mg (10%) of palladium on activated carbon were then added. The mixture was subsequently hydrogenated at a hydrogen pressure of 1 atmosphere for 3 h. The reaction mixture was filtered through Celite. The filter cake was washed with DMF and the volatile components were separated off on a rotary evaporator. The crude material obtained in this manner was dried under high vacuum overnight. This gave 1.28 g of crude material which contained the title compound in a purity of about 90% (LC-MS). The material obtained in this manner was used without further purification.

LC-MS (Method 3): $R_t$=1.11 min; MS (ESIpos): m/z=451 $(M+H)^+$

WORKING EXAMPLES

Example 1

2-[1-(2-Fluorobenzyl)-1H-pyrazolo[3,4-b]pyridin-3-yl]-5,5-dimethyl-5,7-dihydro-6H-pyrrolo[2,3-d]pyrimidin-6-one

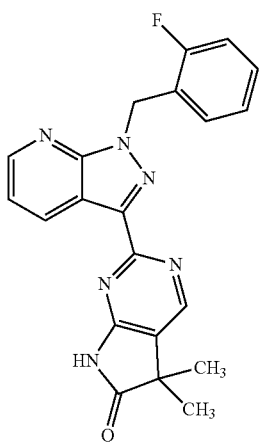 [SMILES: CC1(C)C(=O)Nc2nc(-c3nn(Cc4ccccc4F)c4ncccc34)ncc21]

425 mg of palladium on carbon (10%) were added to 1.00 g (1.944 mmol) of Example 55A in DMF (50 ml), and the mixture was hydrogenated at atmospheric hydrogen pressure for 4 h. The mixture was then filtered through Celite and concentrated to dryness. The residue was purified by preparative HPLC (acetonitrile:water (+0.05% formic acid) gradient). This gave 500 mg of the title compound (66% of theory).

LC-MS (Method 1): $R_t$=1.00 min; MS (ESIpos): m/z=389 $(M+H)^+$ $^1$H NMR (400 MHz, DMSO-d$_6$): δ [ppm]=1.38 (s, 6H), 5.86 (s, 2H), 7.13-7.17 (m, 1H), 7.21-7.26 (m, 2H), 7.34-7.39 (m, 1H), 7.44 (dd, 1H), 8.64 (s, 1H), 8.67 (dd, 1H), 8.87 (dd, 1H), 11.61 (s br, 1H).

Example 2

2-[5-Fluoro-1-(2-fluorobenzyl)-1H-pyrazolo[3,4-b]pyridin-3-yl]-5,5-dimethyl-5,7-dihydro-6H-pyrrolo[2,3-d]pyrimidin-6-one

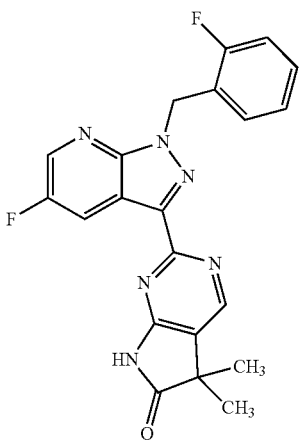 [SMILES: CC1(C)C(=O)Nc2nc(-c3nn(Cc4ccccc4F)c4ncc(F)cc34)ncc21]

1.74 g (about 1.944 mmol) of Example 56A were reacted analogously to Example 1. This gave 644 mg of the title compound (78% of theory).

LC-MS (Method 1): $R_t$=1.10 min; MS (ESIpos): m/z=407 $(M+H)^+$ $^1$H NMR (400 MHz, DMSO-d$_6$): δ [ppm]=1.38 (s, 6H), 5.85 (s, 2H), 7.14-7.18 (m, 1H), 7.21-7.28 (m, 2H), 7.35-7.40 (m, 1H), 8.59 (dd, 1H), 8.63 (s, 1H), 8.75 (dd, 1H), 11.58 (s br, 1H).

Example 3

2'-[1-(2-Fluorobenzyl)-1H-pyrazolo[3,4-b]pyridin-3-yl]-4,5-dihydrospiro[furan-3,5'-pyrrolo[2,3-d]pyrimidin]-6'(7'H)-one

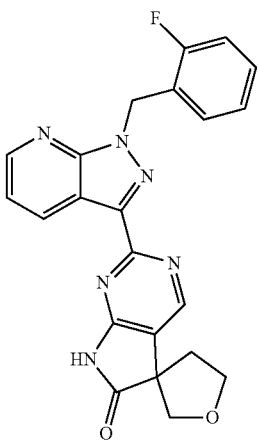 [SMILES: O=C1Nc2nc(-c3nn(Cc4ccccc4F)c4ncccc34)ncc2C12CCOC2]

96 mg (0.177 mmol) of Example 57A were reacted analogously to Example 1. This gave 51 mg of the title compound (68% of theory).

LC-MS (Method 1): R_t=0.92 min; MS (ESIpos): m/z=417 (M+H)+

¹H NMR (400 MHz, DMSO-d₆): δ [ppm]=2.23-2.29 (m, 1H), 2.34-2.41 (m, 1H), 3.89 (d, 1H), 3.97 (d, 1H), 4.07-4.11 (m, 1H), 4.12-4.18 (m, 1H), 5.86 (s, 2H), 7.13-7.17 (t, 1H), 7.21-7.26 (m, 2H), 7.34-7.39 (m, 1H), 7.44 (dd, 1H), 8.57 (s, 1H), 8.67 (dd, 1H), 8.87 (dd, 1H), 11.72 (s br, 1H).

Example 4

2-[1-(2-Fluorobenzyl)-1H-pyrazolo[3,4-b]pyridin-3-yl]-5,7-dihydro-6H-pyrrolo[2,3-d]pyrimidin-6-one

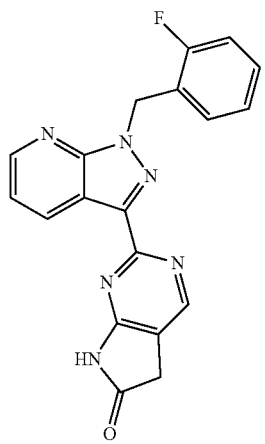 [SMILES: O=C1Cc2cnc(-c3nn(Cc4ccccc4F)c4ncccc34)nc2N1]

9.46 g (23.276 mmol) of Example 19A were initially charged in THF (400 ml), and 2.612 g (23.726 mmol) of potassium tert-butoxide were added. The mixture was stirred at RT for 1 h, water was then added, the pH was adjusted to pH=5 using acetic acid and the mixture was then stirred at RT for 10 min. The mixture was then extracted three times with ethyl acetate and the combined organic phases were washed with saturated aqueous sodium chloride solution. The organic phase was then dried over sodium sulphate, filtered and concentrated to dryness. The residue was slurried in methanol and filtered off with suction. The filter cake was washed repeatedly with methanol and then dried under high vacuum. This gave 6.61 g of the title compound as a solid (78% of theory).

LC-MS (Method 1): R_t=0.82 min; MS (ESIpos): m/z=361 (M+H)+

¹H NMR (400 MHz, DMSO-d₆): δ [ppm]=3.68 (s, 2H), 5.85 (s, 2H), 7.14-7.18 (m, 1H), 7.21-7.27 (m, 2H), 7.34-7.38 (m, 1H), 7.42 (dd, 1H), 8.49 (s, 1H), 8.67 (dd, 1H), 8.88 (dd, 1H), 11.58 (s, 1H).

Example 5

2'-[1-(2-Fluorobenzyl)-1H-pyrazolo[3,4-b]pyridin-3-yl]spiro[cyclopropane-1,5'-pyrrolo[2,3-d]pyrimidin]-6'(7'H)-one

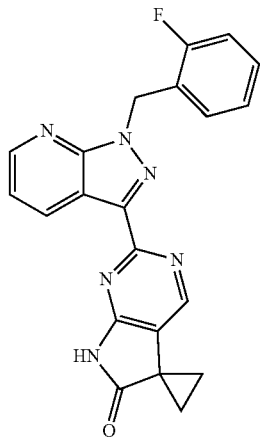 [SMILES: O=C1Nc2nc(-c3nn(Cc4ccccc4F)c4ncccc34)ncc2C12CC2]

394 mg (0.913 mmol) of Example 22A were reacted analogously to the procedure of Example 4. This gave 186 mg of the title compound (53% of theory).

LC-MS (Method 1): R_t=0.95 min; MS (ESIpos): m/z=387 (M+H)+

¹H NMR (400 MHz, DMSO-d₆): δ [ppm]=1.64 (ddd, 2H), 1.86 (ddd, 2H), 5.85 (s, 2H), 7.16 (t, 1H), 7.22-7.27 (m, 2H), 7.34-7.38 (m, 1H), 7.42 (dd, 1H), 8.39 (s, 1H), 8.67 (dd, 1H), 8.87 (dd, 1H), 11.78 (s br, 1H).

Example 6

3-[1-(2-Fluorobenzyl)-1H-pyrazolo[3,4-b]pyridin-3-yl]-5,7-dihydro-6H-pyrrolo[2,3-e][1,2,4]-triazin-6-one

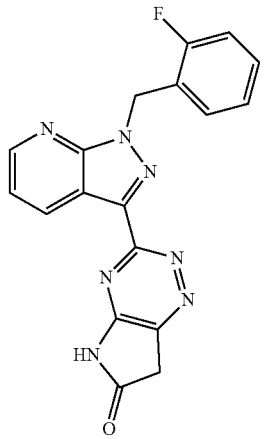 [SMILES: O=C1Cc2nnc(-c3nn(Cc4ccccc4F)c4ncccc34)nc2N1]

Step (a): Methyl {3-[7-(2-fluorobenzyl)-1H-pyrazolo[3,4-b]pyridin-3-yl]-5-hydroxy-1,2,4-triazin-6-yl}acetate 5.950 g (14.441 mmol) of the compound from Example 23A were dissolved in 70 ml of ethanol, and 3.351 g (20.929 mmol) of dimethyl 2-oxobutanedioate (described in Synth. Commun 9(7), 603-7; 1979) were added. The mixture was heated at reflux overnight. After cooling, the solid was filtered off with suction, washed with a little ethanol and dried under high vacuum (purity according to LC/MS=43%).

Step (b): Methyl {5-amino-3-[1-(2-fluorobenzyl)-1H-pyrazolo[3,4-b]pyridin-3-yl]-1,2,4-triazin-6-yl}acetate 14 ml of phosphoryl chloride were added to 1.100 g (1.199 mmol) of the intermediate from Step a), and the mixture was stirred at 100° C. for 1.75 h. After cooling, the reaction mixture was stirred into 100 ml of concentrated ammonia solution. The mixture was stirred at RT for 20 min. The precipitate formed was filtered off, washed with a little water and dried under high vacuum.

Step (c): 3-[1-(2-Fluorobenzyl)-1H-pyrazolo[3,4-b]pyridin-3-yl]-5,7-dihydro-6H-pyrrolo[2,3-e][1,2,4]triazin-6-one The intermediate from Step b) was dissolved in 350 ml of methanol, and 20 drops of a 1 N aqueous sodium hydroxide solution were added (pH=6). The mixture was stirred at RT overnight and concentrated on a rotary evaporator. The residue was purified on silica gel (mobile phase: dichloromethane/methanol, 96:4). This gave 67 mg (15% of theory) of the title compound.

LC-MS (Method 1): $R_t$=0.83 min; MS (EIpos): m/z=362 [M+H]+.

$^1$H NMR (400 MHz, DMSO-$d_6$): δ [ppm]=5.03 (s, 1H), 5.82 (s, 2H), 7.14-7.18 (m, 1H), 7.21-7.25 (m, 2H), 7.34-7.42 (m, 2H), 8.65-8.67 (m, 2H), 11.53 (s br, 1H), 13.55 (s br, 1H).

Example 7

4-(Difluoromethyl)-2-[1-(2-fluorobenzyl)-1H-pyrazolo[3,4-b]pyridin-3-yl]-5,5-dimethyl-5,7-dihydro-6H-pyrrolo[2,3-d]pyrimidin-6-one

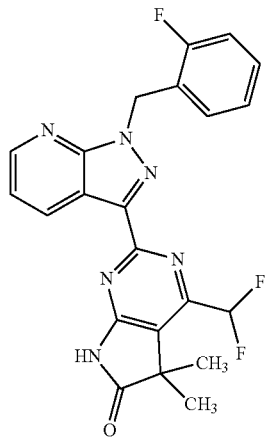 [SMILES: CC1(C)C(=O)Nc2nc(-c3nn(Cc4ccccc4F)c4ncccc34)nc(C(F)F)c21]

The crude product from Example 28A (1.24 g, about 1.312 mmol) was hydrogenated analogously to the procedure of Example 19A. The mixture was then filtered through Celite and concentrated. The residue was purified by preparative HPLC (mobile phase:acetonitrile/water with 0.1% formic acid). This gave 101 mg of the title compound (17% of theory).

LC-MS (Method 1): $R_t$=1.07 min; MS (EIpos): m/z=439 [M+H]+.

H NMR (400 MHz, DMSO-$d_6$): δ [ppm]=1.44 (s, 6H), 5.89 (s, 2H), 7.08-7.40 (m, 5H), 7.47 (dd, 1H), 8.69 (dd, 1H), 8.92 (dd, 1H), 12.00 (s br, 1H).

Example 8

2'-[1-(2,4-Difluorobenzyl)-1H-pyrazolo[3,4-b]pyridin-3-yl]spiro[cyclopropane-1,5'-pyrrolo[2,3-d]pyrimidin]-6'(7'H)-one

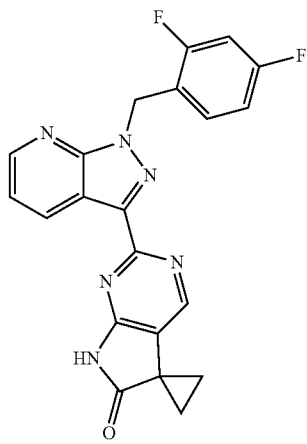 [SMILES: O=C1Nc2nc(-c3nn(Cc4ccc(F)cc4F)c4ncccc34)ncc2C12CC2]

Step (a): Ethyl 1-{4-chloro-2-[1-(2,4-difluorobenzyl)-1H-pyrazolo[3,4-b]pyridin-3-yl]pyrimidin-5-yl}cyclopropanecarboxylate Under argon, 0.80 g (1.802 mmol) of Example 33A were dissolved in 15 ml of DMF, 360 mg (9.012 mmol) of sodium hydride (60% suspension in mineral oil) were added and the mixture was stirred at RT for 15 min 1.015 g (5.407 mmol) of 1,2-dibromoethane was then added, and the mixture was stirred at RT for 2 h. Water and saturated aqueous sodium chloride solution were added and the mixture was extracted three times with ethyl acetate. The combined organic phases were dried over sodium sulphate and concentrated on a rotary evaporator. This gave 848 mg (purity 54%, 54% of theory) of the intermediate.

Step (b): Ethyl 1-{4-amino-2-[1-(2,4-difluorobenzyl)-1H-pyrazolo[3,4-b]pyridin-3-yl]pyrimidin-5-yl}cyclopropanecarboxylate The intermediate from Step a) was dissolved in 13 ml of DMF, and 95 mg (1.461 mmol) of sodium azide were added. The reaction mixture was stirred at 60° C. for 7 h and then, after cooling, added to water. The mixture was extracted three times with ethyl acetate. The combined organic phases were washed with saturated aqueous sodium chloride solution and dried over sodium sulphate, 10 ml of DMF were added and the ethyl acetate was removed on a rotary evaporator at 80 mbar. 20 ml of DMF were added to the product-containing DMF solution, 250 mg of palladium (10% on carbon) were added and the mixture was hydrogenated at atmospheric pressure overnight. The reaction solution was filtered through Celite and the filter cake was washed with DMF. The combined organic phases were concentrated on a rotary evaporator.

Step (c): 2'-[1-(2,4-Difluorobenzyl)-1H-pyrazolo[3,4-b]pyridin-3-yl]spiro[cyclopropane-1,5'-pyrrolo[2,3-d]pyrimidin]-6'(7'H)-one The intermediate from Step b) was taken up in 20 ml of THF, 109 mg (0.974 mmol) of potassium tert-butoxide were added under an atmosphere of argon and the mixture was stirred at RT for 2 h. Water was added, and the pH of the reaction mixture was adjusted to pH=5 with acetic acid. The mixture was stirred at RT for 10 min and the mixture was extracted with ethyl acetate. The combined organic phases were dried over sodium sulphate and concentrated on a rotary evaporator. The residue was purified by preparative HPLC (mobile phase:acetonitrile/water with 0.1% formic acid, gradient 50:50→70:30). This gave 101 mg of the title compound (25% of theory).

LC-MS (Method 1): R$_t$=0.93 min; MS (EIpos): m/z=405 [M+H]$^+$.

$^1$H NMR (400 MHz, DMSO-d$_6$): δ [ppm]=1.62-1.65 (m, 2H), 1.85-1.88 (m, 2H), 5.82 (s, 2H), 7.07 (dt, 1H), 7.29 (dt, 1H), 7.34-7.44 (m, 2H), 8.39 (s, 1H), 8.67 (d, 1H), 8.87 (d, 1H), 11.77 (s br, 1H).

Example 9

3-[1-(2-Fluorobenzyl)-1H-pyrazolo[3,4-b]pyridin-3-yl]-7,7-dimethyl-5,7-dihydro-6H-pyrrolo[2,3-e][1,2,4]triazin-6-one

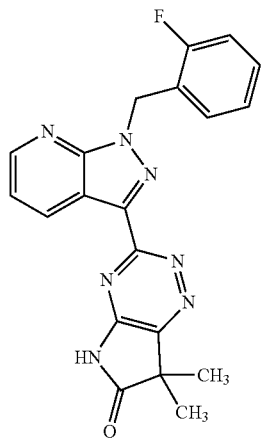 [SMILES: CC1(C)C(=O)Nc2nc(-c3nn(Cc4ccccc4F)c4ncccc34)nnc21]

Step (a): Methyl 2-{3-[1-(2-fluorobenzyl)-1H-pyrazolo[3,4-b]pyridin-3-yl]-5-hydroxy-1,2,4-triazin-6-yl}-2-methylpropanoate 6.00 g (14.562 mmol) of the compound from Example 23A were dissolved in 70 ml of ethanol, and 2.740 g (14.562 mmol) of dimethyl 2,2-dimethyl-3-oxobutanedioate (described in J. Am. Chem. Soc. 124(14), 3680-3691; 2002) were added. The mixture was heated at reflux overnight. After cooling, the solid was filtered off with suction and washed with a little ethanol, and the filtrate was concentrated and dried under high vacuum.

Step (b): 3-[1-(2-Fluorobenzyl)-1H-pyrazolo[3,4-b]pyridin-3-yl]-7,7-dimethyl-5,7-dihydro-6H-pyrrolo[2,3-e][1,2,4]triazin-6-one 35 ml of phosphoryl chloride were added to the intermediate from Step a), and the mixture was stirred overnight. The reaction mixture was dissolved in 500 ml of acetonitrile and, with ice cooling, stirred into 300 ml of concentrated ammonia solution. The mixture was stirred at RT for 2 h and concentrated on a rotary evaporator. The residue was stirred with water and ethyl acetate and the aqueous phase was extracted with ethyl acetate. The combined organic phases were dried over sodium sulphate and concentrated on a rotary evaporator. The residue was purified by preparative HPLC (mobile phase:methanol/water, gradient 30:70→90:10). This gave 701 mg (25% of theory) of the title compound.

LC-MS (Method 1): R$_t$=0.96 min; MS (EIpos): m/z=405 [M+H]$^+$.

$^1$H NMR (400 MHz, DMSO-d$_6$): δ [ppm]=1.45 (s, 6H), 5.89 (s, 2H), 7.15 (dt, 1H), 7.21-7.27 (m, 2H), 7.34-7.40 (m, 1H), 7.48 (dd, 1H), 8.71 (dd, 1H), 8.86 (dd, 1H), 12.16 (s, 1H).

Example 10

2'-[1-(2,3-Difluorobenzyl)-1H-pyrazolo[3,4-b]pyridin-3-yl]spiro[cyclopropane-1,5'-pyrrolo[2,3-d]pyrimidin]-6'(7'H)-one

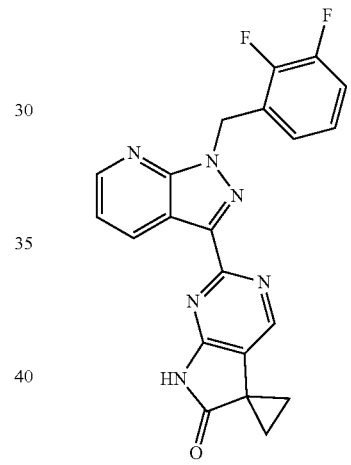

Step (a): Ethyl 1-{4-chloro-2-[1-(2,3-difluorobenzyl)-1H-pyrazolo[3,4-b]pyridin-3-yl]pyrimidin-5-yl}clopropanecarboxylate Under argon, 0.80 g (1.802 mmol) of the compound obtained in Example 38A were dissolved in 15 ml of DMF, 360 mg (9.012 mmol) of sodium hydride (60% suspension in oil) were added and the mixture was stirred at RT for 15 min 1.015 g (5.407 mmol) of 1,2-dibromoethane were then added, and the mixture was stirred at RT for 2 h. Water and saturated aqueous sodium chloride solution were added, and the mixture was extracted three times with ethyl acetate. The combined organic phases were dried over sodium sulphate and concentrated on a rotary evaporator. This gave 902 mg (purity 70%, 75% of theory) of the intermediate.

Step (b): Ethyl 1-{4-amino-2-[1-(2,3-difluorobenzyl)-1H-pyrazolo[3,4-b]pyridin-3-yl]pyrimidin-5-yl}clopropanecarboxylate The intermediate from Step a) was dissolved in 13 ml of DMF, and 131 mg (2.020 mmol) of sodium azide were added.

The reaction mixture was stirred at 60° C. for 7 h and, after cooling, added to water. The mixture was extracted three times with ethyl acetate. The combined organic phases were washed with saturated aqueous sodium chloride solution and dried over sodium, 10 ml of DMF were added and the ethyl acetate was removed on a rotary evaporator at 80 mbar. 20 ml of DMF were added to the product-containing DMF solution, 250 mg of palladium (10% on carbon) were added and the mixture was hydrogenated at atmospheric pressure for 2 h. The reaction solution was filtered through Celite and the filter cake was washed with DMF. The combined organic phases were concentrated on a rotary evaporator.

Step (c): 2'-[1-(2,3-Difluorobenzyl)-1H-pyrazolo[3,4-b]pyridin-3-yl]spiro[cyclopropane-1,5-pyrrolo[2,3-d]pyrimidin]-6'(7'H)-one The residue was taken up in 25 ml of THF, 151 mg (1.346 mmol) of potassium tert-butoxide were added under an atmosphere of argon and the mixture was stirred at RT for 2 h. Water was added to the reaction mixture and the pH was adjusted to pH=5 using acetic acid. The mixture was stirred at RT for 10 min and extracted with ethyl acetate. The combined organic phases were dried over sodium sulphate and concentrated on a rotary evaporator. The residue was purified by preparative HPLC (mobile phase:acetonitrile/water with 0.1% formic acid, gradient 50:50→70:30). This gave 227 mg of the title compound (42% of theory).

LC-MS (Method 1): $R_t$=0.93 min; MS (EIpos): m/z=405 [M+H]+.

$^1$H NMR (400 MHz, DMSO-$d_6$): δ [ppm]=1.62-1.65 (m, 2H), 1.85-1.88 (m, 2H), 5.90 (s, 2H), 7.06-7.10 (m, 1H), 7.15-7.21 (m, 1H), 7.37-7.46 (m, 2H), 8.39 (s, 1H), 8.68 (dd, 1H), 8.88 (dd, 1H), 11.78 (s br, 1H).

Example 11

2-[1-(2,3-Difluorobenzyl)-1H-pyrazolo[3,4-b]pyridin-3-yl]-5,5-dimethyl-5,7-dihydro-6H-pyrrolo[2,3-d]pyrimidin-6-one

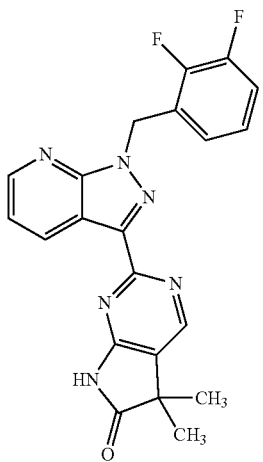 [SMILES: CC1(C)C(=O)Nc2nc(-c3nn(Cc4cccc(F)c4F)c4ncccc34)ncc21]

0.86 g (about 1.800 mmol) of the compound obtained in Example 41A was reacted analogously to the procedure of Example 4. This gave 331 mg of the title compound (45% of theory).

LC-MS (Method 1): $R_t$=0.98 min; MS (EIpos): m/z=407 [M+H]+.

$^1$H NMR (400 MHz, DMSO-$d_6$): δ [ppm]=1.38 (s, 6H), 5.91 (s, 2H), 7.05 (t, 1H), 7.14-7.20 (m, 1H), 7.36-7.41 (m, 1H), 7.44 (dd, 1H), 8.65 (s, 1H), 8.68 (dd, 1H), 8.88 (dd, 1H), 11.59 (s br, 1H).

Example 12

4-Cyclopropyl-2-[1-(2-fluorobenzyl)-1H-pyrazolo[3,4-b]pyridin-3-yl]-5,5-dimethyl-5,7-dihydro-6H-pyrrolo[2,3-d]pyrimidin-6-one

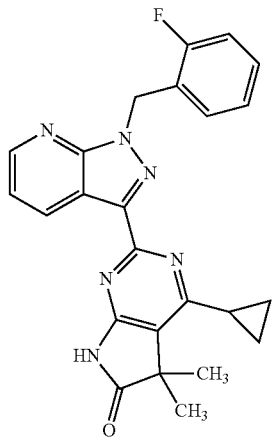 [SMILES: CC1(C)C(=O)Nc2nc(-c3nn(Cc4ccccc4F)c4ncccc34)nc(C3CC3)c21]

The solution obtained in Example 47A was hydrogenated analogously to Example 19A. Purification by preparative HPLC (mobile phase:acetonitrile/water with 0.1% formic acid) gave 48 mg of the title compound (7% of theory).

LC-MS (Method 1): $R_t$=1.14 min; MS (EIpos): m/z=429 [M+H]+.

$^1$H NMR (400 MHz, DMSO-$d_6$): δ [ppm]=1.14-1.18 (m, 2H), 1.27-1.30 (m, 2H), 1.48 (s, 6H), 2.23-2.27 (m, 1H), 5.84 (s, 2H), 7.12-7.25 (m, 3H), 7.33-7.38 (m, 1H), 7.45 (dd, 1H), 8.39 (s, 1H), 8.66 (dd, 1H), 8.69 (dd, 1H), 11.52 (s br, 1H).

Example 13

2-[1-(2,4-Difluorobenzyl)-1H-pyrazolo[3,4-b]pyridin-3-yl]-5,5-dimethyl-5,7-dihydro-6H-pyrrolo[2,3-d]pyrimidin-6-one

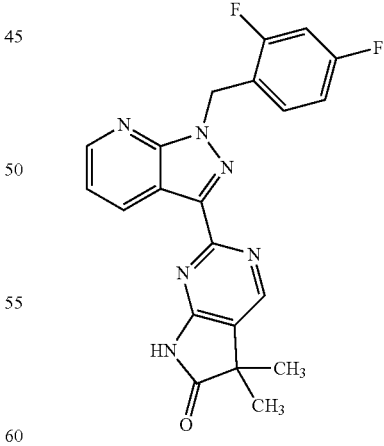

0.75 g (about 1.269 mmol) of the compound obtained in Example 50A was reacted analogously to the procedure of Example 4. This gave 193 mg of the title compound (37% of theory).

LC-MS (Method 1): $R_t$=0.97 min; MS (EIpos): m/z=407 [M+H]+.

$^1$H NMR (400 MHz, DMSO-d$_6$): δ [ppm]=1.38 (s, 6H), 5.83 (s, 2H), 7.06 (ddd, 1H), 7.26-7.38 (m, 2H), 7.43 (dd, 1H), 8.64 (s, 1H), 8.68 (dd, 1H), 8.87 (dd, 1H), 11.59 (s br, 1H).

Example 14

2-[1-(2-Fluorobenzyl)-1H-pyrazolo[3,4-b]pyridin-3-yl]-5-methyl-5,8-dihydropyrido[2,3-d]-pyrimidin-7(6H)-one

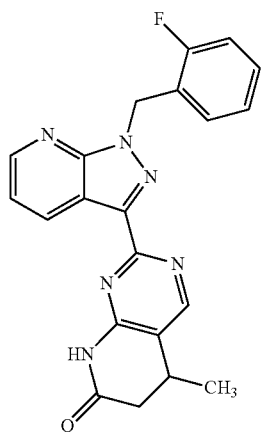

168 mg (0.327 mmol) of Example 58A were reacted analogously to Example 1. This gave 71 mg of the title compound (56% of theory).

LC-MS (Method 1): R$_t$=0.95 min; MS (ESIpos): m/z=389 (M+H)$^+$ $^1$H NMR (400 MHz, DMSO-d$_6$): δ [ppm]=1.27 (d, 3H), 2.43 (dd, 1H), 2.76 (dd, 1H), 3.21-3.27 (m, 1H), 5.85 (s, 2H), 7.12-7.26 (m, 3H), 7.33-7.43 (m, 2H), 8.61 (s, 1H), 8.66 (dd, 1H), 9.04 (dd, 1H), 11.20 (s, 1H).

Example 15

2-[1-(2-Fluorobenzyl)-1H-pyrazolo[3,4-b]pyridin-3-yl]-5-(trifluoromethyl)-5,8-dihydropyrido[2,3-d]pyrimidin-7(6H)-one

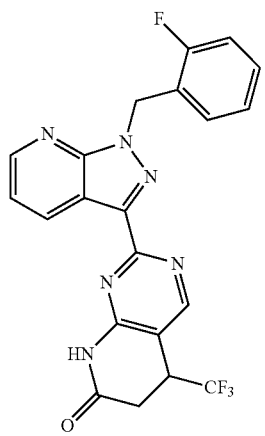 [SMILES: CC1CC(=O)Nc2nc(-c3nn(Cc4ccccc4F)c4ncccc34)ncc21]

603 mg (1.061 mmol) of the compound obtained in Example 59A were reacted analogously to Example 1. This gave 174 mg of the title compound (37% of theory).

LC-MS (Method 1): R$_t$=1.01 min; MS (ESIpos): m/z=443 (M+H)$^+$ $^1$H NMR (400 MHz, DMSO-d$_6$): δ [ppm]=2.75 (d, 1H), 3.29 (signal partially under water signal, 1H), 4.32-4.40 (m, 1H), 5.87 (s, 2H), 7.13-7.26 (m, 3H), 7.34-7.40 (m, 1H), 7.44 (dd, 1H), 8.68 (dd, 1H), 8.77 (s, 1H), 9.06 (dd, 1H), 11.55 (s, 1H).

Example 16

2-[1-(2-Fluorobenzyl)-1H-pyrazolo[3,4-b]pyridin-3-yl]-5H-pyrrolo[2,3-d]pyrimidine-5,6(7H)-dione

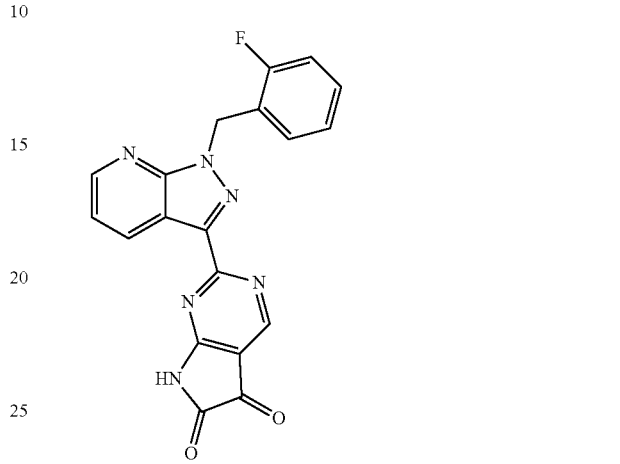

2.00 g (5.550 mmol) of Example 4 were initially charged in dioxane (200 ml), 3.079 g (27.751 mmol) of selenium dioxide were added and the mixture was heated at reflux for 2 h. After cooling, the mixture was filtered and the filtrate was concentrated and purified by chromatography on silica gel (mobile phase:cyclohexane/ethyl acetate 1:1). This gave 890 mg of the title compound (42% of theory).

LC-MS (Method 1): R$_t$=0.93 min; MS (ESIpos): m/z=375 (M+H)$^+$

1H NMR (400 MHz, DMSO-d6): δ [ppm]=5.91 (s, 2H), 7.17 (ddd, 1H), 7.21-7.26 (m, 1H), 7.27-7.31 (ddd, 1H), 7.35-7.41 (m, 1H), 7.51 (dd, 1H), 8.72 (dd, 1H), 8.87 (s, 1H), 8.89 (dd, 1H), 12.21 (s, 1H).

Example 17

2-[1-(2-Fluorobenzyl)-1H-pyrazolo[3,4-b]pyridin-3-yl]-5-hydroxy-5-methyl-5,7-dihydro-6H-pyrrolo[2,3-d]pyrimidin-6-one

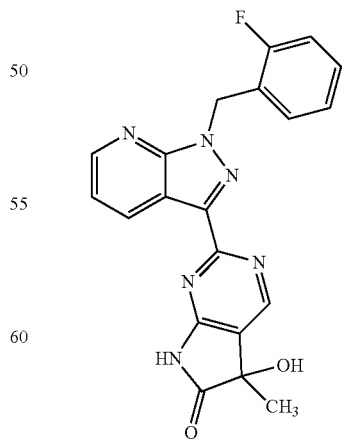

At 0° C., 200 mg (0.534 mmol) of Example 16 were initially charged in THF (10 ml), and 0.356 ml (1.069 mmol) of methylmagnesium bromide (3 M solution in diethyl ether) was added. After 15 min at 0° C., the mixture was heated at RT for 1 h. The mixture was then added to saturated aqueous ammonium chloride solution and extracted three times with ethyl acetate. The organic phases were combined and washed once with water and once with saturated aqueous sodium chloride solution. The organic phase was then dried over sodium sulphate, filtered and concentrated. The residue was purified by preparative HPLC (acetonitrile:water (+0.05% formic acid) gradient). This gave 55 mg of the title compound (53% of theory).

LC-MS (Method 1): $R_t$=0.81 min; MS (ESIpos): m/z=391 $(M+H)^+$

1H NMR (400 MHz, DMSO-d6): δ [ppm]=1.50 (s, 3H), 5.86 (s, 2H), 6.29 (s, 1H), 7.16 (ddd, 1H), 7.21-7.26 (m, 2H), 7.34-7.39 (m, 1H), 7.44 (dd, 1H), 8.61 (s, 1H), 8.68 (dd, 1H), 8.87 (dd, 1H), 11.53 (s, 1H).

Example 18

2-[1-(2-Fluorobenzyl)-1H-pyrazolo[3,4-b]pyridin-3-yl]-5-hydroxy-5-(trifluoromethyl)-5,7-dihydro-6H-pyrrolo[2,3-d]pyrimidin-6-one

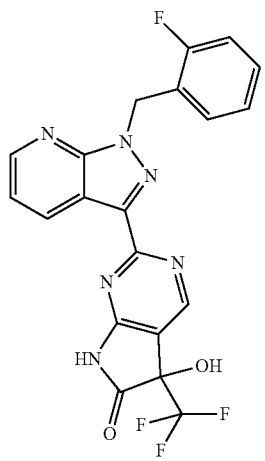 [SMILES: O=C1Nc2nc(-c3nn(Cc4ccccc4F)c4ncccc34)ncc2C1(O)C(F)(F)F]

At RT, 150 mg (0.401 mmol) of Example 16 were initially charged in 1,2-dimethoxyethane (3 ml), and 6 mg (0.04 mmol) of caesium fluoride were added. 177 µl (1.202 mmol) of (trifluoromethyl)-trimethylsilane were then added dropwise, and the mixture was stirred at RT overnight. More of the following reagents was then added: 1,2-dimethoxyethane (2 ml), caesium fluoride (20 mg) and (trifluoromethyl)trimethylsilane (177 µl). After another night, more caesium fluoride (20 mg) and (trifluoromethyl)trimethylsilane (2.404 ml, 0.5 M in THF) were added. The reaction was stirred for another 2 days and then allowed to stand at RT without stirring for 2 more days. The mixture was then concentrated and the residue was purified by preparative HPLC (acetonitrile:water (+0.05% formic acid) gradient). This gave 8 mg of the title compound (4% of theory).

LC-MS (Method 1): $R_t$=1.01 min; MS (ESIpos): m/z=445 $(M+H)^+$

1H NMR (400 MHz, DMSO-d6): δ [ppm]=5.88 (s, 2H), 7.16 (t, 1H), 7.22-7.29 (m, 2H), 7.35-7.41 (m, 1H), 7.47 (dd, 1H), 8.61 (s, 1H), 8.15 (s, 1H), 8.71 (dd, 1H), 8.76 (s, 1H), 8.87 (dd, 1H), 12.28 (s, 1H).

Example 19

3-[1-(2-Fluorobenzyl)-1H-pyrazolo[3,4-b]pyridin-3-yl]-7,7-dimethyl-5,7-dihydro-6H-pyrrolo[2,3-e][1,2,4]triazin-6-one

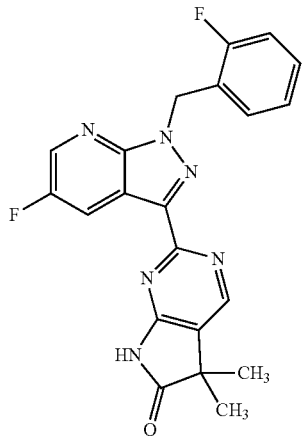 [SMILES: CC1(C)C(=O)Nc2nc(-c3nn(Cc4ccccc4F)c4ncc(F)cc34)ncc21]

50 ml of phosphoryl chloride were added to 9.700 g (22.025 mmol) of the compound from Example 61A, and the mixture was stirred at RT overnight. The reaction mixture was dissolved in 150 ml of acetonitrile and, with ice cooling, stirred into a mixture of 1337 ml of concentrated aqueous ammonia solution (35% strength) and 1300 ml of acetonitrile. The mixture was stirred at room temperature for 2 days. 300 g of sodium chloride were then added. Two phases formed. The organic phase was separated off and concentrated to dryness. The residue was taken up in ethyl acetate (150 ml). A precipitate formed and was filtered off with suction through a frit. The filter cake was washed three times with water and then three times with ethyl acetate (5 ml). The residue was dried under high vacuum. This gave 4.58 g (51% of theory) of the title compound.

LC-MS (Method 1): $R_t$=0.99 min; MS (EIpos): m/z=408 [M+H]+.

$^1$H NMR (400 MHz, DMSO-$d_6$): δ [ppm]=1.45 (s, 6H), 5.88 (s, 2H), 7.15-7.30 (m, 3H), 7.35-7.41 (m, 1H), 8.56 (dd, 1H), 8.79 (dd, 1H), 12.18 (s br, 1H).

Example 20

3-[1-(2,3-Difluorobenzyl)-5-fluoro-1H-pyrazolo[3,4-b]pyridin-3-yl]-7,7-dimethyl-5,7-dihydro-6H-pyrrolo[2,3-e][1,2,4]triazin-6-one

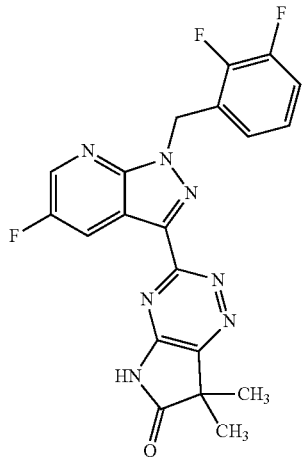 [SMILES: CC1(C)C(=O)Nc2nc(-c3nn(Cc4cccc(F)c4F)c4ncc(F)cc34)nnc21]

22 ml of phosphoryl chloride were added to 2.060 g (4.49 mmol) of the compound from Example 66A, and the mixture was stirred at RT overnight. The reaction mixture was dissolved in 100 ml of acetonitrile and, with ice cooling, stirred into 290 ml of concentrated aqueous ammonia solution (35% strength). The reaction mixture was stirred at room temperature for 2 h and then at 50° C. for 7 h and subsequently concentrated on a rotary evaporator. The residue was stirred with water and ethyl acetate and the aqueous phase was extracted with ethyl acetate. The combined organic phases were dried over sodium sulphate and concentrated on a rotary evaporator. The residue was triturated with diethyl ether, filtered off with suction, washed with a little diethyl ether and dried under high vacuum. This gave 748 mg (37% of theory) of the title compound.

LC-MS (Method 3): $R_t$=1.23 min; MS (EIpos): m/z=426 [M+H]+.

$^1$H NMR (400 MHz, DMSO-d$_6$): δ [ppm]=1.45 (s, 6H), 5.94 (s, 2H), 7.09-7.21 (m, 2H), 7.41 (q, 1H), 8.57 (dd, 1H), 8.80 (s, 1H), 12.18 (s br, 1H).

Example 21

3-[1-(2,4-Difluorobenzyl)-5-fluoro-1H-pyrazolo[3,4-b]pyridin-3-yl]-7,7-dimethyl-5,7-dihydro-6H-pyrrolo[2,3-e][1,2,4]triazin-6-one

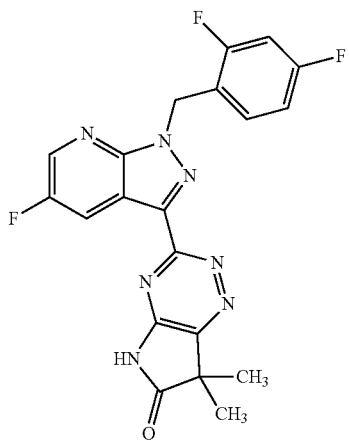 [SMILES: CC1(C)C(=O)Nc2nc(-c3nn(Cc4ccc(F)cc4F)c4ncc(F)cc34)nnc21]

25 ml of phosphoryl chloride were added to 2.290 g (5.000 mmol) of the compound from Example 71A, and the mixture was stirred at RT overnight. The reaction mixture was dissolved in 120 ml of acetonitrile and, with ice cooling, stirred into 350 ml of concentrated aqueous ammonia solution (35% strength). The reaction mixture was stirred at room temperature for 2 h and then at 50° C. for 6 h and subsequently concentrated on a rotary evaporator. The residue was stirred with water and ethyl acetate and the aqueous phase was extracted with ethyl acetate. The combined organic phases were dried over sodium sulphate and concentrated on a rotary evaporator. The residue was triturated with diethyl ether, filtered off with suction, washed with a little diethyl ether and dried under high vacuum. This gave 1.020 g (47% of theory) of the title compound.

LC-MS (Method 4): $R_t$=1.06 min; MS (EIpos): m/z=426 [M+H]+.

$^1$H NMR (400 MHz, DMSO-d$_6$): δ [ppm]=1.45 (s, 6H), 5.86 (s, 2H), 7.09 (dt, 1H), 7.29 (dt, 1H), 7.41 (q, 1H), 8.55 (dd, 1H), 8.79 (s, 1H), 12.19 (s br, 1H).

Example 22

2-[1-(2-Fluorobenzyl)-1H-pyrazolo[3,4-b]pyridin-3-yl]-5-hydroxy-5-phenyl-5,7-dihydro-6H-pyrrolo[2,3-d]pyrimidin-6-one

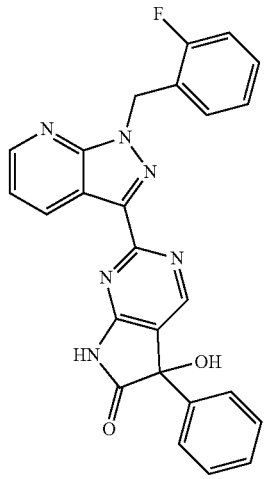 [SMILES: O=C1Nc2nc(-c3nn(Cc4ccccc4F)c4ncccc34)ncc2C1(O)c1ccccc1]

At 0° C., 75 mg (0.200 mmol) of Example 16 were initially charged in THF (5 ml), and 0.134 ml of a 3 M solution of phenylmagnesium bromide in diethyl ether (0.401 mmol) were added. After 15 min at 0° C., the mixture was warmed at RT for 1 h. The mixture was then added to saturated aqueous ammonium chloride solution and extracted three times with ethyl acetate. The organic phases were combined and washed once with water and once with saturated aqueous sodium chloride solution. The organic phases were then dried over sodium sulphate, filtered and concentrated. The residue was purified by preparative HPLC (acetonitrile:water (+0.05% formic acid) gradient). This gave 38 mg of the title compound (42% of theory).

LC-MS (Method 1): $R_t$=1.03 min; MS (ESIpos): m/z=453 $(M+H)^+$ $^1$H NMR (400 MHz, DMSO-d$_6$): δ [ppm]=5.87 (d, 2H), 7.08 (s, 1H), 7.17 (dd, 1H), 7.22-7.29 (m, 2H), 7.33-7.47 (m, 7H), 8.48 (s, 1H), 8.69 (dd, 1H), 8.88 (dd, 1H), 11.76 (br s, 1H).

Example 23

5-Fluoro-2-[1-(2-fluorobenzyl)-1H-pyrazolo[3,4-b]pyridin-3-yl]-5-methyl-5,7-dihydro-6H-pyrrolo[2,3-d]pyrimidin-6-one

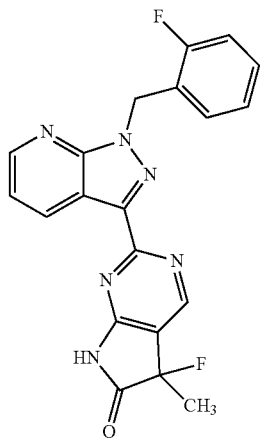 [SMILES: CC1(F)C(=O)Nc2nc(-c3nn(Cc4ccccc4F)c4ncccc34)ncc21]

At −78° C., 100 mg (0.256 mmol) of Example 17 were initially charged in dichloromethane (4.795 ml), and 40.61 μl (0.307 mmol) of diethylaminosulphur trifluoride were added. Overnight, the mixture was then slowly warmed to RT. Another 40.61 μl (0.307 mmol) of diethylaminosulphur trifluoride were then added, and the mixture was stirred at RT for another night. The reaction was then diluted with dichloromethane and extracted with saturated aqueous sodium bicarbonate solution. The organic phase was dried over sodium sulphate, filtered and concentrated. The residue was purified by preparative HPLC (acetonitrile:water (+0.05% formic acid) gradient). This gave 42 mg of the title compound (42% of theory).

LC-MS (Method 1): $R_t$=0.96 min; MS (ESIpos): m/z=393 $(M+H)^+$ $^1$H NMR (400 MHz, DMSO-$d_6$): δ [ppm]=1.82 (s, 3H), 5.88 (s, 2H), 7.16 (ddd, 1H), 7.21-7.28 (m, 2H), 7.34-7.40 (m, 1H), 7.46 (dd, 1H), 8.70 (dd, 1H), 8.86-8.89 (m, 2H), 12.01 (s, 1H).

Example 24 tert-Butyl {2-[1-(2-fluorobenzyl)-1H-pyrazolo[3,4-b]pyridin-3-yl]-5-hydroxy-6-oxo-6,7-dihydro-5H-pyrrolo[2,3-d]pyrimidin-5-yl}acetate

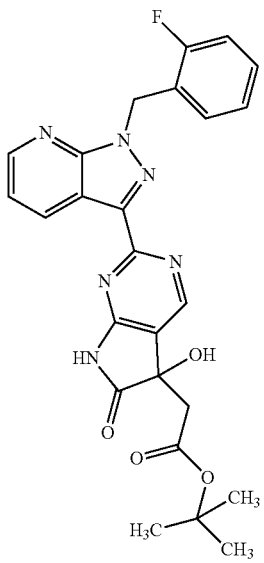 [SMILES: CC(C)(C)OC(=O)CC1(O)C(=O)Nc2nc(-c3nn(Cc4ccccc4F)c4ncccc34)ncc21]

At −45° C., 100 mg (0.267 mmol) of Example 16 were initially charged in THF (5 ml), 1.087 ml of a 1 M solution of bis(trimethylsilyl)lithium amide in THF were added and the mixture was stirred at −45° C. for 30 min. 126 mg (1.087 mmol) of tert-butyl acetate (dissolved in 5 ml of THF) were then added dropwise. The mixture was warmed to RT and stirred at this temperature overnight. Water was added to the reaction, and the mixture was adjusted to pH=4 using acetic acid. The mixture was then extracted three times with ethyl acetate. The combined organic phases were washed with water and saturated aqueous sodium chloride solution, dried over sodium sulphate, filtered and concentrated. The residue was purified by preparative HPLC (acetonitrile:water (+0.05% formic acid) gradient). This gave 73 mg of the title compound (55% of theory).

LC-MS (Method 1): $R_t$=0.96 min; MS (ESIpos): m/z=491 $(M+H)^+$ $^1$H NMR (400 MHz, DMSO-$d_6$): δ [ppm]=1.17 (s, 9H), 3.05 (q, 2H), 5.87 (s, 2H), 6.59 (s, 1H), 7.16 (t, 1H), 7.22-7.28 (m, 2H), 7.35-7.40 (m, 1H), 7.45 (dd, 1H), 8.66 (s, 1H), 8.68 (dd, 1H), 8.87 (dd, 1H), 11.64 (s, 1H).

Example 25

{2-[1-(2-Fluorobenzyl)-1H-pyrazolo[3,4-b]pyridin-3-yl]-5-hydroxy-6-oxo-6,7-dihydro-5H-pyrrolo[2,3-d]pyrimidin-5-yl}acetic acid

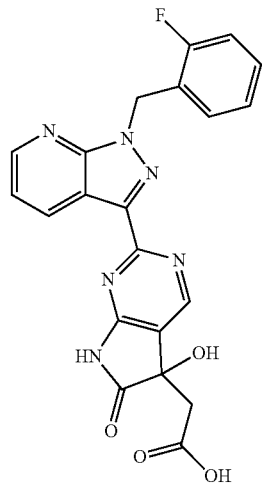 [SMILES: O=C(O)CC1(O)C(=O)Nc2nc(-c3nn(Cc4ccccc4F)c4ncccc34)ncc21]

60 mg (0.122 mmol) of Example 24 were stirred at RT in dichloromethane (1 ml) and trifluoroacetic acid (1 ml) for 30 min. The mixture was then concentrated, the residue was taken up in acetonitrile and water was added. A precipitate was filtered off, washed with acetonitrile and dried under high vacuum. This gave 42 mg of the title compound (80% of theory).

LC-MS (Method 1): $R_t$=0.80 min; MS (ESIpos): m/z=435 $(M+H)^+$ $^1$H NMR (400 MHz, DMSO-$d_6$): δ [ppm]=3.02 (d, 1H), 3.17 (d, 1H), 5.87 (s, 2H), 6.53 (s, 1H), 7.16 (t, 1H), 7.21-7.26 (m, 2H), 7.34-7.39 (m, 1H), 7.44 (dd, 1H), 8.66 (s, 1H), 8.68 (dd, 1H), 8.88 (dd, 1H), 11.56 (s, 1H).

Example 26

Methyl {2-[1-(2-fluorobenzyl)-1H-pyrazolo[3,4-b]pyridin-3-yl]-6-oxo-6,7-dihydro-5H-pyrrolo[2,3-d]pyrimidin-5-yl}carbamate

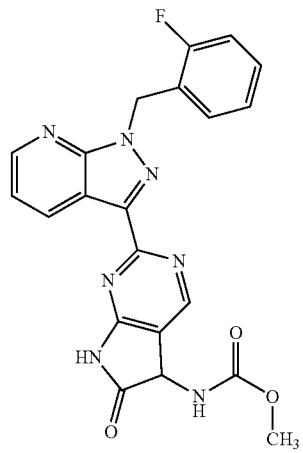 [SMILES: COC(=O)NC1C(=O)Nc2nc(-c3nn(Cc4ccccc4F)c4ncccc34)ncc21]

150 mg (about 0.319 mmol) of Example 73A were initially charged in pyridine (2 ml), and methyl chloroformate (24 μl in 1 ml dichloromethane) was then added until complete conversion had been achieved. The mixture was then concentrated and the residue was purified by preparative HPLC (acetonitrile:water (+0.05% formic acid) gradient). This gave 11 mg of the title compound in a purity of 90% (7% of theory).

LC-MS (Method 1): $R_t$=0.87 min; MS (ESIpos): m/z=434 (M+H)$^+$ $^1$H NMR (400 MHz, DMSO-$d_6$): δ [ppm]=3.55 (s, 3H), 5.10 (d, 1H), 5.86 (s, 2H), 7.16 (t, 1H), 7.21-7.26 (m, 2H), 7.35-7.38 (m, 1H), 7.44 (dd, 1H), 8.21 (d, 1H), 8.46 (s, 1H), 8.68 (dd, 1H), 8.87 (dd, 1H), 11.66 (s, 1H).

Example 27

3-[1-(2,3-Difluorobenzyl)-1H-pyrazolo[3,4-b]pyridin-3-yl]-7,7-dimethyl-5,7-dihydro-6H-pyrrolo[2,3-e][1,2,4]triazin-6-one

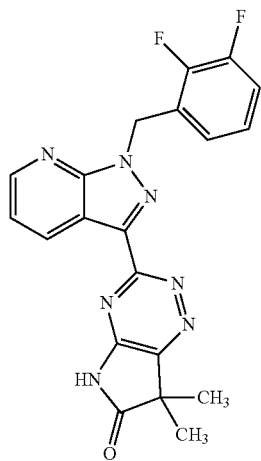 [SMILES: CC1(C)C(=O)Nc2nc(-c3nn(Cc4cccc(F)c4F)c4ncccc34)nnc21]

8 ml of phosphoryl chloride were added to 0.75 g (1.703 mmol) of the compound from Example 75A, and the mixture was stirred at RT overnight. The reaction mixture was then taken up in 120 ml of acetonitrile and, with ice cooling, stirred into 72 ml of concentrated ammonia solution (33% in water). The reaction mixture was stirred at room temperature for 3 days and then concentrated on a rotary evaporator. The residue was stirred with water and ethyl acetate and the aqueous phase was extracted twice with ethyl acetate. The combined organic phases were washed with saturated aqueous sodium chloride solution and then dried over sodium sulphate, filtered and concentrated on a rotary evaporator. The residue was purified by preparative HPLC (acetonitrile/water/water+ 1% TFA—40:55:5). This gave 134 mg of the title compound (19% of theory).

LC-MS (Method 4): $R_t$=0.98 min; MS (EIpos): m/z=408 [M+H]$^+$ $^1$H NMR (400 MHz, DMSO-$d_6$): δ [ppm]=1.46 (s, 6H), 5.94 (s, 2H), 7.07 (t, 1H), 7.15-7.19 (m, 1H), 7.37-7.42 (m, 1H), 7.49 (dd, 1H), 8.72 (dd, 1H), 8.86 (dd, 1H), 12.19 (s br, 1H).

Example 28

3-[1-(2,4-Difluorobenzyl)-1H-pyrazolo[3,4-b]pyridin-3-yl]-7,7-dimethyl-5,7-dihydro-6H-pyrrolo[2,3-e][1,2,4]triazin-6-one

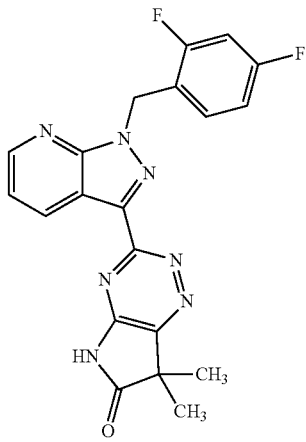

29 ml of phosphoryl chloride were added to 2.74 g (6.221 mmol) of the compound from Example 77A, and the mixture was stirred at RT overnight. The reaction mixture was then taken up in 430 ml of acetonitrile and, with ice cooling, stirred into 260 ml of concentrated ammonia solution (33% in water). The mixture was stirred at room temperature overnight and then concentrated on a rotary evaporator. The residue was stirred with water and ethyl acetate and the aqueous phase was extracted twice with ethyl acetate. The combined organic phases were washed with saturated aqueous sodium chloride solution and then dried over sodium sulphate, filtered and concentrated on a rotary evaporator. The residue was stirred with ethyl acetate and diethyl ether. A solid was filtered off with suction and then washed with diethyl ether and ethyl acetate. Drying under high vacuum gave 2.13 g of the title compound in a purity of 94% (79% of theory).

LC-MS (Method 1): $R_t$=0.93 min; MS (EIpos): m/z=408 [M+H]$^+$ $^1$H NMR (400 MHz, DMSO-$d_6$): δ [ppm]=1.45 (s, 6H), 5.86 (s, 2H), 7.05-7.10 (m, 1H), 7.26-7.32 (ddd, 1H), 7.34-7.40 (m, 1H), 7.48 (dd, 1H), 8.71 (dd, 1H), 8.85 (dd, 1H), 12.19 (s br, 1H).

Example 29

3-[5-Fluoro-1-(2,3,6-trifluorobenzyl)-1H-pyrazolo[3,4-b]pyridin-3-yl]-7,7-dimethyl-5,7-dihydro-6H-pyrrolo[2,3-e][1,2,4]triazin-6-one

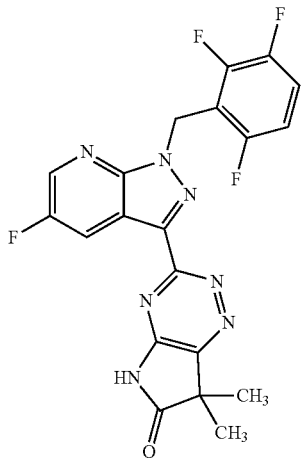 [SMILES: CC1(C)C(=O)Nc2nc(-c3nn(Cc4c(F)ccc(F)c4F)c4ncc(F)cc34)nnc21]

15 ml of phosphoryl chloride were added to 1.50 g (3.149 mmol) of the compound from Example 82A, and the mixture was stirred overnight. The reaction mixture was then taken up in 222 ml of acetonitrile and, with ice cooling, stirred into 133 ml of concentrated ammonia solution (33% in water). The reaction mixture was stirred at room temperature overnight and then concentrated on a rotary evaporator. Ethanol and water were added to the residue. A precipitate formed, which was filtered off and then washed with diethyl ether. Drying under high vacuum gave 982 mg of the title compound (70% of theory).

LC-MS (Method 1): $R_t$=1.01 min; MS (EIpos): m/z=444 [M+H]$^+$ $^1$H NMR (400 MHz, DMSO-d$_6$): δ [ppm]=1.44 (s, 6H), 5.92 (s, 2H), 7.21 (m, 1H), 7.57 (m, 1H), 8.54 (dd, 1H), 8.81 (dd, 1H), 12.19 (s br, 1H).

Example 30

2'-[5-Fluoro-1-(2-fluorobenzyl)-1H-pyrazolo[3,4-b]pyridin-3-yl]spiro[cyclopropane-1,5'-pyrrolo[2,3-d]pyrimidin]-6'(7'H)-one

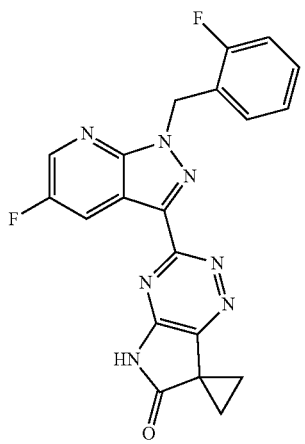 [SMILES: O=C1Nc2nc(-c3nn(Cc4ccccc4F)c4ncc(F)cc34)nnc2C12CC2]

1.28 g (2.84 mmol) of Example 87A were reacted analogously to the procedure of Example 4 with 478 mg (4.26 mmol) of potassium tert-butoxide in 60 ml of THF. This gave 426 mg of the title compound (36% of theory).

LC-MS (Method 4): $R_t$=1.04 min; MS (ESIpos): m/z=405 (M+H)$^+$ $^1$H NMR (400 MHz, DMSO-d$_6$): δ [ppm]=1.63 (dd, 2H), 1.87 (dd, 2H), 5.85 (s, 2H), 7.17 (dt, 1H), 7.20-7.31 (m, 2H), 7.38 (m, 1H), 8.38 (s, 1H), 8.59 (dd, 1H), 8.75 (dd, 1H), 11.77 (s br, 1H).

Example 31

2-[1-(2-Fluorobenzyl)-1H-pyrazolo[3,4-b]pyridin-3-yl]-5-(propan-2-ylidene)-5,7-dihydro-6H-pyrrolo[2,3-d]pyrimidin-6-one

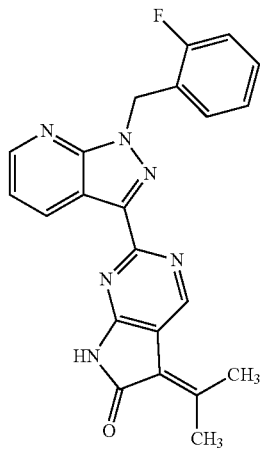 [SMILES: CC(C)=C1C(=O)Nc2nc(-c3nn(Cc4ccccc4F)c4ncccc34)ncc21]

500 mg (1.388 mmol) of Example 4 were initially charged in acetone (50 ml), 0.274 ml (2.775 mmol) of piperidine was added and the mixture was heated under reflux for 1 h. After cooling, a precipitate was filtered off and washed with acetone, and the filtrate was concentrated under reduced pressure. This residue was then purified by chromatography on silica gel (mobile phase: cyclohexane/ethyl acetate gradient). The material obtained in this manner was once more slurried in ethyl acetate, filtered off, washed with ethyl acetate and dried under high vacuum. This gave 101 mg of the title compound as a solid (18% of theory).

LC-MS (Method 4): $R_t$=1.06 min; MS (ESIpos): m/z=401 (M+H)$^+$ $^1$H NMR (400 MHz, DMSO-d$_6$): δ [ppm]=2.41 (s, 3H), 5.86 (s, 2H), 7.14-7.18 (m, 1H), 7.22-7.28 (m, 2H), 7.33-7.41 (m, 1H), 7.44 (dd, 1H), 8.67 (dd, 1H), 8.83 (s, 1H), 8.90 (dd, 1H), 11.67 (s, 1H).

Example 32

2'-[1-(2-Fluorobenzyl)-1H-pyrazolo[3,4-b]pyridin-3-yl]-2,2-dimethylspiro[cyclopropane-1,5'-pyrrolo[2,3-d]pyrimidin]-6'(7'H)-one

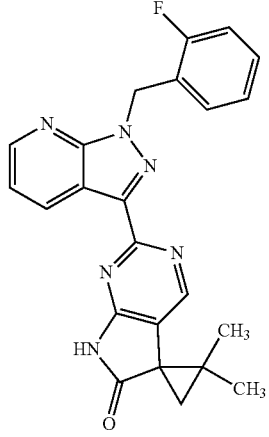 [SMILES: CC1(C)CC12C(=O)Nc1nc(-c3nn(Cc4ccccc4F)c4ncccc34)ncc12]

Under argon, 19.97 mg (0.499 mmol) of sodium hydride (60% in mineral oil) and 164 mg (0.749 mmol) of trimethylsulphoxonium iodide were initially charged, and 1.9 ml of DMSO were added. The mixture was then stirred at RT for 1 h, and 100 mg (0.250 mmol) of Example 31, dissolved in DMSO (4.6 ml), were then added dropwise. After 1 h at RT, the mixture was heated at 50° C. for 6 h. The crude mixture was purified by preparative HPLC (acetonitrile:water (+0.05% formic acid) gradient). This gave 45 mg of the title compound (42% of theory).

LC-MS (Method 1): $R_t$=1.07 min; MS (ESIpos): m/z=415 $(M+H)^+$

1H NMR (400 MHz, DMSO-$d_6$): δ [ppm]=1.41 (s, 3H), 1.44 (s, 3H), 1.73 (d, 1H), 1.92 (d, 1H), 5.85 (s, 2H), 7.14-7.18 (m, 1H), 7.22-7.26 (m, 2H), 7.34-7.38 (m, 1H), 7.43 (dd, 1H), 8.47 (s, 1H), 8.67 (dd, 1H), 8.88 (dd, 1H), 11.69 (s, 1H).

B. Assessment of the Pharmacological Activity

The pharmacological effect of the compounds according to the invention can be shown in the following assays:

B-1. Vessel-Relaxing Action In Vitro

Rabbits are stunned with a blow on the back of the neck and exsanguinated. The aorta is removed, freed from adhering tissue, separated into rings with a width of 1.5 mm, and placed individually, with preloading, in 5-ml organ baths with carbogen-gassed Krebs-Henseleit solution at 37° C. with the following composition (mM in each case): sodium chloride: 119; potassium chloride: 4.8; calcium chloride dihydrate: 1; magnesium sulphate heptahydrate: 1.4; potassium dihydrogen phosphate: 1.2; sodium hydrogen carbonate: 25; glucose: 10. The contraction force is recorded with Statham UC2 cells, amplified and digitized via an A/D converter (DAS-1802 HC, Keithley Instruments Munich) and recorded in parallel on a continuous-line recorder. To produce contraction, phenylephrine is added to the bath cumulatively in increasing concentration. After several control cycles, the test substance is added in increasing dosage in each subsequent pass and the level of contraction is compared with the level of contraction reached in the immediately preceding pass. This is used for calculating the concentration that is required to reduce the level of the control value by 50% ($IC_{50}$ value). The standard application volume is 5 µl, and the proportion of DMSO in the bath solution corresponds to 0.1%.

Representative $IC_{50}$ values for the compounds according to the invention are shown in the following table (Table 1):

TABLE 1

| Example No. | $IC_{50}$ [nM] |
|---|---|
| 1 | 12 |
| 2 | 12 |
| 7 | 45 |
| 8 | 13 |
| 10 | 6 |
| 11 | 4 |
| 14 | 65 |
| 17 | 13 |
| 18 | 93 |
| 19 | 157 |
| 20 | 45 |
| 23 | 15 |
| 24 | 269 |
| 26 | 840 |
| 27 | 54 |
| 28 | 103 |
| 30 | 97 |

B-2. Action on Recombinant Guanylate Cyclase Reporter Cell Line

The cellular action of the compounds according to the invention is determined on a recombinant guanylate cyclase reporter cell line, as described in F. Wunder et al., *Anal. Biochem.* 339, 104-112 (2005).

Representative values (MEC=minimal effective concentration) for the compounds according to the invention are shown in the following table (Table 2):

TABLE 2

| Example No. | MEC [µM] |
|---|---|
| 1 | 0.01 |
| 2 | 0.01 |
| 3 | 0.03 |
| 4 | 0.03 |
| 5 | 0.03 |
| 6 | 0.03 |
| 7 | 0.03 |
| 8 | 0.03 |
| 9 | 0.03 |
| 10 | 0.03 |
| 11 | 0.03 |
| 12 | 0.1 |
| 13 | 0.1 |
| 14 | 0.1 |
| 15 | 0.3 |
| 16 | 1.0 |
| 17 | 0.1 |
| 18 | 0.03 |
| 19 | 0.03 |
| 20 | 0.03 |
| 21 | 0.1 |
| 22 | 0.03 |
| 23 | 0.03 |
| 24 | 0.3 |
| 25 | 1.0 |
| 26 | 0.3 |
| 27 | 0.03 |
| 28 | 0.3 |
| 29 | 0.1 |
| 30 | 0.03 |
| 77A | 1.0 |
| 82A | 0.3 |

B-3. Radiotelemetric Blood Pressure Measurement on Awake, Spontaneously Hypertensive Rats The blood pressure measurement on awake rats described below uses a commercially available telemetry system from the company DATA SCIENCES INTERNATIONAL DSI, USA.

The system consists of 3 main components:
  implantable transmitter (Physiotel® Telemetry Transmitter)
  receiver (Physiotel® Receiver), which are connected via a multiplexer (DSI Data Exchange Matrix) to a
  data acquisition computer.

The telemetry system provides continuous acquisition of blood pressure, heart rate and body movement on awake animals in their usual living space.

Animal Material

The investigations are carried out on adult female, spontaneously hypertensive rats (SHR Okamoto) with a body weight of >200 g. SHR/NCrl from Okamoto Kyoto School of Medicine, 1963 were crossed from male Wistar Kyoto rats with greatly increased blood pressure and females with slightly raised blood pressure and were delivered in F13 to the U.S. National Institutes of Health.

After transmitter implantation, the experimental animals are kept individually in Makrolon cages, type 3. They have free access to standard feed and water.

The day—night rhythm in the testing laboratory is alternated by the room lighting at 06:00 hours in the morning and at 19:00 hours in the evening.

Transmitter Implantation

The TA11 PA—C40 telemetry transmitters used are implanted surgically in the experimental animals under aseptic conditions at least 14 days before the first test. The animals provided with this instrumentation can be used again after the wound has healed and the implant has become incorporated.

For implantation, the fasting animals are anaesthetized with pentobarbital (Nembutal, Sanofi: 50 mg/kg i.p.) and are shaved and disinfected on a wide area of the abdomen. After opening the abdominal cavity along the linea alba, the liquid-filled measuring catheter of the system is inserted above the bifurcation in the cranial direction into the aorta descendens and secured with tissue adhesive (VetBonD™, 3M). The transmitter housing is fixed intraperitoneally on the abdominal wall musculature and the wound is closed layer by layer.

Postoperatively, an antibiotic is administered to prevent infection (Tardomyocel COMP Bayer 1 ml/kg s.c.)

Substances and Solutions

Unless described otherwise, the test substances are in each case administered orally by stomach tube to a group of animals (n=6). Corresponding to an application volume of 5 ml/kg body weight, the test substances are dissolved in suitable solvent mixtures or suspended in 0.5% Tylose.

A group of animals treated with solvents is used as control.

Test Procedure

The present telemetry measuring device is configured for 24 animals. Each test is recorded under a test number (test year month day).

The instrumented rats living in the unit are each assigned their own receiving antenna (1010 Receiver, DSI).

The implanted transmitters can be activated from outside by an in-built magnetic switch. They are switched to transmission at the start of the tests. The signals emitted can be recorded online by a data acquisition system (Dataquest TM A.R.T. for WINDOWS, DSI) and processed appropriately. The data are saved in each case to a folder opened for this, which bears the test number.

In the standard procedure, the following are measured, in each case for 10 seconds:
systolic blood pressure (SBP)
diastolic blood pressure (DBP)
mean arterial pressure (MAP)
heart rate (HR)
activity (ACT).

Recording of the measured values is repeated at 5-minute intervals under computer control. The source data recorded as absolute value are corrected in the diagram with the currently measured barometric pressure (Ambient Pressure Reference Monitor; APR-1) and saved in individual data. Further technical details can be found in the extensive documentation of the manufacturer (DSI).

Unless described otherwise, the test substances are administered on the test day at 09.00 hours. Following application, the parameters described above are measured for 24 hours.

Evaluation

After the end of the test, the individual data recorded are sorted with the analysis software (DATAQUEST TM A. R.T. TM ANALYSIS). The 2 hours before application are taken as the blank value here, so that the selected data set comprises the period from 07:00 hours on the test day to 09:00 hours on the next day.

The data are smoothed for a pre-settable time by mean value determination (15-minute average) and transferred as text file to a storage medium. The pre-sorted and compressed measured values are transferred to Excel templates and presented as tables. The data recorded are saved per test day in a specific folder, which bears the test number. Results and test protocols are filed in folders, sorted in paper form by numbers.

Literature

Klaus Witte, Kai Hu, Johanna Swiatek, Claudia Müssig, Georg Ertl and Björn Lemmer: Experimental heart failure in rats: effects on cardiovascular circadian rhythms and on myocardial β-adrenergic signaling. Cardiovasc Res 47 (2): 203-405, 2000; Kozo Okamoto: Spontaneous hypertension in rats. Int Rev Exp Pathol 7: 227-270, 1969; Maarten van den Buuse: Circadian Rhythms of Blood Pressure, Heart Rate, and Locomotor Activity in Spontaneously Hypertensive Rats as Measured with Radio-Telemetry. Physiology & Behavior 55(4): 783-787, 1994

B-4. Determination of Pharmacokinetic Parameters after Intravenous and Oral Administration The pharmacokinetic parameters of the compounds of the formula (I) according to the invention are determined in male CD-1 mice, male Wistar rats and/or female beagles. The administration volume is 5 ml/kg for mice, 5 ml/kg for rats and 0.5 ml/kg for dogs. Intravenous administration is via a formulation of species-specific plasma/DMSO (99/1) in the case of mice and rats and via water/PEG400/ethanol (50/40/10 or 30/60/10) in the case of dogs. For easier removal of blood, a silicone catheter is inserted into the right Vena jugularis externa of the rats before the administration of substance. The surgical intervention takes place one day prior to the experiment with isofluran anaesthesia and administration of an analgetic (atropine/rimadyl (3/1) 0.1 ml s.c.). Substance administration is as i.v. bolus in the case of mice and rats and via a 15-minute infusion in the case of dogs. Removal of blood is after 0.033, 0.083, 0.17, 0.5, 1, 2, 3, 4, 6, 7 and 24 hours in the case of rats, after 0.033, 0.083, 0.17, 0.5, 1, 2, 3, 4, 6, 7, 24, 48 and 72 hours in the case of mice and after 0.083, 0.25, 0.28 0.33, 0.42, 0.75, 1, 2, 3, 4, 6, 7 and 24 hours in the case of dogs. For all species, oral administration of the dissolved substance via gavage is carried out based on a water/PEG400/ethanol formulation (50/40/10). Here, the removal of blood from rats is after 0.083, 0.17, 0.5, 0.75, 1, 2, 3, 4, 6, 7 and 24 hours and from dogs after 0.083, 0.17, 0.5, 0.75, 1, 2, 3, 4, 6, 7, 24, 30 and 48 hours. The blood is removed into heparinized tubes. The blood plasma is then obtained by centrifugation; if required, it can be stored at −20° C. until further processing.

An internal standard (ZK 228859) is added to the samples of the compounds of the formula (I) according to the invention, calibration samples and QCs, and the protein is precipitated using excess acetonitrile. After addition of an ammonium acetate buffer (0.01 M, pH 6.8) and subsequent vortexing, the mixture is centrifuged at 1000 g and the supernatant is examined by LC-MS/MS (API 4000, AB Sciex). Chromatographic separation is carried out on an Agilent 1100-HPLC. The injection volume is 10 µl. The separation column used is a Phenomenex Luna 5µ C8(2) 100 A 50×2 mm, adjusted to a temperature of 40° C. A binary mobile phase gradient at 500 µl/min is used (A: 0.01 M ammonium acetate buffer pH 6.8, B: 0.1% formic acid in acetonitrile): 0 min (90% A), 1 min (90% A), 3 min (15% A), 4 min (15% A), 4.50 min (90% A), 6 min (90% A). The temperature of the Turbo V ion source is 500° C. The following MS instrument parameters are used: curtain gas 15 units, ion spray voltage 4.8 kV, gas 1 45 units, gas 2 35 units, CAD gas 40 units. The substances are quantified by peak heights or areas using extracted ion chromatograms of specific MRM experiments.

The pharmacokinetic parameters such as AUC, $C_{max}$, $t_{1/2}$ (terminal half-life), MRT (mean residence time) and CL (clearance) are calculated by means of the validated pharmacokinetics calculation program KinEx (Vers. 2.5 and 3) from the plasma concentration-time curves obtained.

As substance quantification takes place in plasma, the blood/plasma distribution of the substance must be determined for appropriate adjustment of the pharmacokinetic parameters. For this, a defined amount of the substance in heparinized whole blood of the corresponding species is incubated for 20 min in the tumbling roller mixer. After centrifugation at 1000 g, the plasma concentration is measured (see above) and the $C_{blood}/C_{plasma}$ value is determined by finding the quotient.

Following intravenous administration of 0.3 mg/kg of Example 1, 18, 19 and 27 in rats, the following values were recorded:

|  | Example | | | |
| --- | --- | --- | --- | --- |
|  | 1 | 18 | 19 | 27 |
| $CL_{blood}$ [L/h/kg] | 1.1 | 0.46 | 0.32 | 0.35 |
| terminal half-life [h] | 0.9 | 1.4 | 3.0 | 5.6 |
| mean residence time [h] | 1.2 | 1.9 | 4.0 | 7.3 |

C. Exemplary Embodiments of Pharmaceutical Compositions

The compounds according to the invention can be converted into pharmaceutical preparations in the following ways:

Tablet:
Composition:
  100 mg of the compound according to the invention, 50 mg of lactose (monohydrate), 50 mg of maize starch (native), 10 mg of polyvinylpyrrolidone (PVP 25) (from BASF, Ludwigshafen, Germany) and 2 mg of magnesium stearate.
  Tablet weight 212 mg, diameter 8 mm, radius of curvature 12 mm Production:
  The mixture of compound according to the invention, lactose and starch is granulated with a 5% strength solution (m/m) of the PVP in water. The granules are dried and then mixed with the magnesium stearate for 5 minutes. This mixture is compressed in a conventional tablet press (see above for format of the tablet). A guideline compressive force for the compression is 15 kN.

Suspension which can be Administered Orally:
Composition:
  1000 mg of the compound according to the invention, 1000 mg of ethanol (96%), 400 mg of Rhodigel® (xanthan gum from FMC, Pennsylvania, USA) and 99 g of water.
  10 ml of oral suspension correspond to a single dose of 100 mg of the compound according to the invention.

Production:
  The Rhodigel is suspended in ethanol, and the compound according to the invention is added to the suspension. The water is added while stirring. The mixture is stirred for about 6 h until the swelling of the Rhodigel is complete.

Solution which can be Administered Orally:
Composition:
  500 mg of the compound according to the invention, 2.5 g of polysorbate and 97 g of polyethylene glycol 400. 20 g of oral solution correspond to a single dose of 100 mg of the compound according to the invention.

Production:
  The compound according to the invention is suspended in the mixture of polyethylene glycol and polysorbate with stirring. The stirring process is continued until the compound according to the invention has completely dissolved.

i.v. Solution:
  The compound according to the invention is dissolved in a concentration below the saturation solubility in a physiologically tolerated solvent (e.g. isotonic saline, 5% glucose solution and/or 30% PEG 400 solution). The solution is sterilized by filtration and used to fill sterile and pyrogen-free injection containers.

The invention claimed is:
1. A compound of formula (I)

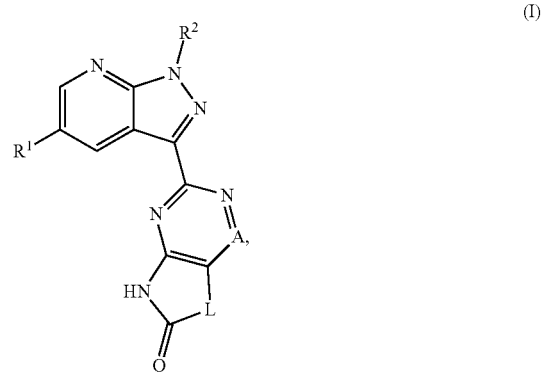

in which
A represents nitrogen,
L represents a group *—$CR^{4A}R^{4B}$—$(CR^{5A}R^{5B})_p$-#,
  where
  * represents the point of attachment to the carbonyl group,
  # represents the point of attachment to the pyrimidine or triazine ring,
  p represents a number 0, 1 or 2,
  $R^{4A}$ represents hydrogen, fluorine, ($C_1$-$C_4$)-alkyl or hydroxyl,
  $R^{4B}$ represents hydrogen, fluorine, ($C_1$-$C_4$)-alkyl, trifluoromethyl, ($C_1$-$C_4$)-alkoxy-carbonylamino or phenyl,
    where ($C_1$-$C_4$)-alkyl may be substituted by 1 or 2 substituents independently of one another selected from the group consisting of fluorine, trifluoromethyl, hydroxyl, hydroxycarbonyl and ($C_1$-$C_4$)-alkoxycarbonyl,
  or
  $R^{4A}$ and $R^{4B}$ together with the carbon atom to which they are attached form an oxo group, a 3- to 6-membered carbocycle or a 4- to 6-membered heterocycle,
    where the 3- to 6-membered carbocycle and the 4- to 6-membered heterocycle may be substituted by 1 or 2 substituents independently of one another selected from the group consisting of fluorine and ($C_1$-$C_4$)-alkyl,
  or
  $R^{4A}$ and $R^{4B}$ together with the carbon atom to which they are attached form a ($C_2$-$C_4$)-alkenyl group,
  $R^{5A}$ represents hydrogen, fluorine, ($C_1$-$C_4$)-alkyl or hydroxyl,
  $R^{5B}$ represents hydrogen, fluorine, ($C_1$-$C_4$)-alkyl or trifluoromethyl, R$^1$ represents hydrogen or fluorine,
R$^2$ represents benzyl,
  where benzyl is substituted by 1 to 3 fluorine substituents,
or an N-oxide, salt, solvate, salt of the N-oxide, or and solvate of the N-oxide or salt thereof.

2. The compound of claim 1, in which
A represents nitrogen,
L represents a group *—CR$^{4A}$R$^{4B}$—(CR$^{5A}$R$^{5B}$)$_p$-#,
  where
    * represents the point of attachment to the carbonyl group,
    # represents the point of attachment to the pyrimidine or triazine ring,
  p represents a number 0 or 1,
  R$^{4A}$ represents hydrogen, fluorine, methyl, ethyl or hydroxyl,
  R$^{4B}$ represents hydrogen, fluorine, methyl, ethyl, trifluoromethyl, methoxycarbonylamino or phenyl,
    where methyl and ethyl may be substituted by 1 or 2 substituents independently of one another selected from the group consisting of fluorine, trifluoromethyl and hydroxyl,
  or
  R$^{4A}$ and R$^{4B}$ together with the carbon atom to which they are attached form a cyclopropyl, cyclobutyl, cyclopentyl, azetidinyl, pyrrolidinyl, tetrahydrofuranyl, piperidinyl or tetrahydropyranyl ring,
    where the cyclopropyl, cyclobutyl, cyclopentyl, azetidinyl, pyrrolidinyl, tetrahydrofuranyl, piperidinyl or tetrahydropyranyl ring may be substituted by 1 or 2 substituents independently of one another selected from the group consisting of fluorine and methyl,
  R$^{5A}$ represents hydrogen, fluorine, methyl, ethyl or hydroxyl,
  R$^{5B}$ represents hydrogen, fluorine, methyl, ethyl or trifluoromethyl,
R$^1$ represents hydrogen or fluorine,
R$^2$ represents benzyl,
  where benzyl is substituted by 1 to 3 fluorine substituents,
or a salt, solvate, or solvates of the salt thereof.

3. The compound of claim 1, in which
A represents nitrogen,
L represents a group *—CR$^{4A}$R$^{4B}$—(CR$^{5A}$R$^{5B}$)$_p$-#,
  where
    * represents the point of attachment to the carbonyl group,
    # represents the point of attachment to the pyrimidine ring,
  p represents a number 0,
  R$^{4A}$ represents hydrogen, fluorine or methyl,
  R$^{4B}$ represents hydrogen, fluorine, methyl or trifluoromethyl,
  or
  R$^{4A}$ and R$^{4B}$ together with the carbon atom to which they are attached form a cyclopropyl or cyclobutyl ring,
    where the cyclopropyl and the cyclobutyl ring may be substituted by 1 or 2 substituents independently of one another selected from the group consisting of fluorine and methyl,
R$^1$ represents hydrogen or fluorine,
R$^2$ represents benzyl,
  where benzyl is substituted by 1 or 2 fluorine substituents,
or a salt, solvate or solvate of the salt thereof.

4. A process for preparing the compound of claim 1, comprising

[A] reacting a compound of formula (II)

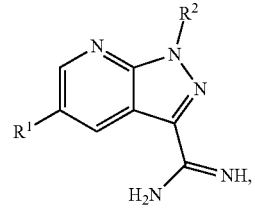

(II)

in which R$^1$ and R$^2$ each have the meanings given in claim 1, in an inert solvent in the presence of a suitable base with hydrazine hydrate to give a compound of the formula (XI)

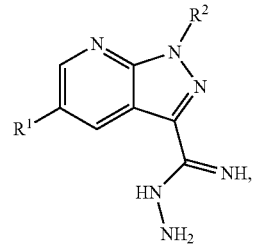

(XI)

in which R$^1$ and R$^2$ each have the meanings given in claim 1, reacting the compound of formula (XI) in an inert solvent with a compound of formula (XII)

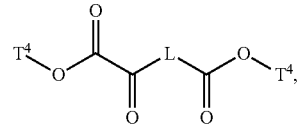

(XII)

in which L has the meaning given in claim 1 and
T$^4$ represents (C$_1$-C$_4$)-alkyl,
to give a compound of formula (XIII)

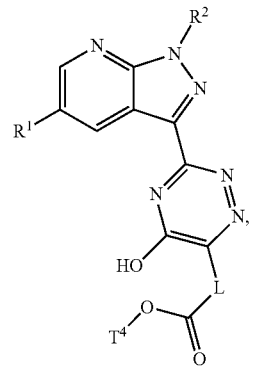

(XIII)

in which L, R$^1$, R$^2$ and T$^4$ each have the meanings given in claim 1, converting the compound of formula (XIII) with phosphoryl chloride into a compound of formula (XIV)

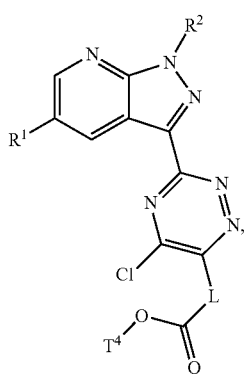

(XIV)

in which L, R¹, R² and T⁴ each have the meanings given in claim 1, and the compound of formula (XIV) is reacted directly with ammonia to give a compound of formula (XV)

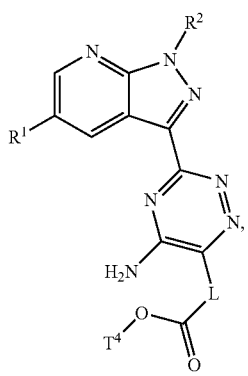

(XV)

in which L, R¹, R² and T⁴ each have the meanings given in claim 1, and cyclizing the compound of formula (XV) in an inert solvent in the presence of a suitable base to give a compound of formula (I-D)

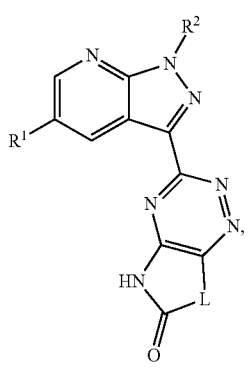

(I-D)

in which L, R¹ and R² each have the meanings given in claim 1, and the resulting compound of formula (I-D) is optionally converted with the appropriate (i) solvent and/or (ii) acid or base into the solvate, salt and/or solvate of the salt thereof.

5. A compound of formula (XV)

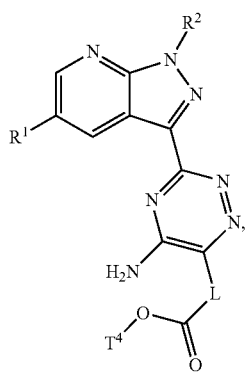

(XV)

in which

L represents a group $*-CR^{4A}R^{4B}-(CR^{5A}R^{5B})_p-\#$, where

* represents the point of attachment to the carbonyl group, # represents the point of attachment to the triazine ring, p represents a number 0, 1 or 2, $R^{4A}$ represents hydrogen, fluorine, $(C_1-C_4)$-alkyl or hydroxyl, $R^{4B}$ represents hydrogen, fluorine, $(C_1-C_4)$-alkyl, trifluoromethyl, $(C_1-C_4)$-alkoxycarbonylamino or phenyl, where $(C_1-C_4)$-alkyl may be substituted by 1 or 2 substituents independently of one another selected from the group consisting of fluorine, trifluoromethyl, hydroxyl, hydroxycarbonyl and $(C_1C_4)$-alkoxycarbonyl, or $R^{4A}$ and $R^{4B}$ together with the carbon atom to which they are attached form a 3- to 6-membered carbocycle or a 4- to 6-membered heterocycle, where the 3- to 6-membered carbocycle and the 4- to 6-membered heterocycle may be substituted by 1 or 2 substituents independently of one another selected from the group consisting of fluorine and $(C_1-C_4)$-alkyl, $R^{5A}$ represents hydrogen, fluorine, $(C_1-C_4)$-alkyl or hydroxyl, $R^{5B}$ represents hydrogen, fluorine, $(C_1-C_4)$-alkyl or trifluoromethyl, $R^1$ represents hydrogen or fluorine, $R^2$ represents benzyl, where benzyl is substituted by 1 to 3 fluorine substituents, $T^4$ represents $(C_1-C_4)$-alkyl, or a salt, solvate or solvate of the salt thereof.

6. A compound of formula (XIII)

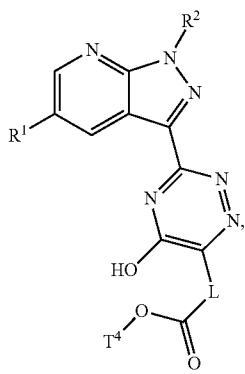

(XIII)

in which

L represents a group *—CR$^{4A}$R$^{4B}$—(CR$^{5A}$R$^{5B}$)$_p$—#,
where
* represents the point of attachment to the carbonyl group,
# represents the point of attachment to the triazine ring,
p represents a number 0, 1 or 2,
R$^{4A}$ represents hydrogen, fluorine, (C$_1$-C$_4$)-alkyl or hydroxyl,
R$^{4B}$ represents hydrogen, fluorine, (C$_1$-C$_4$)-alkyl, trifluoromethyl, (C$_1$-C$_4$)-alkoxycarbonylamino or phenyl,
where (C$_1$-C$_4$)-alkyl may be substituted by 1 or 2 substituents independently of one another selected from the group consisting of fluorine, trifluoromethyl, hydroxyl, hydroxycarbonyl and (C$_1$-C$_4$)-alkoxycarbonyl,
or
R$^{4A}$ and R$^{4B}$ together with the carbon atom to which they are attached form a 3- to 6-membered carbocycle or a 4- to 6-membered heterocycle,
where the 3- to 6-membered carbocycle and the 4- to 6-membered heterocycle may be substituted by 1 or 2 substituents independently of one another selected from the group consisting of fluorine and (C$_1$-C$_4$)-alkyl,
R$^{5A}$ represents hydrogen, fluorine, (C$_1$-C$_4$)-alkyl or hydroxyl,
R$^{5B}$ represents hydrogen, fluorine, (C$_1$-C$_4$)-alkyl or trifluoromethyl,
R$^1$ represents hydrogen or fluorine,
R$^2$ represents benzyl,
where benzyl is substituted by 1 to 3 fluorine substituents,
T$^4$ represents (C$_1$-C$_4$)-alkyl,
or a salt, solvate, or solvate of the salt thereof.

7. A pharmaceutical composition comprising the compound of claim 1 and an inert, non-toxic, pharmaceutically suitable auxiliary.

8. The pharmaceutical composition of claim 7, further comprising an active compound selected from the group consisting of an organic nitrate, an NO donor, a cGMP-PDE inhibitor, an agent having antithrombotic activity, an agent for lowering blood pressure, and an agent for altering lipid metabolism.

9. A method for the treatment of hypertension and pulmonary hypertension, comprising administering an effective amount of at least one compound of claim 1 to a human or animal in need thereof.

10. A method of treatment of, hypertension and pulmonary hypertension comprising administering an effective amount of the pharmaceutical composition of claim 7 to an animal or human in need thereof.

* * * * *